United States Patent
El Hibouri et al.

(10) Patent No.: US 12,027,235 B1
(45) Date of Patent: Jul. 2, 2024

(54) SYSTEMS AND METHODS FOR ARTIFICIAL INTELLIGENCE-BASED BINDING SITE PREDICTION AND SEARCH SPACE FILTERING FOR BIOLOGICAL SCAFFOLD DESIGN

(71) Applicant: Pythia Labs, Inc., Los Angeles, CA (US)

(72) Inventors: Mohamed El Hibouri, Los Angeles, CA (US); Julien Jorda, Los Angeles, CA (US); Thibault Marie Duplay, Los Angeles, CA (US); Ramin Ansari, Los Angeles, CA (US); Matthias Maria Alessandro Malago, Santa Monica, CA (US); Lisa Juliette Madeleine Barel, Los Angeles, CA (US); Joshua Laniado, Los Angeles, CA (US)

(73) Assignee: Pythia Labs, Inc., Los Angeles, CA (US)

( * ) Notice: Subject to any disclaimer, the term of this patent is extended or adjusted under 35 U.S.C. 154(b) by 0 days.

(21) Appl. No.: 18/089,319

(22) Filed: Dec. 27, 2022

(51) Int. Cl.
| | | |
|---|---|---|
| *G01N 33/48* | (2006.01) | |
| *G16B 15/30* | (2019.01) | |
| *G16B 40/00* | (2019.01) | |
| *G16B 45/00* | (2019.01) | |

(52) U.S. Cl.
CPC .............. *G16B 15/30* (2019.02); *G16B 40/00* (2019.02); *G16B 45/00* (2019.02)

(58) Field of Classification Search
None
See application file for complete search history.

(56) References Cited

U.S. PATENT DOCUMENTS

| | | |
|---|---|---|
| 5,526,281 A | 6/1996 | Chapman et al. |
| 9,296,802 B2 | 3/2016 | Choi et al. |
| 9,373,059 B1 | 6/2016 | Heifets et al. |
| 11,256,994 B1 | 2/2022 | Bucher et al. |
| 11,450,407 B1 | 9/2022 | Laniado et al. |
| 11,742,057 B2 | 8/2023 | Laniado et al. |
| 11,869,629 B2 | 1/2024 | Laniado et al. |
| 2002/0072864 A1 | 6/2002 | Lacroix et al. |
| 2002/0133297 A1 | 9/2002 | Yang et al. |
| 2002/0147547 A1 | 10/2002 | Desjarlais |
| 2004/0199334 A1 | 10/2004 | Kovesdi et al. |
| 2012/0239367 A1 | 9/2012 | Tong et al. |
| 2013/0330335 A1 | 12/2013 | Bremel et al. |
| 2016/0300127 A1 | 10/2016 | Heifets et al. |
| 2018/0260517 A1 | 9/2018 | Blattner et al. |
| 2018/0285731 A1 | 10/2018 | Heifets et al. |
| 2018/0341754 A1 | 11/2018 | Fan et al. |
| 2019/0272887 A1 | 9/2019 | Feinberg et al. |
| 2019/0325986 A1 | 10/2019 | Agarwal et al. |
| 2020/0342953 A1 | 10/2020 | Morrone et al. |
| 2021/0304847 A1 | 9/2021 | Senior et al. |
| 2022/0165366 A1 | 5/2022 | Zubarev et al. |
| 2022/0375538 A1 | 11/2022 | Das et al. |
| 2023/0022022 A1 | 1/2023 | Laniado et al. |
| 2023/0034425 A1 | 2/2023 | Laniado et al. |
| 2023/0040576 A1 | 2/2023 | Laniado et al. |
| 2023/0083810 A1 | 3/2023 | Xu et al. |
| 2024/0038337 A1 | 2/2024 | Laniado et al. |
| 2024/0096444 A1 | 3/2024 | Laniado et al. |

FOREIGN PATENT DOCUMENTS

| | | |
|---|---|---|
| EP | 3739589 A1 | 11/2020 |
| KR | 2021-0145059 A | 12/2021 |
| WO | WO-2013/040142 A2 | 3/2013 |
| WO | WO-2018/213767 A1 | 11/2018 |
| WO | WO-2020/123302 A1 | 6/2020 |
| WO | WO-2023/004116 A1 | 1/2023 |

OTHER PUBLICATIONS

Screen captures from YouTube clip entitled "A friendly introduction to Recurrent Neural Networks," 4 pages, Uploaded Aug. 18, 2017 by user "Serrano. Academy," Retrieved from Internet: <https://youtu.be/UNmqTiOnRfg?si=VaKICmaW6wQGydAz>.*
Nguyen, Thin, et al. "GraphDTA: Predicting drug-target binding affinity with graph neural networks." Bioinformatics 37.8 (2021): 1140-1147.*
Berkholz, D.S. et al., Conformation Dependence of Backbone Geometry in Proteins, Structure, 17(10):1316-1325 (2009).
Bose, A.J. et al., SE(3)-Stochastic Flow Matching for Protein Backbone Generation, arXiv Preprint, available online at: https://arxiv.org/abs/2310.02391v1, 30 pages, (Oct. 3, 2023).
Chen, R.T.Q. and Lipman, Y., Riemannian Flow Matching on General Geometries, arXiv Preprint, available online at: https://arxiv.org/abs/2302.03660v1, 16 pages, (Feb. 7, 2023).
Darcet, T. et al., Vision Transformers Need Registers, arXiv Preprint, available online at: https://arxiv.org/abs/2309.16588, 16 pages, (Sep. 28, 2023).

(Continued)

*Primary Examiner* — Anna Skibinsky
(74) *Attorney, Agent, or Firm* — Choate, Hall & Stewart LLP; William R. Haulbrook; Ronen Adato

(57) ABSTRACT

Presented herein are systems and methods for predicting which amino acid sites of a target proteins of interest will be binding sites—for example, locations and/or identifications of particular amino acid sites—that are amenable or likely to participate in binding interactions with other ligands, such as other proteins. These binding site predictions may, for example, be generated for target proteins that are implicated in disease and, accordingly, be targets for potential new biologic drugs. Binding site prediction technologies described herein may thus be used to guide design and/or testing of new and/or custom biologic drugs, either experimentally or in-silico. In this manner, binding site prediction technologies of the present disclosure can facilitate design and/or testing of new biologic drugs, leading to new and improved candidates and/or improving, among other things, developmental efficiency, success rates of clinical trials, and time to market.

19 Claims, 31 Drawing Sheets

(56) References Cited

OTHER PUBLICATIONS

Dauparas, J. et al., Robust deep learning-based protein sequence design using ProteinMPNN, Science, 378(6615):49-56 (2022).
Jing, B. et al., AlphaFold Meets Flow Matching for Generating Protein Ensembles, 37th Conference on Neural Information Processing Systems (NeurIPS 2023), 13 pages, (2023).
Jumper, J. et al., Highly accurate protein structure prediction with AlphaFold, With Supplementary Information, Nature, 596(7873):583-589 (2021).
Lin, Z. et al., Evolutionary-scale prediction of atomic-level protein structure with a language model, Science, 379(6637):1123-1130 (2023).
Lipman, Y. et al., Flow Matching for Generative Modeling, Version 2 (V2), arXiv Preprint, available online at: https://arxiv.org/abs/2210.02747, 28 pages, (Feb. 8, 2023).
Peebles, W. and Xie, S., Scalable Diffusion Models with Transformers, arXiv Preprint, available online at: https://arxiv.org/abs/2212.09748, 25 pages, (Mar. 2, 2023).
Su, J. et al., RoFormer: Enhanced Transformer with Rotary Position Embedding, arXiv Preprint, available online at: https://arxiv.org/abs/2104.09864, 14 pages, (Aug. 9, 2022).
Trippe, B.L. et al., Diffusion probabilistic modeling of protein backbones in 3D for the motif-scaffolding problem, arXiv Preprint, available online at: https://arxiv.org/abs/2206.04119, 30 pages, (Mar. 20, 2023).
Yim, J. et al., Fast protein backbone generation with SE(3) flow matching, arXiv Preprint, available online at: https://arxiv.org/abs/2310.05297, 8 pages, (Oct. 10, 2023).
Zhang, Y. and Skolnick, J., Scoring function for automated assessment of protein structure template quality, Proteins, 57(4):702-710 (2004).
Lipman, Y. et al., Flow Matching for Generative Modeling, arXiv Preprint, available online at <https://arxiv.org/abs/2210.02747v1>, 24 pages, (Oct. 6, 2022).
Vaswani, A. et al., Attention Is All You Need, arXiv Preprint, available online at https://arxiv.org/abs/1706.03762, 15 pages, (Dec. 6, 2017).
Anand, N. et al., Fully differentiable full-atom protein backbone generation, ICLR 2019 Workshop: Deep Generative Models for Highly Structured Data, 10 pages, (2019).
Andrusier, N. et al., Principles of flexible protein-protein docking, Proteins, 73(2):271-289 (2008).
Gray, J.J. et al., Protein-protein docking with simultaneous optimization of rigid-body displacement and side-chain conformations, J. Mol. Biol., 331(1):281-299 (2003).
Huang, S.Y., Search strategies and evaluation in protein-protein docking: principles, advances and challenges, Drug Discov. Today, 19(8):1081-1096 (2014).
Meng, X.Y. et al., Molecular docking: a powerful approach for structure-based drug discovery, Curr. Comput. Aided Drug Des., 7(2):146-157 (2011).
Zhou, P. et al., Computational peptidology: a new and promising approach to therapeutic peptide design, Curr. Med. Chem., 20(15):1985-1996 (2013).
Ashtawy, Hossam Mohamed Farg., A Comparative Study of Machine-learning-based Scoring Functions in Predicting Protein-ligand Binding Affinity. Michigan State University. Electrical Engineering, 149 pages, (2011).
Cao, L. et al., De novo design of picomolar SARS-COV-2 miniprotein inhibitors, Science, 370(6515):426-431, (2020).
Chevalier, A., et al., Massively parallel de novo protein design for targeted therapeutics, Nature 550:74-79, (2017).
Collaborative Computational Project, No. 4, The CCP4 Suite: Programs for Protein Crystallography, Acta Crystallogr D Biol Crystallogr. D50:760-763 (1994).
Dauparas, J. et al., Robust deep learning based protein sequence design using ProteinMPNN, bioRxiv preprint, 33 pages, (2022).
Dhariwal, P. and Nichol, A., Diffusion models beat GANs on image synthesis, arXiv preprint, 44 pages, (2021).
Gainza, P. et al., De novo design of site-specific protein interactions with learned surface fingerprints, bioRxiv preprint, 41 pages, (2022).
Gainza, P. et al., Deciphering interaction fingerprints from protein molecular surfaces using geometric deep learning, Nat. Methods, 17(2):184-192 (2020).
Gorski, K.M., et al., HEALPix—a Framework for high resolution discretization, and fast analysis of data distributed on the sphere, 622:759-771, (2005).
Hassan-Harrirou, H., et al., RosENet: Improving Binding Affinity Prediction by Leveraging Molecular Mechanics Energies with an Ensemble of 3D Convolutional Neural Networks, J. Chem. Inf. Model, 60(6):2791-2802, (2020).
Hsu, C. et al., Learning inverse folding from millions of predicted structures, bioRxiv preprint, 22 pages, (2022).
Ingraham, J. et al., Generative Models for Graph-Based Protein Design, 33rd Conference on Neural Information Processing Systems (NeurIPS 2019), Vancouver, Canada, 12 pages, (2019). Retrieved online at: <https://proceedings.neurips.cc/paper/2019/hash/f3a4ff4839c56a5f460c88cce3666a2b-Abstract.html>.
International Search Report for PCT/US2022/038014, filed Jul. 22, 2022, 4 pages, (mailed Nov. 15, 2022).
Jiménez, J. et al., KDEEP: Protein-Ligand Absolute Binding Affinity Prediction via 3D-Convolutional Neural Networks, J. Chem. Inf. Model, 58(2):287-296, (2018).
Liu, Y. et al., Rotamer-free protein sequence design based on deep learning and self-consistency, Nature Computational Science, 19 pages, (2022).
Mcpartlon, M. et al., A deep SE(3)-equivariant model for learning inverse protein folding, bioRxiv preprint, 18 pages, (2022).
Pierce, B.G., et.al., Accelerating Protein Docking in ZDOCK Using an Advanced 3D Convolution Library, PLoS ONE, e24657, 6(9):1-6, (2011).
Ragoza, M. et al., Protein-Ligand Scoring with Convolutional Neural Networks, J. Chem. Inf. Model, 57(4):942-957, (2017).
Satorras, V.G. et al., E(n) Equivariant Graph Neural Networks, Proc. 38th Int. Conf. Machine Learning, PMLR, 139, 10 pages, (2021).
Senior, A.W. et al., Protein structure prediction using multiple deep neural networks in the 13th Critical Assessment of Protein Structure Prediction (CASP13), Proteins, 87(12):1141-1148 (2019).
Shapovalov, M.S., and Dunbrack, R.L., Jr., A smoothed backbone-dependent rotamer library for proteins derived from adaptive kernel density estimates and regressions, Structure, 19(6):844-858, <https://www.cell.com/structure/fulltext/S0969-2126(11)00144-4> (2011).
Shrake, A. and Rupley, J.A., Environment and exposure to solvent of protein atoms. Lysozyme and insulin, J. Mol. Biol., 79(2):351-371 (1973).
Strokach, A. et al., Fast and Flexible Protein Design Using Deep Graph Neural Networks, Cell Syst., 11(4):402-411, (2020).
The CCP4 Suite, Computer programs for protein crystallography, Overview and Manual, 130 pages, Feb. 2006.
Tien, M.Z. et al., Maximum allowed solvent accessibilites of residues in proteins, PLoS One, 8(11):e80635 (2013), 8 pages.
Wallach, I., et al., AtomNet: A Deep Convolutional Neural Network for Bioactivity Prediction in Structure-based Drug Discovery, 1-11, (2015).
Winn, M.D., et al., Overview of the CCP4 suite and current developments, Acta Crystallogr. Section D, Biological Crystallography, ISSN 0907-4449, D67:235-242, (2011).
Written Opinion for PCT/US2022/038014, filed Jul. 22, 2022, 8 pages, (mailed Nov. 15, 2022).
Yang, J. et al., Improved protein structure prediction using predicted interresidue orientations, Proc. Natl. Acad. Sci. USA, 117(3):1496-1503, (2020).
Yang, K. et al., Masked inverse folding with sequence transfer for protein representation learning, bioRxiv preprint, 16 pages, (2022).
Yershova, A., et al., Generating uniform incremental grids on SO(3) Using the Hopf Fibration, The Internation Journal of Robotics Research, 29:(7):801-812, (2010).
Zhang, Z. et al., Protein representation learning by geometric structure pretraining, arXiv preprint, 25 pages, (2022).
Lim, J. et al., Scaffold-based molecular design with a graph generative model, arXiv:1905.1369, 33 pages, (2019).

(56) References Cited

OTHER PUBLICATIONS

Lim, J. et al., Scaffold-based molecular design with a graph generative model, Chem. Sci., 11(4):1153-1164 (2020).

Anand, N. et al., Protein Sequence Design With A Learned Potential, bioRxiv 2020.01.06.895466; 23 pages, (2020), doi: https://doi.org/10.1101/2020.01.06.895466.

Abdin, O. et al., PepNN: a deep attention model for the identification of peptide binding sites, Commun. Biol., 5(1):503 (2022).

Anand, N. and Achim, T., Protein Structure and Sequence Generation with Equivariant Denoising Diffusion Probabilistic Models, arXiv preprint, 18 pages, (2022), retrieved online at: https://arxiv.org/pdf/2205.15019.pdf.

Anand, N. and Huang, P., Generative modeling for protein structures, Advances in Neural Information Processing Systems 31 (NeurIPS 2018), 12 pages, (2018).

Bennett, N.R. et al., Atomically accurate de novo design of single-domain antibodies, bioRxiv preprint, 30 pages, (2024), retrieved online at: https://www.biorxiv.org/content/10.1101/2024.03.14.585103v1.full.pdf.

Campbell, A. et al., Generative Flows on Discrete State-Spaces: Enabling Multimodal Flows with Applications to Protein Co-Design, arXiv preprint, 52 pages, (2024), retrieved online at: https://arxiv.org/abs/2402.04997.

Jing, B. et al., AlphaFold Meets Flow Matching for Generating Protein Ensembles, arXiv preprint, 26 pages, (2024), retrieved online at: https://arxiv.org/abs/2402.04845.

Lei, Y. et al., A deep-learning framework for multi-level peptide-protein interaction prediction, Nat. Commun., 12(1):5465 (2021).

Lin, Y. and Alquraishi, M., Generating Novel, Designable, and Diverse Protein Structures by Equivariantly Diffusing Oriented Residue Clouds, arXiv preprint, 25 pages, (2023), retrieved online at: https://arxiv.org/pdf/2301.12485.pdf.

Liu, X., Implementation of structural bioinformatics in thromboinflammation studies, Maastricht University Doctoral Thesis, 161 pages, (2021).

Mcpartlon, M. and Xu, J., An end-to-end deep learning method for rotamer-free protein side-chain packing, bioRxiv preprint, 29 pages, (2022), retrieved online at: https://www.biorxiv.org/content/10.1101/2022.03.11.483812v1.

Meli, R. et al., Scoring Functions for Protein-Ligand Binding Affinity Prediction using Structure-Based Deep Learning: A Review, Front. Bioinform., 2:885983 (2022).

Shi, W. et al., Graphsite: Ligand-binding site classification using Deep Graph Neural Network, bioRxiv preprint, 13 pages, (2021), retrieved online at: https://www.biorxiv.org/content/10.1101/2021.12.06.471420v1.full.pdf.

Stark, H. et al., Dirichlet Flow Matching with Applications to DNA Sequence Design, arXiv preprint, 19 pages, (2024), retrieved online at: https://arxiv.org/abs/2402.05841.

Van Hall-Beauvais, A.K., De novo designed proteins: a study in engineering novel folds and functions, 183 pages, (2023).

Wang, C. et al., Proteus: pioneering protein structure generation for enhanced designability and efficiency, bioRxiv preprint, 13 pages, (2024), retrieved online at: https://www.biorxiv.org/content/10.1101/2024.02.10.579791v1.full.pdf.

Watson, J.L. et al., De novo design of protein structure and function with RFdiffusion, Nature, 620(7976):1089-1100 (2023).

Yim, J. et al., Improved motif-scaffolding with SE(3) flow matching, arXiv preprint, 22 pages, (2024), retrieved online at: https://arxiv.org/abs/2401.04082.

Yim, J. et al., SE(3) diffusion model with application to protein backbone generation, arXiv preprint, 39 pages, (2023), retrieved online at: https://arxiv.org/abs/2302.02277.

Zhang, Y. et al., DiffPack: A Torsional Diffusion Model for Autoregressive Protein Side-Chain Packing, 37th Conference on Neural Information Processing Systems (NeurIPS 2023), 23 pages, (submitted Jun. 1, 2023, revised Feb. 16, 2024), retrieved online at: https://arxiv.org/abs/2306.01794.

\* cited by examiner

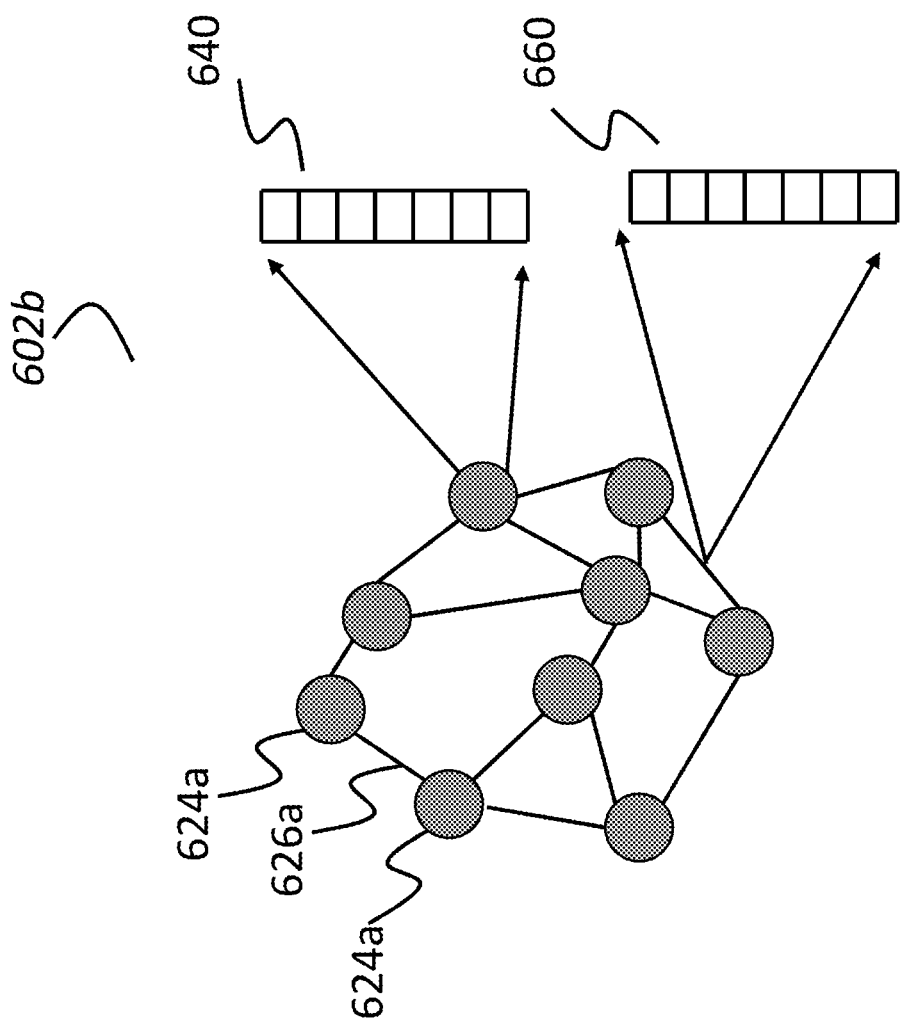
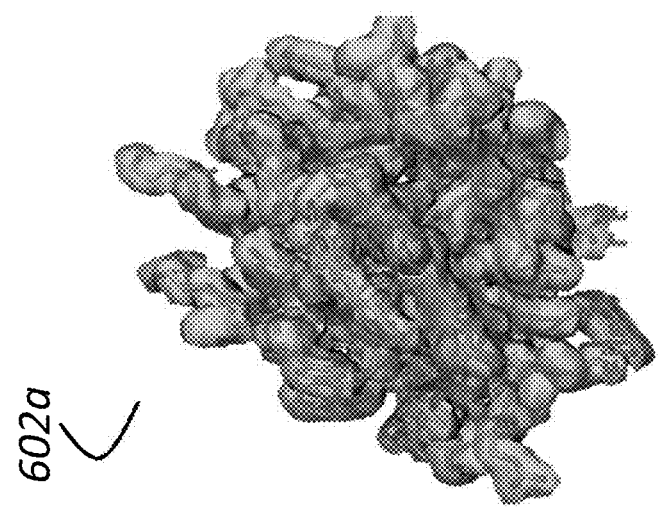
FIG. 6B
FIG. 6A

SYSTEMS AND METHODS FOR ARTIFICIAL INTELLIGENCE-BASED BINDING SITE PREDICTION AND SEARCH SPACE FILTERING FOR BIOLOGICAL SCAFFOLD DESIGN

BACKGROUND

An increasing number of important drugs and vaccines are complex biomolecules referred to as biologics. For example, seven of the top ten best selling drugs as of early 2020 were biologics, including the monoclonal antibody adalimumab (Humira®). Biologics have much more complex structure than traditional small molecule drugs. The process of drug discovery, drug development, and clinical trials requires an enormous amount of capital and time. Typically, new drug candidates undergo in vitro testing, in vivo testing, then clinical trials prior to approval.

Software tools for in-silico design and testing of new drug candidates can cut the cost and time of the preclinical pipeline. However, biologics often have hard-to-predict properties and molecular behavior. To date, despite recent interest in software and computational tools (including artificial intelligence (AI) and machine learning) relating to biological molecules, the extraordinary complexity of biologics continues to challenge computational tools aiming to produce accurate predictions for biologics and advances are needed.

SUMMARY

Presented herein are systems and methods for predicting which amino acid sites of target proteins of interest are binding sites—for example, locations and/or identifications of particular amino acid sites—that are amenable or likely to participate in binding interactions with other ligands, such as other proteins. These binding site predictions may, for example, be generated for target proteins that are implicated in disease and, accordingly, be targets for potential new biologic drugs. Binding site prediction technologies described herein may thus be used to guide design and/or testing of new and/or custom biologic drugs, either experimentally or in-silico.

In certain embodiments, binding site predictions as described herein may be valuable outputs in and of themselves. Among other things, they may facilitate understanding behaviors of proteins of interest, guide drug research and candidate selection, and speed biologic development. Additionally or alternatively, in certain embodiments, binding site predictions may be used in combination with other software modules, for example to improve quality and computational efficiency. For example, binding site predictions may be generated within and/or accessed by one or more artificial intelligence (AI) modules used for in-silico design of custom biologics, including, but are not limited to, those described in U.S. Pat. No. 11,450,407, entitled "Systems and Methods for Artificial Intelligence-Guided Biomolecule Design and Assessment," issued Sep. 20, 2022, and U.S. patent application Ser. No. 17/871,425, entitled, "Systems and Methods for Artificial Intelligence-Based Prediction of Amino Acid Sequences at a Binding Interface," filed Jul. 22, 2022, and U.S. Provisional Application No. 63/359,732, entitled "Systems and Methods for Generative Neural Network-Based Design of Custom Biologics," filed Jul. 8, 2022, the content of each of which is hereby incorporated by reference herein in its entirety.

For example, binding site predictions may be used in connection with a scaffold docking method, whereby scaffold models are used to represent candidate peptide backbones, so they can be oriented at a variety of poses (e.g., three-dimensional orientations whereby a particular candidate peptide backbone is rotated and/or translated in three dimensions) with respect to a target and evaluated, via one or more computer implemented processes, to determine which candidate peptide backbones, poses, and/or combinations thereof (e.g., scaffold-pose combinations) are likely to be most favorable for binding to the target. Identified backbones and poses can then be used as building blocks for subsequent design of amino acid interface sequences, for example as scaffolds that are populated with various combinations of amino acid side chains, to design a custom biologic, e.g., in-silico, for binding to the target. Binding site predictions may be used in conjunction with this scaffold docking procedure to, among other things, refine a search space of prospective candidate peptide backbones and poses before they are evaluated, for example to condition generation of and/or favor selection of backbones and poses thereof that are determined to position portions of a potential backbone in proximity to likely binding sites of the target.

Not only can this approach enhance quality of identified backbones and poses thereof used to design custom biologics, but, among other things, it can also improve computation efficiency and speed. In particular, searching and evaluating an extensive landscape of scaffold-pose combinations can be a time consuming calculation, particularly when a machine learning model (or other computationally intensive calculation) is used as a scoring function to evaluate (e.g., score) each combination. In certain embodiments, binding site predictions can be used to filter a scaffold-pose landscape that is explored during a scaffold docking procedure, allowing computationally intensive steps to focus on a subset of potential backbones and poses that involve predicted or known binding sites on a target of interest.

In this manner, binding site prediction technologies of the present disclosure can facilitate design and/or testing of new biologic drugs, leading to new and improved candidates and/or improving, among other things, developmental efficiency, success rates of clinical trials, and time to market.

In one aspect, the present disclosure is directed to a method for designing, in-silico, a custom biologic structure (e.g., a de-novo custom biologic structure) for binding to a target comprising one or more proteins [e.g., a single, monomeric protein (e.g., and/or a target peptide); e.g., a multimeric complex comprising two or more proteins (e.g., a dimer) (e.g., two or more distinct protein sub-units (e.g., a heterodimer, heterotrimer, etc.); e.g., two or more identical sub-units (e.g., a homodimer, homotrimer, etc.))], the method comprising: (a) receiving (e.g., and/or accessing), by a processor of a computing device, a target model representing at least a portion of the target; (b) determining, by the processor, a binding site prediction to identify each of one or more binding sites within the portion of the target (e.g., protein) represented by the target model, said one or more binding sites representing a region of the target (e.g., protein) identified (e.g., by a first machine learning model) as a likely interaction site for binding with another protein and/or peptide (e.g., a protein-protein interaction site; e.g., a ligand binding pocket); (c) receiving (e.g., and/or accessing), by the processor, one or more candidate scaffold model(s), each a representation of at least a portion of a candidate peptide backbone (e.g., a prospective backbone of the custom biologic structure being designed); (d) using the binding site prediction, the one or more candidate scaffold model(s), and the target model to generate, by the processor, one or more (e.g., a plurality of) prospective scaffold-target complex model(s), each representing at least a portion of a complex comprising a particular candidate peptide backbone [e.g., or a variation thereof (e.g., to account for backbone flexibility)], as represented by a particular one of the one or more candidate scaffold model(s), oriented at a particular pose (e.g., three-dimensional relative position and/or rotation) with respect to the target; (e) determining, by the processor, using a machine learning model (e.g., a second machine learning model), a scaffold-pose score for each of the one or more prospective scaffold-target complex model(s) at each of the one or more poses, thereby determining one or more (e.g., a plurality of) scaffold-pose scores; (f) selecting, by the processor, a scaffold-target complex model of the one or more prospective scaffold-target complex model(s) using (e.g., based on) the determined one or more scaffold-pose score(s) (e.g., thereby identifying a selected candidate peptide backbone, oriented at a selected pose on which to build a custom interface portion of a ligand for binding to the target); and (g) providing, by the processor, the selected scaffold-target complex model for use in designing the custom biologic structure for binding to the target.

In certain embodiments, step (b) comprises using a first machine learning model to generate the binding site prediction. In certain embodiments, the first machine learning model is or comprises a graph neural network.

In certain embodiments, the target model is or comprises a representation of the portion of the target in isolation, not bound to other binding partners (e.g., other proteins) in complex [e.g., wherein the target is a monomer, comprising a single target protein sub-unit and the target model comprises (e.g., solely) a representation of at least a portion of the target protein, e.g., and no other proteins; e.g., wherein the target is a dimer (e.g., a heterodimer; e.g., a homodimer), comprising two target proteins bound together in complex, and the target model comprises (e.g., solely) a representation of at least a portion of one or both of the two target proteins, e.g., but no other proteins; e.g., wherein the target is a multimer, comprising a plurality of target proteins bound together in complex, and the target model comprises (e.g., solely) a representation of at least a portion of the complex comprising the one or more target proteins, e.g., but no other proteins)].

In certain embodiments, the target model is or comprises (e.g., solely) representations of at least a portion of one or more members selected from the group consisting of: a monomer; a dimer; a trimer; a multimer (e.g., comprising two or more sub-units).

In certain embodiments, the target model is or comprises a target graph that represents the target via a graph representation (e.g., a plurality of nodes and, optionally, edges).

In certain embodiments, the target graph comprises a plurality of target nodes, each representing a particular (amino acid) site of the portion of the target (and/or peptide) and having a corresponding node feature vector comprising one or more constituent vectors (e.g., a plurality of concatenated constituent vectors), each constituent vector representing a particular (e.g., physical; e.g., structural) feature of the particular (amino acid) site.

In certain embodiments, each of the target nodes has a node feature vector comprising an amino acid type constituent vector that represents a particular type of amino acid (e.g., via a one hot encoding scheme).

In certain embodiments, each of the target nodes has a node feature vector comprising one or more constituent vectors selected from the group consisting of: a local backbone geometry [e.g., representing three torsional angles of backbone atoms (e.g., using two elements for—a sine and a cosine of—each angle)]; a measure of solvent exposed surface area; a curvature and/or convexity [e.g., one or more values representing a three-dimensional curvature of a region about a particular (amino acid) site]; a constituent vector that represents an amino acid property and/or classification [e.g., a classification of an amino acid as one or more of positively charged, negatively charged, polar, and hydrophobic/hydrophobicity (e.g., hydrophobic aliphatic; e.g., hydrophobic aromatic), e.g., at a particular (e.g., physiological) pH]; and a positional encoding [e.g., a vector and/or value indicating a position of the corresponding amino acid in a sequence of the target (e.g., an integer, e.g., 1, 2, 3, 4, etc.)].

In certain embodiments, the target graph comprises a plurality of edges, each associated with two particular nodes and having a corresponding edge feature vector comprising one or more constituent vectors representing a relative orientation of, and/or distance between, two (amino acid) sites represented by the two particular nodes.

In certain embodiments, the node feature vectors and/or edge feature vectors of the target graph are invariant with respect to three-dimensional translation and/or rotation of the target. In certain embodiments, for each node feature vector of a target node, at least a subset of the one or more constituent vectors comprise absolute coordinate values (e.g., on a particular coordinate frame) of one or more atoms (e.g., backbone atoms; e.g., a beta carbon atom) of the particular (amino acid) site represented by the target node.

In certain embodiments, the method further comprises: receiving (e.g., and/or accessing), by the processor, an initial representation of the target and generating, by the processor, the target graph from the initial representation.

In certain embodiments, the binding site prediction comprises, for each particular (amino acid) site of the portion of the target, a corresponding likelihood value that represents a likelihood that the particular site is or could be involved in a binding interaction with another protein and/or peptide.

In certain embodiments, the binding site prediction comprises, for each particular (amino acid) site of the portion of the target, a corresponding likelihood value that represents a likelihood of the particular site being a hotspot in a complex formed between the target and one or more other proteins (e.g., a likelihood of the particular site being located within a threshold distance of one or more sites of other member proteins of the complex).

In certain embodiments, the first machine learning model receives the target model (e.g., target graph) as input and generates, as output, a set of likelihood values comprising, for each particular (amino acid) site of the portion of the target, a corresponding likelihood value that represents a likelihood of the particular site being a hotspot.

In certain embodiments, each of the one or more candidate scaffold model(s) represents the candidate peptide backbone using a scaffold model that identifies types and locations of peptide backbone atoms while omitting (e.g., one or more) amino-acid side chain atoms (e.g., all but a first side chain atom, such as a beta-carbon or hydrogen (e.g., in the case of Glycine)).

In certain embodiments, step (d) comprises: generating, by the processor, a plurality of pose transformations [e.g., each pose transformation representing a three-dimensional rotation and/or translation operation) and determining, for each particular pose transformation of the plurality of generated pose transformations, a corresponding binding site involvement score based on the particular pose transformation, the binding site prediction, and the scaffold model, thereby determining a plurality of pose transformations along with a plurality of corresponding binding site involvement scores (e.g., a plurality of pose vectors, each representing a 3D rotation and/or translation together with, for each pose vector, a corresponding binding site involvement score); and filtering the plurality pose transformations based at least in part on the plurality of corresponding binding site involvement scores to obtain a filtered pose landscape.

In certain embodiments, the method comprises generating the one or more prospective scaffold-target complex model(s) and/or representations thereof according to the filtered pose landscape.

In certain embodiments, the binding site involvement score comprises a measure of whether a particular scaffold-target complex model, in which the candidate peptide backbone is oriented with respect to the target according to a particular pose, places at least a portion of (e.g., one or more atoms and/or side chains) the candidate peptide backbone in proximity to the one or more binding sites.

In certain embodiments, the second machine learning model is or comprises a convolutional neural network (CNN) and/or GNN [e.g., a deep neural network, comprising at least one (e.g., a plurality of) hidden layer(s)].

In certain embodiments, for each particular one of the one or more prospective scaffold-target complex model(s), the second machine learning model receives, as input, a representation (e.g., a volumetric representation; e.g., a graph representation) of the particular scaffold-target complex model and generates the scaffold-pose score for the particular scaffold-target complex model as output.

In certain embodiments, the scaffold-pose score of the particular scaffold target complex model is or comprises a value representing a measure of plausibility that the particular prospective scaffold-target complex model represents a native complex [e.g., as determined by the second machine learning model (e.g., via inference, based on prior training to distinguish representations of native complexes from representations of artificial complexes)].

In certain embodiments, the method further comprises: (i) generating, by the processor, based on the selected scaffold-target complex model, one or more prospective ligand models, each representing a prospective ligand for binding to the target (e.g., protein and/or peptide) by populating at least an interface region of the selected candidate backbone located in proximity to the target with amino acids.

In another aspect, the present disclosure is directed to a method for identifying one or more prospective binding sites on a target comprising one or more proteins [e.g., a single, monomeric protein (e.g., and/or a target peptide); e.g., a multimeric complex comprising two or more proteins (e.g., a dimer) (e.g., two or more distinct protein sub-units (e.g., a heterodimer, heterotrimer, etc.); e.g., two or more identical sub-units (e.g., a homodimer, homotrimer, etc.))], the method comprising: (a) obtaining (e.g., receiving, accessing, or generating), by a processor of a computing device, a target graph representing at least a portion of the target, the target graph comprising a plurality of target nodes, each corresponding to and representing a particular (amino acid) site of the portion of the target and having an associated node feature vector comprising one or more constituent feature vectors representing features (e.g., physical and/or chemical and/or structural) of the particular amino acid site; (b) generating, by the processor, using a machine learning model, a likelihood graph based on the target graph, wherein the machine learning model: receives at least the target graph as input; and generates, as output, the likelihood graph, wherein the likelihood graph comprises, for each of at least a portion of the target nodes of the target graph, a corresponding likelihood that a (amino acid) site represented by the target node is or could be involved in a binding interaction with another protein and/or peptide (e.g., would be a hotspot were the target to bind with another protein to form a biological complex); and (c) determining, by the processor, based on the likelihood graph, an identification of one or more binding sites, each representing a (amino acid) site of the target likely to influence {e.g., satisfy one or more criteria (e.g., same criteria (e.g., located within a threshold distance from one or more sites on another protein, e.g., having a surface accessibility measure above a particular threshold value) as used to identify binding sites for training examples that were used to train the machine learning model) used to identify binding sites} binding with another protein (e.g., would be a hotspot were the target to bind with another protein to form a biological complex).

In certain embodiments, the method comprises providing, by the processor, the identification of the one or more binding sites for use in designing a custom biologic.

In certain embodiments, the target graph is or comprises a representation of the portion of the target in isolation, not bound to other binding partners (e.g., other proteins) in complex [e.g., wherein the target is a monomer, comprising a single target protein sub-unit and the target graph comprises (e.g., solely) a representation of at least a portion of the target protein, e.g., and no other proteins; e.g., wherein the target is a dimer (e.g., a heterodimer; e.g., a homodimer), comprising two target proteins bound together in complex, and the target graph comprises (e.g., solely) a representation of at least a portion of one or both of the two target proteins, e.g., but no other proteins; e.g., wherein the target is a multimer, comprising a plurality of target proteins bound together in complex, and the target graph comprises (e.g., solely) a representation of at a portion of the complex comprising the one or more target proteins, e.g., but no other proteins)].

In certain embodiments, the target graph is or comprises (e.g., solely) a representation of at least a portion of one or more members selected from the group consisting of: a monomer; a dimer; a trimer; a multimer (e.g., comprising two or more sub-units).

In certain embodiments, each of the target nodes has a node feature vector comprising an amino acid type constituent vector that represents a particular type of amino acid (e.g., via a one hot encoding scheme).

In certain embodiments, each of the target nodes has a node feature vector comprising one or more constituent vectors selected from the group consisting of: a local backbone geometry [e.g., representing three torsional angles of backbone atoms (e.g., using two elements for—a sine and a cosine of—each angle)]; a measure of solvent exposed surface area; a curvature and/or convexity [e.g., one or more values representing a three-dimensional curvature of a region about a particular (amino acid) site]; a constituent vector that represents an amino acid property and/or classification [e.g., a classification of an amino acid as one or more of positively charged, negatively charged, polar, and hydrophobic/hydrophobicity (e.g., hydrophobic aliphatic; e.g., hydrophobic aromatic), e.g., at a particular (e.g., physiological) pH]; and a positional encoding [e.g., a vector and/or value indicating a position of the corresponding amino acid in a sequence of the target (e.g., an integer, e.g., 1, 2, 3, 4, etc.)].

In certain embodiments, the target graph comprises a plurality of edges, each associated with two particular nodes and having a corresponding edge feature vector comprising one or more constituent vectors representing a relative orientation of, and/or distance between, two (amino acid) sites represented by the two particular nodes.

In certain embodiments, the node feature vectors and/or edge feature vectors of the target graph are invariant with respect to three-dimensional translation and/or rotation of the target.

In certain embodiments, for each node feature vector of a target node, at least a subset of the one or more constituent vectors comprise absolute coordinate values (e.g., on a particular coordinate frame) of one or more atoms (e.g., backbone atoms; e.g., a beta carbon atom) of the particular (amino acid) site represented by the target node.

In certain embodiments, the method further comprises: receiving (e.g., and/or accessing), by the processor, an initial representation of the target and generating, by the processor, the target graph from the initial representation.

In another aspect, the invention is directed to a system for designing, in-silico, a custom biologic structure (e.g., a de-novo custom biologic structure) for binding to a target comprising one or more proteins [e.g., a single, monomeric protein (e.g., and/or a target peptide); e.g., a multimeric complex comprising two or more proteins (e.g., a dimer) (e.g., two or more distinct protein sub-units (e.g., a heterodimer, heterotrimer, etc.); e.g., two or more identical sub-units (e.g., a homodimer, homotrimer, etc.))], the system comprising: a processor of a computing device; and a memory having instructions stored thereon, wherein the instructions, when executed by the processor cause the processor to: (a) receive (e.g., and/or access) a target model representing at least a portion of the target; (b) determine a binding site prediction to identify each of one or more binding sites within the portion of the target (e.g., protein) represented by the target model, said one or more binding sites representing a region of the target (e.g., protein) identified (e.g., by a first machine learning model) as a likely interaction site for binding with another protein and/or peptide (e.g., a protein-protein interaction site; e.g., a ligand binding pocket); (c) receive (e.g., and/or access) one or more candidate scaffold model(s), each a representation of at least a portion of a candidate peptide backbone (e.g., a prospective backbone of the custom biologic structure being designed); (d) use the binding site prediction, the one or more candidate scaffold model(s), and the target model to generate one or more (e.g., a plurality of) prospective scaffold-target complex model(s), each representing at least a portion of a complex comprising a particular candidate peptide backbone [e.g., or a variation thereof (e.g., to account for backbone flexibility)], as represented by a particular one of the one or more candidate scaffold model(s), oriented at a particular pose (e.g., three-dimensional relative position and/or rotation) with respect to the target; (e) determine, using a machine learning model (e.g., a second machine learning model), a scaffold-pose score for each of the one or more prospective scaffold-target complex model(s) at each of the one or more poses, thereby determining one or more (e.g., a plurality of) scaffold-pose scores; (f) select a scaffold-target complex model of the one or more prospective scaffold-target complex model(s) using (e.g., based on) the determined one or more scaffold-pose score(s) (e.g., thereby identifying a selected candidate peptide backbone, oriented at a selected pose on which to build a custom interface portion of a ligand for binding to the target); and (g) provide the selected scaffold-target complex model for use in designing the custom biologic structure for binding to the target.

In certain embodiments, at step (b) the instructions cause the processor to use a first machine learning model to generate the binding site prediction.

In certain embodiments, the first machine learning model is or comprises a graph neural network.

In certain embodiments, the target model is or comprises a representation of the portion of the target in isolation, not bound to other binding partners (e.g., other proteins) in complex [e.g., wherein the target is a monomer, comprising a single target protein sub-unit and the target model comprises (e.g., solely) a representation of at least a portion of the target protein, e.g., and no other proteins; e.g., wherein the target is a dimer (e.g., a heterodimer; e.g., a homodimer), comprising two target proteins bound together in complex, and the target model comprises (e.g., solely) a representation of at least a portion of one or both of the two target proteins, e.g., but no other proteins; e.g., wherein the target is a multimer, comprising a plurality of target proteins bound together in complex, and the target model comprises (e.g., solely) a representation of at least a portion of the complex comprising the one or more target proteins, e.g., but no other proteins)].

In certain embodiments, the target model is or comprises (e.g., solely) representations of at least a portion of one or more members selected from the group consisting of: a monomer; a dimer; a trimer; a multimer (e.g., comprising two or more sub-units).

In certain embodiments, the target model is or comprises a target graph that represents the target via a graph representation (e.g., a plurality of nodes and, optionally, edges).

In certain embodiments, the target graph comprises a plurality of target nodes, each representing a particular (amino acid) site of the portion of the target (and/or peptide) and having a corresponding node feature vector comprising one or more constituent vectors (e.g., a plurality of concatenated constituent vectors), each constituent vector representing a particular (e.g., physical; e.g., structural) feature of the particular (amino acid) site.

In certain embodiments, each of the target nodes has a node feature vector comprising an amino acid type constituent vector that represents a particular type of amino acid (e.g., via a one hot encoding scheme).

In certain embodiments, each of the target nodes has a node feature vector comprising one or more constituent vectors selected from the group consisting of: a local backbone geometry [e.g., representing three torsional angles of backbone atoms (e.g., using two elements for—a sine and a cosine of—each angle)]; a measure of solvent exposed surface area; a curvature and/or convexity [e.g., one or more values representing a three-dimensional curvature of a region about a particular (amino acid) site]; a constituent vector that represents an amino acid property and/or classification [e.g., a classification of an amino acid as one or more of positively charged, negatively charged, polar, and hydrophobic/hydrophobicity (e.g., hydrophobic aliphatic; e.g., hydrophobic aromatic), e.g., at a particular (e.g., physiological) pH]; and a positional encoding [e.g., a vector and/or value indicating a position of the corresponding amino acid in a sequence of the target (e.g., an integer, e.g., 1, 2, 3, 4, etc.)].

In certain embodiments, the target graph comprises a plurality of edges, each associated with two particular nodes and having a corresponding edge feature vector comprising one or more constituent vectors representing a relative orientation of, and/or distance between, two (amino acid) sites represented by the two particular nodes.

In certain embodiments, the node feature vectors and/or edge feature vectors of the target graph are invariant with respect to three-dimensional translation and/or rotation of the target.

In certain embodiments, for each node feature vector of a target node, at least a subset of the one or more constituent vectors comprise absolute coordinate values (e.g., on a particular coordinate frame) of one or more atoms (e.g., backbone atoms; e.g., a beta carbon atom) of the particular (amino acid) site represented by the target node.

In certain embodiments, the instructions cause the processor to receive (e.g., and/or access) an initial representation of the target and generating, by the processor, the target graph from the initial representation.

In certain embodiments, the binding site prediction comprises, for each particular (amino acid) site of the portion of the target, a corresponding likelihood value that represents a likelihood that the particular site is or could be involved in a binding interaction with another protein and/or peptide.

In certain embodiments, the binding site prediction comprises, for each particular (amino acid) site of the portion of the target, a corresponding likelihood value that represents a likelihood of the particular site being a hotspot in a complex formed between the target and one or more other proteins (e.g., a likelihood of the particular site being located within a threshold distance of one or more sites of other member proteins of the complex).

In certain embodiments, the first machine learning model receives the target model (e.g., target graph) as input and generates, as output, a set of likelihood values comprising, for each particular (amino acid) site of the portion of the target, a corresponding likelihood value that represents a likelihood of the particular site being a hotspot.

In certain embodiments, the each of the one or more candidate scaffold model(s) represents the candidate peptide backbone using a scaffold model that identifies types and locations of peptide backbone atoms while omitting (e.g., one or more) amino-acid side chain atoms (e.g., all but a first side chain atom, such as a beta-carbon or hydrogen (e.g., in the case of Glycine)).

In certain embodiments, at step (d) the instructions cause the processor to: generate a plurality of pose transformations [e.g., each pose transformation representing a three-dimensional rotation and/or translation operation) and determine, for each particular pose transformation of the plurality of generated pose transformations, a corresponding binding site involvement score based on the particular pose transformation, the binding site prediction, and the scaffold model, thereby determining a plurality of pose transformations along with a plurality of corresponding binding site involvement scores (e.g., a plurality of pose vectors, each representing a 3D rotation and/or translation together with, for each pose vector, a corresponding binding site involvement score); and filter the plurality pose transformations based at least in part on the plurality of corresponding binding site involvement scores to obtain a filtered pose landscape.

In certain embodiments, the instructions cause the processor to generate the one or more prospective scaffold-target complex model(s) and/or representations thereof according to the filtered pose landscape.

In certain embodiments, the binding site involvement score comprises a measure of whether a particular scaffold-target complex model, in which the candidate peptide backbone is oriented with respect to the target according to a particular pose, places at least a portion of (e.g., one or more atoms and/or side chains) the candidate peptide backbone in proximity to the one or more binding sites.

In certain embodiments, the second machine learning model is or comprises a convolutional neural network (CNN) and/or GNN [e.g., a deep neural network, comprising at least one (e.g., a plurality of) hidden layer(s)].

In certain embodiments, for each particular one of the one or more prospective scaffold-target complex model(s), the second machine learning model receives, as input, a representation (e.g., a volumetric representation; e.g., a graph representation) of the particular scaffold-target complex model and generates the scaffold-pose score for the particular scaffold-target complex model as output.

In certain embodiments, the scaffold-pose score of the particular scaffold target complex model is or comprises a value representing a measure of plausibility that the particular prospective scaffold-target complex model represents a native complex [e.g., as determined by the second machine learning model (e.g., via inference, based on prior training to distinguish representations of native complexes from representations of artificial complexes)].

In certain embodiments, the instructions cause the processor to: (i) generate, based on the selected scaffold-target complex model, one or more prospective ligand models, each representing a prospective ligand for binding to the target protein (and/or peptide) by populating at least an interface region of the selected candidate backbone located in proximity to the target with amino acids.

In another aspect, the invention is directed to a system for identifying one or more prospective binding sites on a target comprising one or more proteins [e.g., a single, monomeric protein (e.g., and/or a target peptide); e.g., a multimeric complex comprising two or more proteins (e.g., a dimer) (e.g., two or more distinct protein sub-units (e.g., a heterodimer, heterotrimer, etc.); e.g., two or more identical sub-units (e.g., a homodimer, homotrimer, etc.))], the system comprising: a processor of a computing device; and a memory having instructions stored thereon, wherein the instructions, when executed by the processor, cause the processor to: (a) obtain (e.g., receive, access, or generate) a target graph representing at least a portion of the target, the target graph comprising a plurality of target nodes, each corresponding to and representing a particular (amino acid) site of the portion of the target and having an associated node feature vector comprising one or more constituent feature vectors representing features (e.g., physical and/or chemical) of the particular amino acid site; (b) generate, using a machine learning model, a likelihood graph based on the target graph, wherein the machine learning model: receives at least the target graph as input; and generates, as output, the likelihood graph, wherein the likelihood graph comprises, for each of at least a portion of the target nodes of the target graph, a corresponding likelihood that a (amino acid) site represented by the target node is or could be involved in a binding interaction with another protein and/or peptide (e.g., would be a hotspot were the target to bind with another protein to form a biological complex); and (c) determine, based on the likelihood graph, an identification of one or more binding sites, each representing a (amino acid) site of the target likely to influence binding with another protein.

In certain embodiments, the instructions cause the processor to provide the identification of the one or more binding sites for use in designing a custom biologic (e.g., for display and/or further processing).

In certain embodiments, the target graph is or comprises a representation of the portion of the target in isolation, not bound to other binding partners (e.g., other proteins) in complex [e.g., wherein the target is a monomer, comprising a single target protein sub-unit and the target graph comprises (e.g., solely) a representation of at least a portion of the target protein, e.g., and no other proteins; e.g., wherein the target is a dimer (e.g., a heterodimer; e.g., a homodimer), comprising two target proteins bound together in complex, and the target graph comprises (e.g., solely) a representation of at least a portion of one or both of the two target proteins, e.g., but no other proteins; e.g., wherein the target is a multimer, comprising a plurality of target proteins bound together in complex, and the target graph comprises (e.g., solely) a representation of at a portion of the complex comprising the one or more target proteins, e.g., but no other proteins)].

In certain embodiments, the target graph is or comprises (e.g., solely) a representation of at least a portion of one or more members selected from the group consisting of: a monomer; a dimer; a trimer; a multimer (e.g., comprising two or more sub-units).

In certain embodiments, each of the target nodes has a node feature vector comprising an amino acid type constituent vector that represents a particular type of amino acid (e.g., via a one hot encoding scheme).

In certain embodiments, each of the target nodes has a node feature vector comprising one or more constituent vectors selected from the group consisting of: a local backbone geometry [e.g., representing three torsional angles of backbone atoms (e.g., using two elements for—a sine and a cosine of—each angle)]; a measure of solvent exposed surface area; a curvature and/or convexity [e.g., one or more values representing a three-dimensional curvature of a region about a particular (amino acid) site]; a constituent vector that represents an amino acid property and/or classification [e.g., a classification of an amino acid as one or more of positively charged, negatively charged, polar, and hydrophobic/hydrophobicity (e.g., hydrophobic aliphatic; e.g., hydrophobic aromatic), e.g., at a particular (e.g., physiological) pH]; and a positional encoding [e.g., a vector and/or value indicating a position of the corresponding amino acid in a sequence of the target (e.g., an integer, e.g., 1, 2, 3, 4, etc.)].

In certain embodiments, the target graph comprises a plurality of edges, each associated with two particular nodes and having a corresponding edge feature vector comprising one or more constituent vectors representing a relative orientation of, and/or distance between, two (amino acid) sites represented by the two particular nodes.

In certain embodiments, the node feature vectors and/or edge feature vectors of the target graph are invariant with respect to three-dimensional translation and/or rotation of the target.

In certain embodiments, for each node feature vector of a target node, at least a subset of the one or more constituent vectors comprise absolute coordinate values (e.g., on a particular coordinate frame) of one or more atoms (e.g., backbone atoms; e.g., a beta carbon atom) of the particular (amino acid) site represented by the target node.

In certain embodiments, the instructions cause the processor to receive (e.g., and/or access) an initial representation of the target and generate the target graph from the initial representation.

Features of embodiments described with respect to one aspect of the invention may be applied with respect to another aspect of the invention.

BRIEF DESCRIPTION OF THE DRAWING

The foregoing and other objects, aspects, features, and advantages of the present disclosure will become more apparent and better understood by referring to the following description taken in conjunction with the accompanying drawings, in which:

FIG. 6A is a schematic showing a three-dimensional (3D) representation of a target structure, such as a target protein and/or peptide, according to an illustrative embodiment.

FIG. 6B is a diagram of a graph representation of a target structure, according to an illustrative embodiment.

Figure 1B:
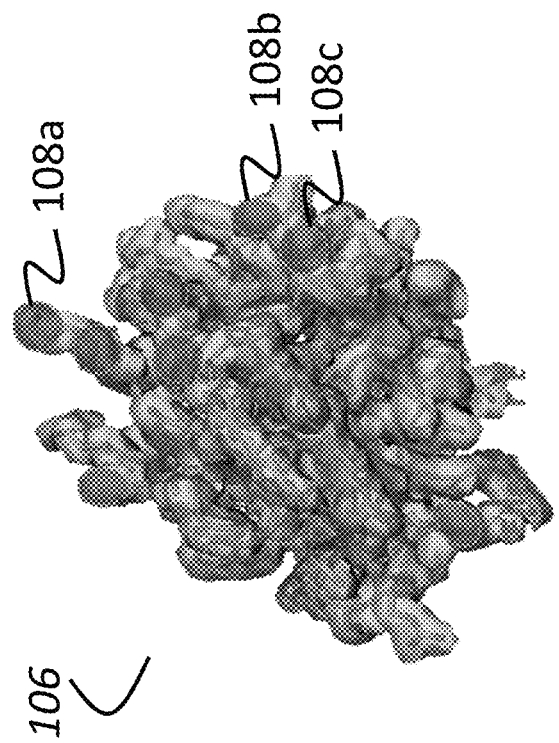
FIG. 1B is a schematic illustrating a binding site prediction, according to an illustrative embodiment.

Features and advantages of the present disclosure will become more apparent from the detailed description of certain embodiments that is set forth below, particularly when taken in conjunction with the figures, in which like reference characters identify corresponding elements throughout. In the figures, like reference numbers generally indicate identical, functionally similar, and/or structurally similar elements.

CERTAIN DEFINITIONS

In order for the present disclosure to be more readily understood, certain terms are first defined below. Additional definitions for the following terms and other terms are set forth throughout the specification.

Comprising: A device, composition, system, or method described herein as "comprising" one or more named elements or steps is open-ended, meaning that the named elements or steps are essential, but other elements or steps may be added within the scope of the composition or method. To avoid prolixity, it is also understood that any device, composition, or method described as "comprising" (or which "comprises") one or more named elements or steps also describes the corresponding, more limited composition or method "consisting essentially of" (or which "consists essentially of") the same named elements or steps, meaning that the composition or method includes the named essential elements or steps and may also include additional elements or steps that do not materially affect the basic and novel characteristic(s) of the composition or method. It is also understood that any device, composition, or method described herein as "comprising" or "consisting essentially of" one or more named elements or steps also describes the corresponding, more limited, and closed-ended composition or method "consisting of" (or "consists of") the named elements or steps to the exclusion of any other unnamed element or step. In any composition or method disclosed herein, known or disclosed equivalents of any named essential element or step may be substituted for that element or step.

A, an: As used herein, "a" or "an" with reference to a claim feature means "one or more," or "at least one."

Administration: As used herein, the term "administration" typically refers to the administration of a composition to a subject or system. Those of ordinary skill in the art will be aware of a variety of routes that may, in appropriate circumstances, be utilized for administration to a subject, for example a human. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc.), enteral, intra-arterial, intradermal, intragastric, intramedullary, intramuscular, intranasal, intraperitoneal, intrathecal, intravenous, intraventricular, within a specific organ (e.g., intrahepatic), mucosal, nasal, oral, rectal, subcutaneous, sublingual, topical, tracheal (e.g., by intratracheal instillation), vaginal, vitreal, etc. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Affinity: As is known in the art, "affinity" is a measure of the tightness with which two or more binding partners associate with one another. Those skilled in the art are aware of a variety of assays that can be used to assess affinity, and will furthermore be aware of appropriate controls for such assays. In some embodiments, affinity is assessed in a quantitative assay. In some embodiments, affinity is assessed over a plurality of concentrations (e.g., of one binding partner at a time). In some embodiments, affinity is assessed in the presence of one or more potential competitor entities (e.g., that might be present in a relevant—e.g., physiological—setting). In some embodiments, affinity is assessed relative to a reference (e.g., that has a known affinity above a particular threshold [a "positive control" reference] or that has a known affinity below a particular threshold [a "negative control" reference"]). In some embodiments, affinity may be assessed relative to a contemporaneous reference; in some embodiments, affinity may be assessed relative to a historical reference. Typically, when affinity is assessed relative to a reference, it is assessed under comparable conditions.

Amino acid: The term "amino acid," in its broadest sense, as used herein, refers to any compound and/or substance that can be incorporated into a polypeptide chain, e.g., through formation of one or more peptide bonds. In some embodiments, an amino acid has the general structure H$_2$N—C(H)(R)—COOH. In some embodiments, an amino acid is a naturally-occurring amino acid. In some embodiments, an amino acid is a non-natural amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. In some embodiments, an amino acid, including a carboxy- and/or amino-terminal amino acid in a polypeptide, can contain a structural modification as compared with the general structure above. For example, in some embodiments, an amino acid may be modified by methylation, amidation, acetylation, pegylation, glycosylation, phosphorylation, and/or substitution (e.g., of the amino group, the carboxylic acid group, one or more protons, and/or the hydroxyl group) as compared with the general structure. In some embodiments, such modification may, for example, alter the circulating half-life of a polypeptide containing the modified amino acid as compared with one containing an otherwise identical unmodified amino acid. In some embodiments, such modification does not significantly alter a relevant activity of a polypeptide containing the modified amino acid, as compared with one containing an otherwise identical unmodified amino acid. As will be clear from context, in some embodiments, the term "amino acid" may be used to refer to a free amino acid; in some embodiments it may be used to refer to an amino acid residue of a polypeptide.

Antibody, Antibody polypeptide: As used herein, the terms "antibody polypeptide" or "antibody", or "antigen-binding fragment thereof", which may be used interchangeably, refer to polypeptide(s) capable of binding to an epitope. In some embodiments, an antibody polypeptide is a full-length antibody, and in some embodiments, is less than full length but includes at least one binding site (comprising at least one, and preferably at least two sequences with structure of antibody "variable regions"). In some embodiments, the term "antibody polypeptide" encompasses any protein having a binding domain which is homologous or largely homologous to an immunoglobulin-binding domain. In particular embodiments, "antibody polypeptides" encompasses polypeptides having a binding domain that shows at least 99% identity with an immunoglobulin binding domain. In some embodiments, "antibody polypeptide" is any protein having a binding domain that shows at least 70%, 80%, 85%, 90%, or 95% identity with an immuglobulin binding domain, for example a reference immunoglobulin binding domain. An included "antibody polypeptide" may have an amino acid sequence identical to that of an antibody that is found in a natural source. Antibody polypeptides in accordance with the present invention may be prepared by any available means including, for example, isolation from a natural source or antibody library, recombinant production in or with a host system, chemical synthesis, etc., or combinations thereof. An antibody polypeptide may be monoclonal or polyclonal. An antibody polypeptide may be a member of any immunoglobulin class, including any of the human classes: IgG, IgM, IgA, IgD, and IgE. In certain embodiments, an antibody may be a member of the IgG immunoglobulin class. As used herein, the terms "antibody polypeptide" or "characteristic portion of an antibody" are used interchangeably and refer to any derivative of an antibody that possesses the ability to bind to an epitope of interest. In certain embodiments, the "antibody polypeptide" is an antibody fragment that retains at least a significant portion of the full-length antibody's specific binding ability. Examples of antibody fragments include, but are not limited to, Fab, Fab', F(ab')2, scFv, Fv, dsFv diabody, and Fd fragments. Alternatively or additionally, an antibody fragment may comprise multiple chains that are linked together, for example, by disulfide linkages. In some embodiments, an antibody polypeptide may be a human antibody. In some embodiments, the antibody polypeptides may be a humanized. Humanized antibody polypeptides include may be chimeric immunoglobulins, immunoglobulin chains or antibody polypeptides (such as Fv, Fab, Fab', F(ab')2 or other antigen-binding subsequences of antibodies) that contain minimal sequence derived from non-human immunoglobulin. In general, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Backbone, peptide backbone: As used herein, the term "backbone," for example, as in a backbone or a peptide or polypeptide, refers to the portion of the peptide or polypeptide chain that comprises the links between amino acid of the chain but excludes side chains. In other words, a backbone refers to the part of a peptide or polypeptide that would remain if side chains were removed. In certain embodiments, the backbone is a chain comprising a carboxyl group of one amino acid bound via a peptide bond to an amino group of a next amino acid, and so on. Backbone may also be referred to as "peptide backbone". It should be understood that, where the term "peptide backbone" is used, it is used for clarity, and is not intended to limit a length of a particular backbone. That is, the term "peptide backbone" may be used to describe a peptide backbone of a peptide and/or a protein.

Binding Site, Binding Patch: As used herein, the term "binding site," is used to refer to an individual (e.g., a single) amino acid site of a particular protein that has been determined and/or is predicted to interact with, and/or influence binding between the particular protein and, other molecules, such as other proteins. Accordingly, the term "binding site" is used herein to identify an individual, particular, amino acid site of a protein, rather than a group of multiple amino acids that are associated with binding from one protein to another or a region on a surface of a protein, defined spatially rather than with regard to one or more amino acids. Instead, the terms "binding patch," "patch of binding sites" are used to refer to sets of multiple amino acids that together are implicated in binding, or a spatial region on a surface of a protein that is implicated in binding. Individual amino acid sites that are within a binding patch or patch of binding sites may themselves be binding sites. As described in further detail herein, technologies of the present disclosure may generate a prediction, for example a probability value, that each of one or more amino acid sites of a particular target protein will be implicated in binding on an individualized, site-by-site, basis, thereby generating, for each individual amino acid site, a prediction of whether the individual site is a binding site. Individual amino acid sites may be labeled as binding sites or non-binding sites. In certain embodiments, predictions and/or classifications of whether one or more amino acid sites are binding sites may, in turn, be utilized to identify binding patches as, e.g., sets of amino acid sites or representations of 3D surface regions on a particular protein.

Biologic: As used herein, the term "biologic" refers to a composition that is or may be produced by recombinant DNA technologies, peptide synthesis, or purified from natural sources and that has a desired biological activity. A biologic can be, for example, a protein, peptide, glycoprotein, polysaccharide, a mixture of proteins or peptides, a mixture of glycoproteins, a mixture of polysaccharides, a mixture of one or more of a protein, peptide, glycoprotein or polysaccharide, or a derivatized form of any of the foregoing entities. Molecular weight of biologics can vary widely, from about 1000 Da for small peptides such as peptide hormones to one thousand kDa or more for complex polysaccharides, mucins, and other heavily glycosylated proteins. In certain embodiments, a biologic is a drug used for treatment of diseases and/or medical conditions. Examples of biologic drugs include, without limitation, native or engineered antibodies or antigen binding fragments thereof, and antibody-drug conjugates, which comprise an antibody or antigen binding fragments thereof conjugated directly or indirectly (e.g., via a linker) to a drug of interest, such as a cytotoxic drug or toxin. In certain embodiments, a biologic is a diagnostic, used to diagnose diseases and/or medical conditions. For example, allergen patch tests utilize biologics (e.g. biologics manufactured from natural substances) that are known to cause contact dermatitis. Diagnostic biologics may also include medical imaging agents, such as proteins that are labelled with agents that provide a detectable signal that facilitates imaging such as fluorescent markers, dyes, radionuclides, and the like.

In vitro: The term "in vitro" as used herein refers to events that occur in an artificial environment, e.g., in a test tube or reaction vessel, in cell culture, etc., rather than within a multi-cellular organism.

In vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Native, wild-type (WT): As used herein, the terms "native" and "wild-type" are used interchangeably to refer to biological structures and/or computer representations thereof that have been identified and demonstrated to exist in the physical, real world (e.g., as opposed to in computer abstractions). The terms, native and wild-type may refer to structures including naturally occurring biological structures, but do not necessarily require that a particular structure be naturally occurring. For example, the terms native and wild-type may also refer to structures including engineered structures that are man-made, and do not occur in nature, but have nonetheless been created and (e.g., experimentally) demonstrated to exist. In certain embodiments, the terms native and wild-type refer to structures that have been characterized experimentally, and for which an experimental determination of molecular structure (e.g., via x-ray crystallography) has been made.

Patient: As used herein, the term "patient" refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. In some embodiments, a patient is suffering from or susceptible to one or more disorders or conditions. In some embodiments, a patient displays one or more symptoms of a disorder or condition. In some embodiments, a patient has been diagnosed with one or more disorders or conditions. In some embodiments, the disorder or condition is or includes cancer, or presence of one or more tumors. In some embodiments, the patient is receiving or has received certain therapy to diagnose and/or to treat a disease, disorder, or condition.

Peptide: The term "peptide" as used herein refers to a polypeptide that is typically relatively short, for example having a length of less than about 100 amino acids, less than about 50 amino acids, less than about 40 amino acids less than about 30 amino acids, less than about 25 amino acids, less than about 20 amino acids, less than about 15 amino acids, or less than 10 amino acids.

Polypeptide: As used herein refers to a polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man. In some embodiments, a polypeptide may comprise or consist of natural amino acids, non-natural amino acids, or both. In some embodiments, a polypeptide may comprise or consist of only natural amino acids or only non-natural amino acids. In some embodiments, a polypeptide may comprise D-amino acids, L-amino acids, or both. In some embodiments, a polypeptide may comprise only D-amino acids. In some embodiments, a polypeptide may comprise only L-amino acids. In some embodiments, a polypeptide may include one or more pendant groups or other modifications, e.g., modifying or attached to one or more amino acid side chains, at the polypeptide's N-terminus, at the polypeptide's C-terminus, or any combination thereof. In some embodiments, such pendant groups or modifications may be selected from the group consisting of acetylation, amidation, lipidation, methylation, pegylation, etc., including combinations thereof. In some embodiments, a polypeptide may be cyclic, and/or may comprise a cyclic portion. In some embodiments, a polypeptide is not cyclic and/or does not comprise any cyclic portion. In some embodiments, a polypeptide is linear. In some embodiments, a polypeptide may be or comprise a stapled polypeptide. In some embodiments, the term "polypeptide" may be appended to a name of a reference polypeptide, activity, or structure; in such instances it is used herein to refer to polypeptides that share the relevant activity or structure and thus can be considered to be members of the same class or family of polypeptides. For each such class, the present specification provides and/or those skilled in the art will be aware of exemplary polypeptides within the class whose amino acid sequences and/or functions are known; in some embodiments, such exemplary polypeptides are reference polypeptides for the polypeptide class or family. In some embodiments, a member of a polypeptide class or family shows significant sequence homology or identity with, shares a common sequence motif (e.g., a characteristic sequence element) with, and/or shares a common activity (in some embodiments at a comparable level or within a designated range) with a reference polypeptide of the class; in some embodiments with all polypeptides within the class). For example, in some embodiments, a member polypeptide shows an overall degree of sequence homology or identity with a reference polypeptide that is at least about 30-40%, and is often greater than about 50%, 60%, 70%, 80%, 90%, 91%, 92%, 93%, 94%, 95%, 96%, 97%, 98%, 99% or more and/or includes at least one region (e.g., a conserved region that may in some embodiments be or comprise a characteristic sequence element) that shows very high sequence identity, often greater than 90% or even 95%, 96%, 97%, 98%, or 99%. Such a conserved region usually encompasses at least 3-4 and often up to 20 or more amino acids; in some embodiments, a conserved region encompasses at least one stretch of at least 2, 3, 4, 5, 6, 7, 8, 9, 10, 11, 12, 13, 14, 15 or more contiguous amino acids. In some embodiments, a relevant polypeptide may comprise or consist of a fragment of a parent polypeptide. In some embodiments, a useful polypeptide as may comprise or consist of a plurality of fragments, each of which is found in the same parent polypeptide in a different spatial arrangement relative to one another than is found in the polypeptide of interest (e.g., fragments that are directly linked in the parent may be spatially separated in the polypeptide of interest or vice versa, and/or fragments may be present in a different order in the polypeptide of interest than in the parent), so that the polypeptide of interest is a derivative of its parent polypeptide.

Pose: As used herein, the term "pose" refers to a relative three-dimensional rotation and/or translation of one object, such as a polypeptide chain (e.g., protein) or peptide backbone thereof (e.g., represented by a scaffold model), with respect to another, such as a target molecule, e.g., a target protein. Accordingly, as used herein, for example in the context of molecular binding, where a particular protein and/or peptide backbone (e.g., a candidate peptide backbone) is referred to and/or described as being oriented at or according to a particular pose with respect to another protein (e.g., a target protein), it should be understood that the particular protein and/or peptide backbone may be rotated and/or translated in three dimensions relative to the other protein (e.g., target protein). A variety of manners and approaches may be used for representing poses, which may, for example, include representing rotations and/or transformations relative to a reference, such as the target and/or an initial pose of a scaffold representation, using one or more fixed coordinate systems, etc. For example, in certain embodiments, a particular pose may be represented as a combination one or more rotations and/or translations in three-dimensional space, relative to a particular, reference object (e.g., such as a target protein) or coordinate (e.g., a location at or within a target protein representation), such as values of three rotational angles and/or three distances/angles defining a 3D translation (e.g., defined in a particular coordinate system, such as rectangular, cylindrical, spherical). In certain embodiments, a target and a scaffold model may be represented in a particular coordinate system, with the scaffold model oriented with respect to the target at a particular initial pose. Additional poses may then be represented relative to the initial pose, for example as relative translations and/or rotations (in three dimensions) with respect to the initial pose.

Protein: As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

Target: As used herein, the terms "target," and "receptor" are used interchangeably and refer to one or more molecules or portions thereof to which a binding agent—e.g., a custom biologic, such as a protein or peptide, to be designed—binds. In certain embodiments, the target is or comprises a protein and/or peptide. In certain embodiments, the target is a molecule, such as an individual protein or peptide (e.g., a protein or peptide monomer), or portion thereof. In certain embodiments, the target is a complex, such as a complex of two or more proteins or peptides, for example, a macromolecular complex formed by two or more protein or peptide monomers. For example, a target may be a protein or peptide dimer, trimer, tetramer, etc. or other oligomeric complex. In certain embodiments, the target is a drug target, e.g., a molecule in the body, usually a protein, that is intrinsically associated with a particular disease process and that could be addressed by a drug to produce a desired therapeutic effect. In certain embodiments, a custom biologic is engineered to bind to a particular target. While the structure of the target remains fixed, structural features of the custom biologic may be varied to allow it to bind (e.g., at high specificity) to the target.

Treat: As used herein, the term "treat" (also "treatment" or "treating") refers to any administration of a therapeutic agent (also "therapy") that partially or completely alleviates, ameliorates, eliminates, reverses, relieves, inhibits, delays onset of, reduces severity of, and/or reduces incidence of one or more symptoms, features, and/or causes of a particular disease, disorder, and/or condition. In some embodiments, such treatment may be of a patient who does not exhibit signs of the relevant disease, disorder and/or condition and/or of a patient who exhibits only early signs of the disease, disorder, and/or condition. Alternatively, or additionally, such treatment may be of a patient who exhibits one or more established signs of the relevant disease, disorder and/or condition. In some embodiments, treatment may be of a patient who has been diagnosed as suffering from the relevant disease, disorder, and/or condition. In some embodiments, treatment may be of a patient known to have one or more susceptibility factors that are statistically correlated with increased risk of development of a given disease, disorder, and/or condition. In some embodiments the patient may be a human.

Machine learning module, machine learning model: As used herein, the terms "machine learning module" and "machine learning model" are used interchangeably and refer to a computer implemented process (e.g., a software function) that implements one or more particular machine learning algorithms, such as an artificial neural networks (ANN), convolutional neural networks (CNNs), random forest, decision trees, support vector machines, and the like, in order to determine, for a given input, one or more output values. In some embodiments, machine learning modules implementing machine learning techniques are trained, for example using curated and/or manually annotated datasets. Such training may be used to determine various parameters of machine learning algorithms implemented by a machine learning module, such as weights associated with layers in neural networks. In some embodiments, once a machine learning module is trained, e.g., to accomplish a specific task such as determining scoring metrics as described herein, values of determined parameters are fixed and the (e.g., unchanging, static) machine learning module is used to process new data (e.g., different from the training data) and accomplish its trained task without further updates to its parameters (e.g., the machine learning module does not receive feedback and/or updates). In some embodiments, machine learning modules may receive feedback, e.g., based on user review of accuracy, and such feedback may be used as additional training data, for example to dynamically update the machine learning module. In some embodiments, a trained machine learning module is a classification algorithm with adjustable and/or fixed (e.g., locked) parameters, e.g., a random forest classifier. In some embodiments, two or more machine learning modules may be combined and implemented as a single module and/or a single software application. In some embodiments, two or more machine learning modules may also be implemented separately, e.g., as separate software applications. A machine learning module may be software and/or hardware. For example, a machine learning module may be implemented entirely as software, or certain functions of a ANN module may be carried out via specialized hardware (e.g., via an application specific integrated circuit (ASIC), field programmable gate arrays (FPGAs), and the like).

Substantially: As used herein, the term "substantially" refers to the qualitative condition of exhibiting total or near-total extent or degree of a characteristic or property of interest.

Scaffold Model: As used herein, the term "scaffold model" refers to a computer representation of at least a portion of a peptide backbone of a particular protein and/or peptide. In certain embodiments, a scaffold model represents a peptide backbone of a protein and/or peptide and omits detailed information about amino acid side chains. Such scaffold models, may, nevertheless, include various mechanisms for representing sites (e.g., locations along a peptide backbone) that may be occupied by prospective amino acid side chains. In certain embodiments, a particular scaffold models may represent such sites in a manner that allows determining regions in space that may be occupied by prospective amino acid side chains and/or approximate proximity to representations of other amino acids, sites, portions of the peptide backbone, and other molecules that may interact with (e.g., bind, so as to form a complex with) a biologic having the peptide backbone represented by the particular scaffold model. For example, in certain embodiments, a scaffold model may include a representation of a first side chain atom, such as a representation of a beta-carbon, which can be used to identify sites and/approximate locations of amino acid side chains. For example, a scaffold model can be populated with amino acid side chains (e.g., to create a ligand model that represents at least a portion of protein and/or peptide) by creating full representations of various amino acids about beta-carbon atoms of the scaffold model (e.g., the beta-carbon atoms acting as 'anchors' or 'placeholders' for amino acid side chains). In certain embodiments, locations of sites and/or approximate regions (e.g., volumes) that may be occupied by amino acid side chains may be identified and/or determined via other manners of representation for example based on locations of an alpha-carbons, hydrogen atoms, etc. In certain embodiments, scaffold models may be created from structural representations of existing proteins and/or peptides, for example by stripping amino acid side chains. In certain embodiments, scaffold models created in this manner may retain a first atom of stripped side chains, such as a beta-carbon atom, which is common to all side chains apart from Glycine. As described herein, retained beta-carbon atoms may be used, e.g., as a placeholder for identification of sites that can be occupied by amino acid side chains. In certain embodiments, where an initially existing side chain was Glycine, the first atom of glycine, which is hydrogen, can be used in place of a beta-carbon and/or, in certain embodiments, a beta carbon (e.g., though not naturally occurring in the full protein used to create a scaffold model) may be added to the representation (e.g., artificially). In certain embodiments, for example where hydrogen atoms are not included in a scaffold model, a site initially occupied by a Glycine may be identified based on an alpha-carbon. In certain embodiments, scaffold models may be computer generated (e.g., and not based on an existing protein and/or peptide). In certain embodiments, computer generate scaffold models may also include first side chain atoms, e.g., beta carbons, e.g., as placeholders of potential side chains to be added.

DETAILED DESCRIPTION

It is contemplated that systems, architectures, devices, methods, and processes of the claimed invention encompass variations and adaptations developed using information from the embodiments described herein. Adaptation and/or modification of the systems, architectures, devices, methods, and processes described herein may be performed, as contemplated by this description.

Throughout the description, where articles, devices, systems, and architectures are described as having, including, or comprising specific components, or where processes and methods are described as having, including, or comprising specific steps, it is contemplated that, additionally, there are articles, devices, systems, and architectures of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Documents are incorporated herein by reference as noted. Where there is any discrepancy in the meaning of a particular term, the meaning provided in the Definition section above is controlling.

Headers are provided for the convenience of the reader—the presence and/or placement of a header is not intended to limit the scope of the subject matter described herein.

Described herein are methods, systems, and architectures for generating predictions of which portions of a target molecule, such as a protein, are likely to act as binding sites for—for example, influencing interactions, and/or forming part of a binding interface, with—ligands, such as other proteins. In certain embodiments, binding site prediction technologies described herein utilize machine learning models to determine, for one or more particular amino acid sites of a target, a value that measures a likelihood (e.g., a "likelihood value") that the each amino acid site is a binding site—that is, a site that, in the event the target binds to a ligand, will interact with and/or form an interface with portions of the ligand.

A. Binding Sites

Figure 1A:
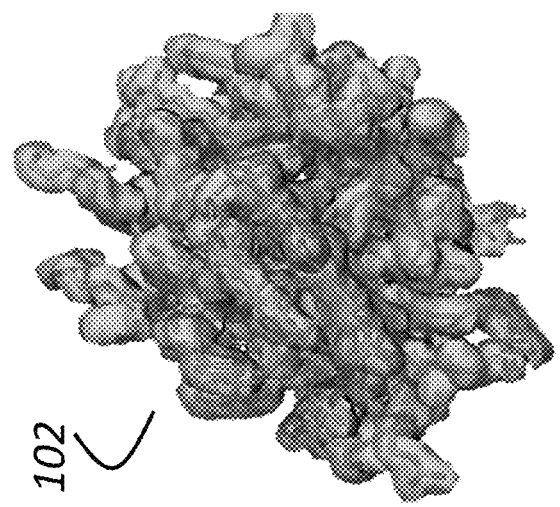
FIG. 1A is a schematic showing a three-dimensional (3D) representation of a target structure, such as a target protein and/or peptide, according to an illustrative embodiment.

Turning to FIGS. 1A and 1B, in certain embodiments, technologies described herein include processes for predicting which amino acid sites of a particular target 102 are (e.g., likely) binding sites that are likely and/or favorable sites for binding with potential ligands, such as other proteins. As illustrated in FIG. 1B, a binding site prediction 106 generated via technologies described herein may, for example, identify a set of amino acid sites within target 102 that are determined to be likely binding sites 108a, 108b, 108c.

A.i Biological Complex Models and Hotspots

Figure 2A:
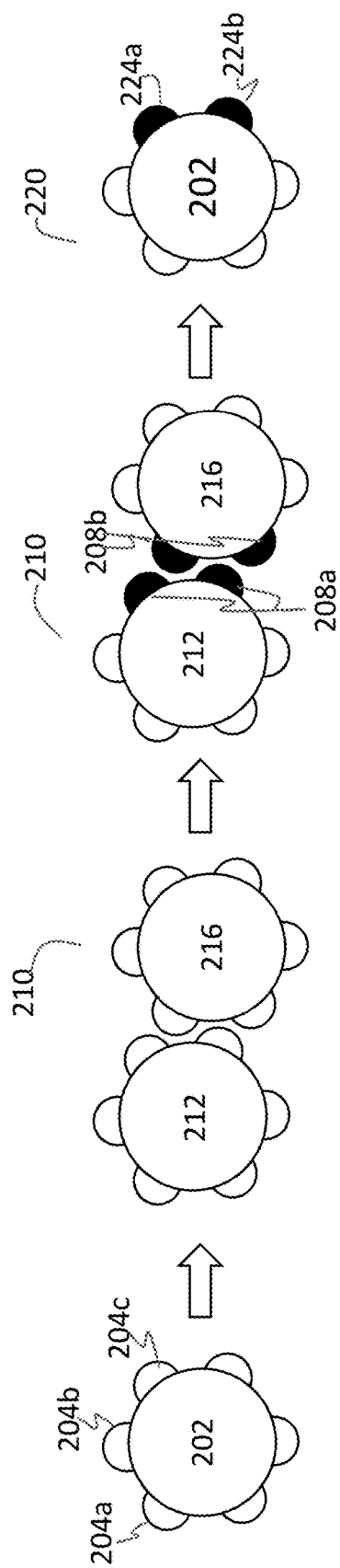
FIG. 2A is a schematic illustrating identification of hotspots and binding sites from using a biological complex model, according to an illustrative embodiment.

In certain embodiments, various amino acid sites of a particular protein may be determined to be binding sites, for example, based on experimentally determined structural data, such as x-ray crystallographic structures, of the particular protein, alone and/or in complex with other molecules. Turning to FIG. 2A, a computer representation of a particular protein structure 202, for example, based on experimentally determined crystal structures obtained from one or more databases, such as the protein databank (PDB), other public databases, proprietary databases, etc., may be analyzed to identify certain amino sites 204a, 204b, 204c as located near a surface of the particular protein and/or accessible to solvent. In certain embodiments, while such surface sites may comprise binding sites of the particular protein, a small fraction of the surface sites may be binding sites, the majority being non-binding surface sites.

Accordingly, in certain embodiments, an experimentally determined structure of a biological complex comprising a particular protein bound to one or more other proteins may be analyzed to identify, not just surface sites, but binding sites of the particular protein. For example, a biological complex model 210 comprising a representation of at least a portion of the particular protein 212 bound to another protein 216 may be analyzed to determine which amino acid sites are in close proximity to and/or interact with other members of the complex. These identified sites may then be labeled as binding sites of the particular protein, having been determined to interact with other molecules based on a biological complex model representing an experimentally determined structure of an actual, physical, existing biological complex.

Amino acid sites of members of a biological complex can be classified as interacting and/or part of a binding interface, or not, based on a variety of approaches and/or criteria. In certain embodiments, a particular amino acid site on a particular member of a biological complex may be classified based on its proximity and/or relative orientation with respect to one or more amino acid sites on other members of the biological complex. Amino acid sites that satisfy proximity and/or relative orientation-based criteria, with respect to sites of other members in a biological complex are referred to herein as hotspots. Use of positional criteria to identify hotspots in this manner is useful, for example, since experimentally determined crystal structures accurately represent relative locations of various atoms of protein molecules in complex, and those portions of one protein that are in close proximity to another are likely to be those that influence binding. For example, in certain embodiments, various distance thresholds may be used to identify amino acid sites of one or more proteins as influencing binding. In certain embodiments, distance thresholds may be combined with other criteria, for example accounting for and/or taking into consideration amino acid type, properties, surface exposure, etc.

Figure 3:
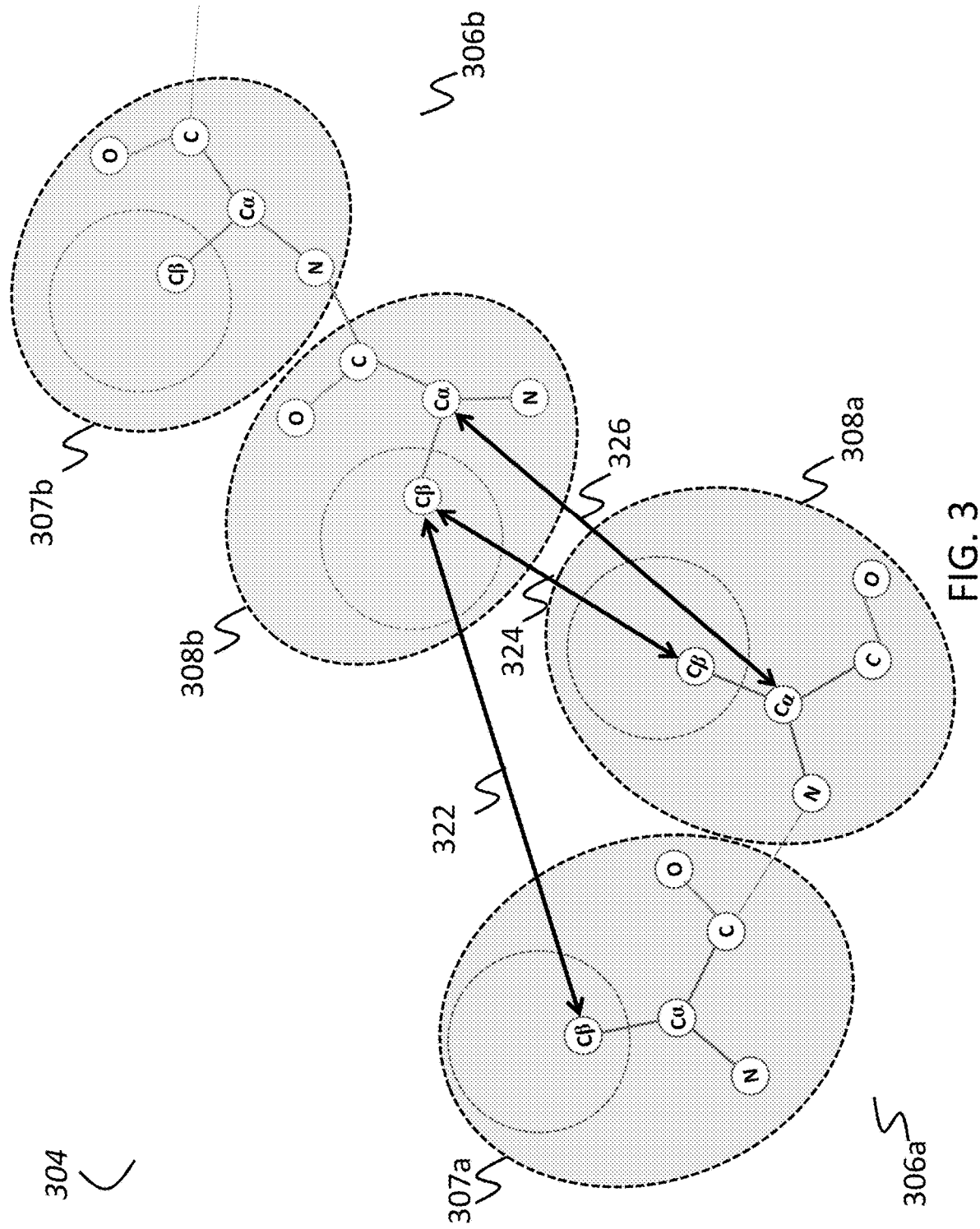
FIG. 3 is a schematic showing a portion of two polypeptide chains, according to an illustrative embodiment.

In certain embodiments, amino acid sites on one member of a biological complex may be identified as hotspots if they are located in sufficiently close proximity to one or more amino acid sites of another member of the biological complex. In certain embodiments, proximity between amino acid sites may be determined from representations biological complexes that include locations and/or types of various atoms of each member of the complex. FIG. 3, for example, shows a schematic view of a portion of two members—polypeptide chains—of a biological complex. Two amino acid sites are shown for each of first chain 306a and second chain 306b.

Various measures of proximity between amino acid sites may be used to identify amino acid sites as hotspots. FIG. 3 illustrates two such measures—namely, a beta-carbon distance (a "$C_\beta$ distance") and an alpha-carbon distance (a "$C_\alpha$ distance")—but other measures of proximity may, additionally or alternatively, be used as well. As shown in FIG. 3, each member chain of a biological complex comprises a peptide backbone populated with amino acid side chains. Each member chain comprises a plurality of amino acid sites, linked together via peptide bonds, to form a polypeptide chain. Accordingly, each amino acid site may comprise a portion of the peptide backbone, along with (i) a particular (e.g., known) amino acid side chain and/or (ii) a placeholder for an unknown, e.g., to-be-determined, amino acid side chain.

For example, as shown in FIG. 3, amino acid sites 307a and 308a of first chain 306a comprise peptide backbone atoms, e.g., N, C, C, and O, as do amino acid sites 307b and 308b of second chain 306b. Beta-carbon atoms ($C_\beta$) are also shown for each amino acid site. A $C_\beta$ is a first side chain atom common to all side chains apart from Glycine (which has a hydrogen instead of a $C_\beta$). Accordingly, $C_\beta$ (or in the particular case of Glycine, a hydrogen) can be used as a reference point to measure a distance between amino acid sites. In certain embodiments, a distance between two amino acid sites may be measured as a distance between their respective $C_\beta$'s. For example, FIG. 3 shows $C_\beta$ distances 322 and 324 measured between amino acid site 308a (of second chain 306b) and amino acid sites 307a and 308a (of first chain) 306a, respectively. In certain embodiments, a distance between two amino acid sites may be measured using other atoms, such as, for example, other atoms that are common to amino acid sites. For example, in certain embodiments, a distance between two amino acid sites may be a $C_\alpha$ distance. FIG. 3 shows $C_\alpha$ distance 326 between amino acid sites 308a and 308b of first chain 306a and second chain 306b, respectively.

In certain embodiments, a particular amino acid site of a particular member of a biological complex is identified as a hotspot if a distance—for example, a CB distance and/or Ca distance—between it and an amino acid site of another member of the biological complex is less than or below a particular threshold distance. Various threshold distances may be used for identification of hotspots. For example, in certain embodiments, a hotspot threshold distance of 8 Å (i.e., 8 Ångstroms) is used. In some embodiments, other thresholds may be used for defining a hotspot (such as less than 3 Å, less than 4 Å, less than 5 Å, less than 6 Å, less than 7 Å, less than 9 Å, less than 10 Å, less than 12 Å, less than 15 Å, less than 20 Å, as well as other suitable thresholds). In certain embodiments, hotspots may be identified based on comparison of values computed by various functions—e.g., of one or both of a $C_\alpha$ and $C_\beta$ distance—with one or more threshold values. Such functions may take into account features such as bond angles, surface area, etc.

Accordingly, in certain embodiments, a biological complex model 210 may be analyzed to identify hotspots 208a, 208b of one or more (e.g., each) members of the complex. In certain embodiments, sites of a particular protein that are classified as hotspots, based on analysis of a complex comprising the particular protein, may be identified (e.g., labeled) 220 as binding sites 224a, 224b. In certain embodiments, other criteria may be used, additionally or alternatively. For example, in certain embodiments, combinations of certain criteria may be used. For example, binding sites may be identified as those sites that are both classified hotspots and surface sites. For example, in certain embodiments, hotspots may be identified as binding sites based on distances, such as a Ca and/or CB distance, and (e.g., in combination with) a measure of exposed and/or accessible surface area for a particular amino acid site. For example, a particular amino acid site may have a Ca distance with respect to an amino acid site on another chain that satisfies a particular distance threshold, but may be excessively buried and, accordingly, inaccessible to binding. Accordingly, in certain embodiments, hotspots may be identified as those sites that satisfy a particular distance threshold and also have a measure of surface exposed/accessible area that lies above a particular surface accessibility threshold value. In certain embodiments, for example, as described in further detail herein, a Solvent Exposed Surface Area (SASA) may be computed. In certain embodiments, a measure of surface exposure/accessibility is or comprises a function of SASA. For example, a measure of surface exposure/accessibility may be or comprise (e.g., be determined as a function of) Relative Surface Area (RSA).

In certain embodiments, where binding sites are being identified for a target protein, e.g., having known side chains (e.g., as opposed to a peptide backbone with not-yet determined side-chains), atoms of particular side chains may be used to compute proximity to one or more atoms of another member chain. For example, a closest distance between any non-hydrogen atom of a particular side chain and another non-hydrogen atom on a different chain may be determined, and compared with a distance threshold, in order to label the particular amino acid site as a hotspot. As with hotspot threshold distances used for comparison with CB distances, a variety of hotspot threshold distances may be used when comparing closest (non-hydrogen) atom distances. For example, in certain embodiments, a hotspot threshold distance of 4.5 Å (i.e., 4.5 Ångstroms) is used. In some embodiments, other thresholds may be used for defining a hotspot (such as less than 2 Å, less than 3 Å, less than 4 Å, less than 5 Å, less than 6 Å, less than 7 Å, less than 8 Å, less than 9 Å, less than 10 Å, less than 12 Å, as well as other suitable thresholds).

A.ii Surface Sites

In certain embodiments, whether a particular amino acid site is a surface site can be determined based one or more metrics that measure of an amount or relative portion of the particular amino acid that is exposed to solvent. For example, in certain embodiments, a solvent accessible surface area may be determined for a particular amino acid and used to classify the particular amino acid as a surface site or not. In certain embodiments, a solvent accessible surface area for a particular amino acid site may be scaled by a (e.g., site independent) surface area of the particular amino acid located at the site, to compute a relative surface accessible area (RSA) metric, described in further detail herein. In certain embodiments, a particular surface accessibility metric, such as a RSA, may be compared to a threshold value, such that those sites having values of the particular surface accessibility metric at or above the threshold value are classified as surface sites, and those that have surface accessibility metric values below it are classified as buried.

A.iii Binding Sites of One or More Biological Complex Models

Figure 2B:
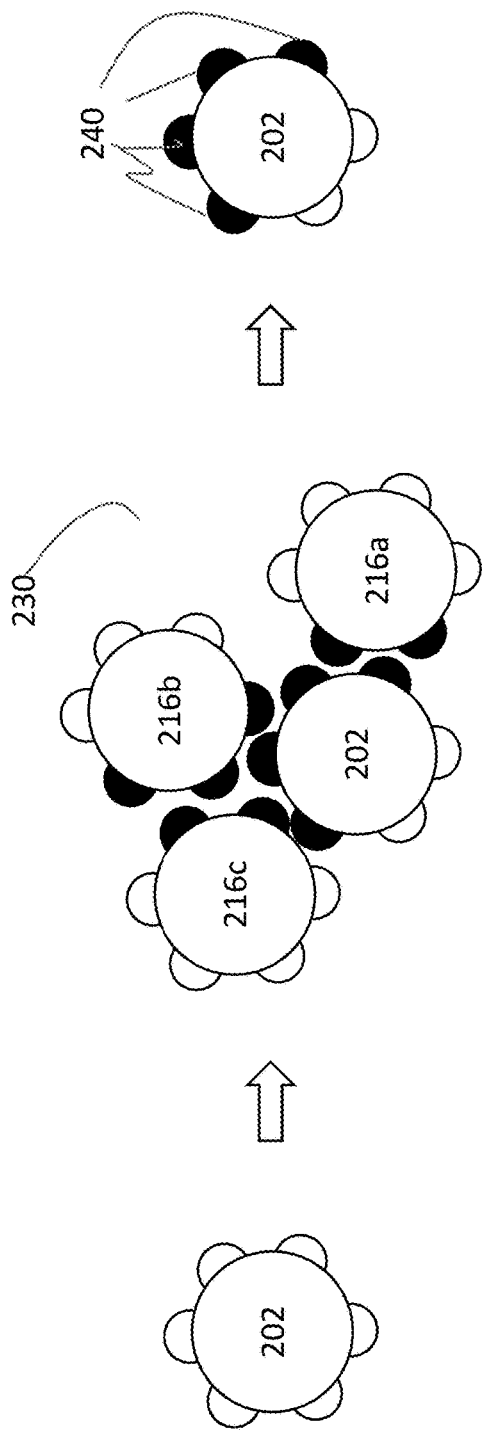
FIG. 2B is another schematic illustrating identification of hotspots and binding sites from using a biological complex model, according to an illustrative embodiment
Figure 2C:
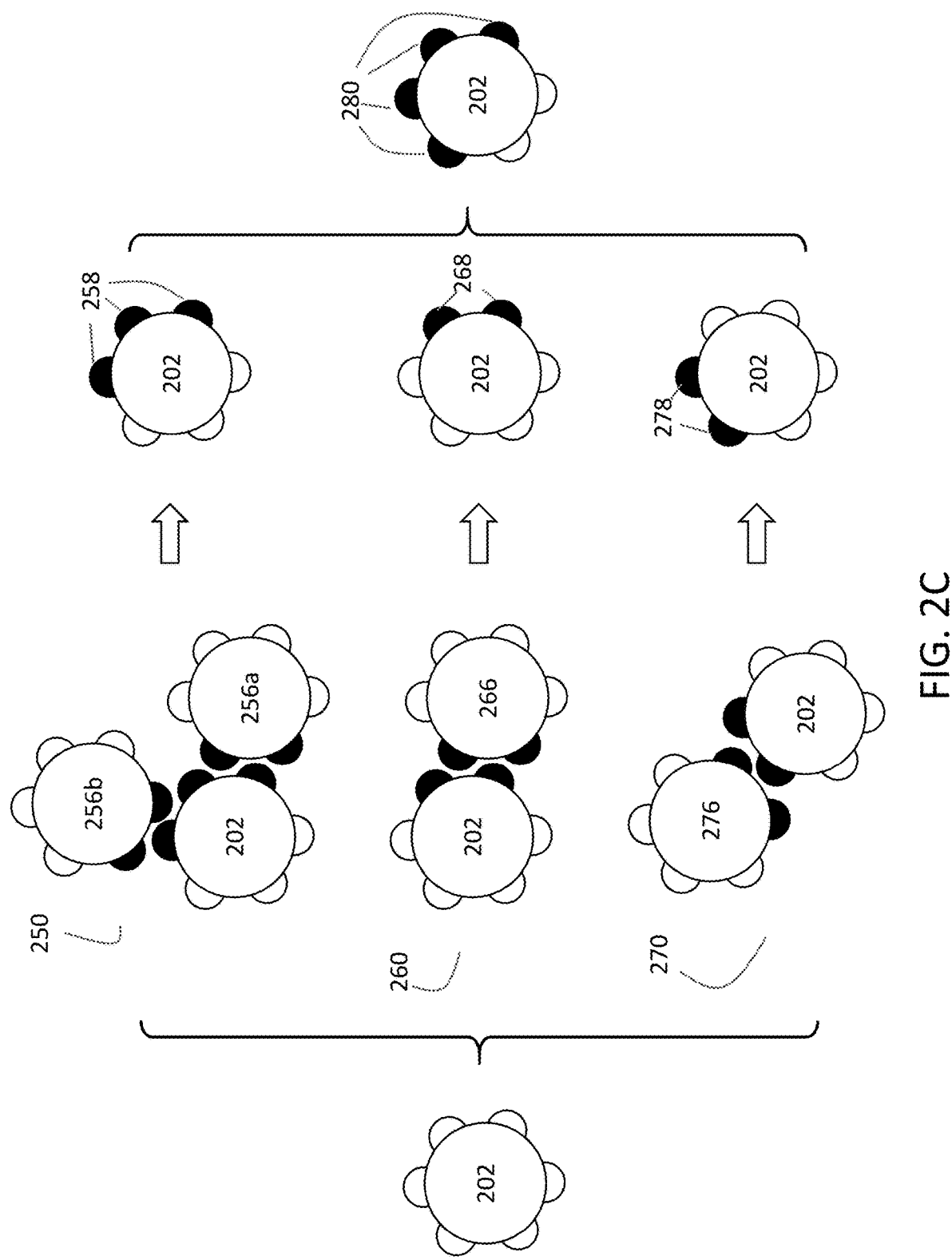
FIG. 2C is a schematic illustrating identification of hotspots and binding sites using multiple biological complex models, according to an illustrative embodiment

Turning to FIGS. 2A-C, in certain embodiments, one or more binding sites of a particular protein may be identified based on a biological complex model representing a complex comprising the particular protein and one or more other member proteins. In certain embodiments, the biological complex is or comprises a dimer, comprising the particular protein and a single other member protein, for example as represented by complex model 210 shown in FIG. 2A. In certain embodiments, a biological complex model 230 represents a complex comprising the particular protein 202 bound to multiple—e.g., two or more—other proteins, such that a first set of binding sites are determined based on interaction between the particular protein 202 and a first member 216a of the complex, a second set of binding sites are determined based on interaction with a second member 216b of the complex, and so on, which may be combined to identify an final set of binding sites 240, as illustrated in FIG. 2B.

Turning to FIG. 2C, in certain embodiments, binding sites for a particular protein 202 may be determined using and/or based on multiple biological complex models 250, 260, 270, each comprising a representation of the particular protein bound to one or more other proteins. For example, a set of hotspots may be identified for each of a plurality of biological complex models and, in turn, for each complex, an initial set 258, 268, 278 of binding sites determined based on each hotspot set. Initial sets of binding sites 258, 268, 278 may be combined to produce a final set of binding sites 280, for example as a union, intersection, or other function of the initial sets of binding sites.

Sets of binding sites for a particular protein may be represented in a variety of manner. For example, a set of binding sites may identify certain amino acid sites as binding sites, for example via a labeling scheme, whereby likely binding sites are labeled with one value (e.g., a "1." a Boolean "True,", and particular alphanumeric character or string, etc.) and other (non-binding) sites are labeled with another value (e.g., a "0," a Boolean "False," another alphanumeric character or string, etc.) and/or un-labeled.

B. Machine Learning-Based Prediction of Binding Sites

Figure 4A:
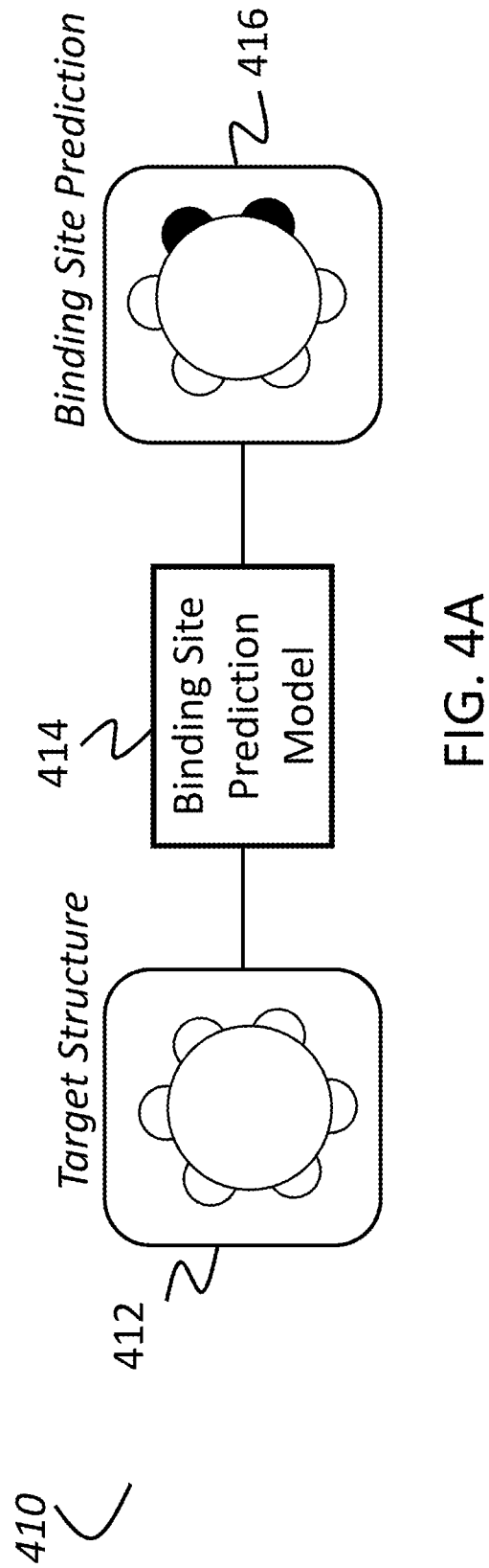
FIG. 4A is a block-flow diagram of an example process for generating a binding site prediction, according to an illustrative embodiment.

Turning to FIG. 4A, in certain embodiments, systems and methods described herein use AI-based computer implemented processes 410 to predict, for a particular target structure, which sites are binding sites, without a need to obtain or analyze a structural model of the particular target in complex with another molecule. In this manner, binding site prediction technologies described herein can obviate a complex, time-consuming, and expensive experimental structure determination process and, among other things, rapidly generate predictions for particular targets that may not yet be characterized and/or for which binding partners (such as other proteins) may be entirely unknown, e.g., the subject of extensive research efforts.

In certain embodiments, an example binding site prediction process 410 may use a machine learning model 414 to generate a binding site prediction 416. In example process 410, a target model—a computer representation of at least a portion of a target structure 412—is received, as input, by machine learning model 414. Target model 412 may, for example, be a representation of a particular target protein alone, not in complex with another protein. Machine learning model 414 may generate binding site prediction 416 as output, for example, based on received target model 412.

B.i Training Example Construction

Figure 4B:
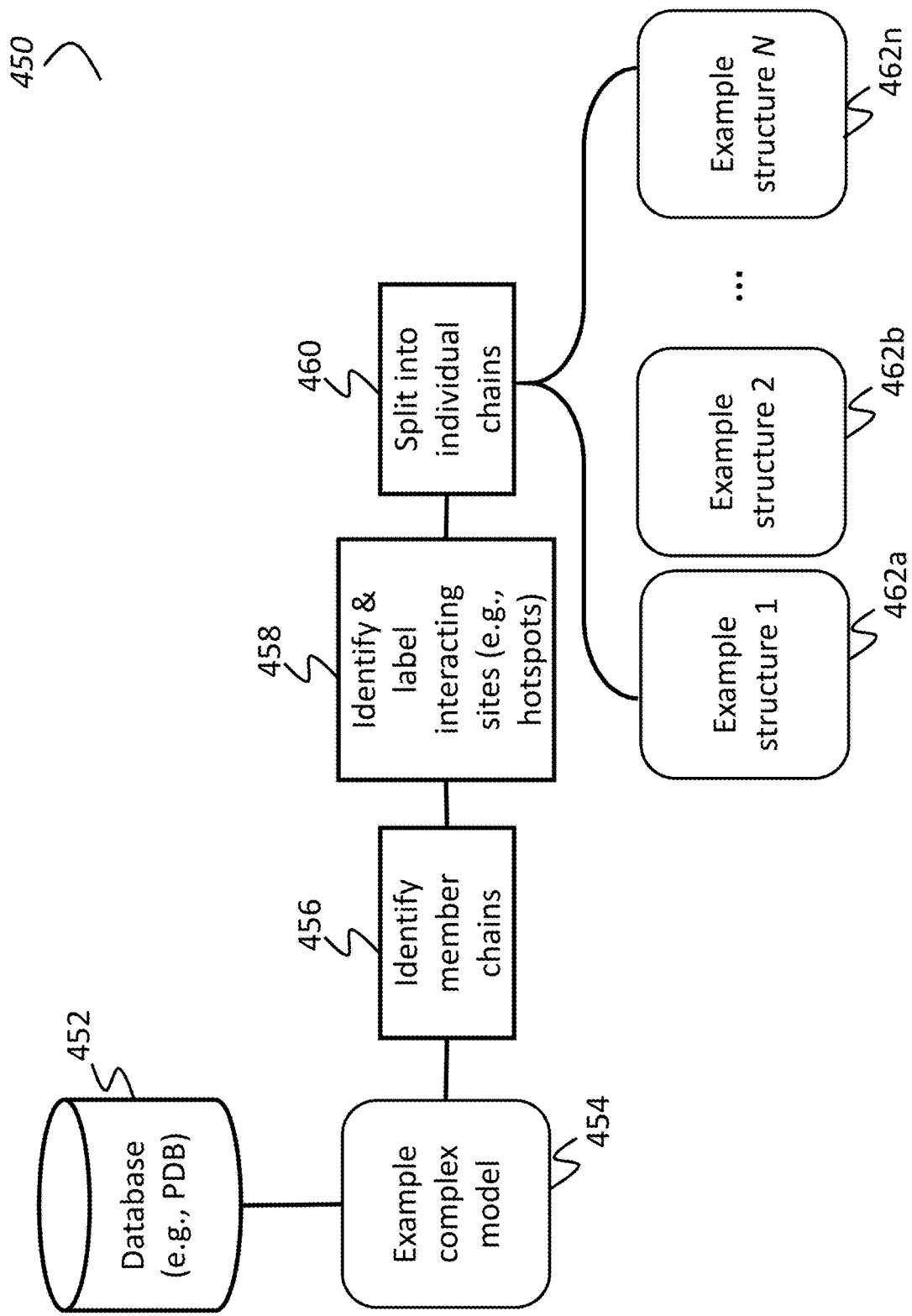
FIG. 4B is a block-flow diagram of an example process for generating a dataset of examples for use in training a machine learning model to generate binding site predictions, according to an illustrative embodiment.

Turning to FIG. 4B, in certain embodiments, in order to generate a binding site prediction 416, machine learning model 414 is trained using examples of proteins that are known to form complexes with other proteins. During training, machine learning model 414 learns—e.g., weights of its variable parameters are adjusted and optimized—to accurately identify which amino acid sites of a particular example protein interact with and/or are part of a binding interface with another protein when the example protein binds with the other protein to form a complex, based on (analysis of) a representation of the particular example protein alone (e.g., and not a representation of a biological complex, e.g., in contrast to the approaches described in section A, above). Once its learnable parameters are tuned to accurately identify binding sites of known proteins, machine learning model 414 may be fixed (e.g., parameters not adjusted further) and applied to unknown proteins—e.g., proteins that are not necessarily known to form complexes with other molecules and/or, if they do, have not been structurally characterized in complex, such that their binding sites are unknown.

FIG. 4B illustrates an example training process 450. During training, examples of proteins that form complexes with other proteins can be obtained from experimentally determined structural data of physical protein-protein complexes. Training example complexes can be obtained, for example, from structures derived from x-ray crystallographic data, and found in databases 452, for example public databases such as the Protein Data Bank (PDB), and, additionally or alternatively, proprietary databases.

Figure 4C:
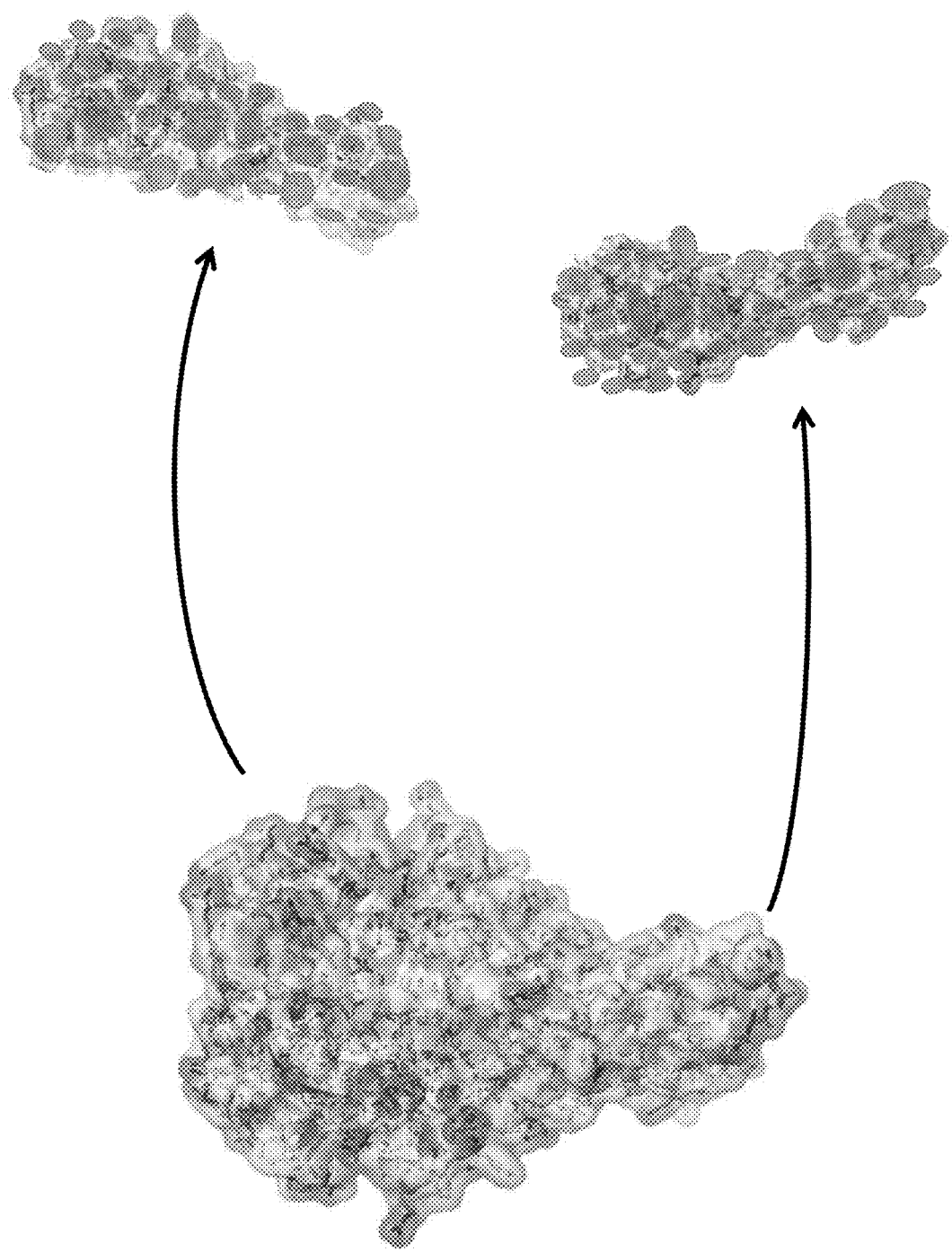
FIG. 4C is a schematic illustrating a representation of a biological complex split into two constituent member chains, according to an illustrative embodiment.

A particular biological complex model 454, representing two or more member proteins and/or peptides, referred to herein as chains (e.g., as in polypeptide chains) bound together, may be analyzed to determine, for each member chain, which amino acid sites of the member chain interact with amino acid sites on other chains, for example via the approaches described herein, e.g., in section A, above. For example, FIG. 4C shows a model representing a biological complex comprising two proteins. Biological complex models may represent complexes comprising two or more, for example three, or four, or more, proteins, as well as combinations of proteins and shorter peptide chains. In certain embodiments, different member chains of a biological complex model are identified, for example via use of particular encoding schemes, classes, and the like. In certain embodiments, a biological complex model may be analyzed to identify each member chain. Once each member chain of a complex model is identified 456, amino acid sites on each member chain can be analyzed to determine which sites on one chain interact with and, accordingly, form an interface with, sites of other chains.

Accordingly, returning to FIG. 4B, for each member chain of an example complex, certain amino acid sites, e.g., satisfying criteria as described herein, may be identified and labeled as hotspots 458. In certain embodiments, once hotspots are identified on each member chain of a biological complex, a biological complex is split into its constituent member chains, and each member chain is extracted 460 and used as an example structure for use in training a machine learning model. In this manner, a single example biological complex model can be used to create two or more example structures 462a, 462b, . . . . 462n, depending on a number of member chains of the biological complex model (e.g., a complex comprising N chains may be used to create 1, or 2, or . . . up to N example structures). As illustrated in FIG. 4C, each constituent member chain of the complex can be used as a training example, with those amino acid sites that were identified as hotspots when the particular chain was in complex labeled as binding sites.

B.ii Training and Inference

Accordingly, machine learning model 414 may be trained using example chains that are extracted from biological complexes and, accordingly, comprise one or more amino acid sites known to be hotspots when the example chain forms a complex with another chain. During training, machine learning model 414 may receive, as input, an unlabeled example chain representation, and generate, as output, an identification of which amino acid sites will be hotspots if/when the chain forms a complex and, accordingly, represent potential binding sites. A loss, or error, function, may then be computed by comparing machine learning model 414's binding site prediction for a particular chain with the known hotspots of the chain. In this manner, machine learning model 414 can be trained to generate a binding site prediction that identifies amino acid sites that, when a chain forms a complex, will be hotspots, as binding sites. Once trained, machine learning model 414 may do so (predict binding sites) based solely on a representation of at least a portion of particular protein and/or one or more sub-units of a target protein complex alone/in isolation. For example, in certain embodiments, a target protein may be a protein in monomeric form. Machine learning model 414 may then receive, as input a representation of at least a portion of target protein in its monomeric form—i.e. in isolation, and determine a binding site prediction based solely on the representation of the target protein in isolation. In certain embodiments, a target is or comprises a multiple sub-units and/or has a multimeric quaternary structure (e.g., a dimer, trimer), but may, for example, bind to additional molecules. Accordingly, machine learning model 414 may receive a representation of at least a portion of the target, including at least a portion of one or more sub-units thereof, and predict those sites (e.g., apart from those that join sub-units) that bind to additional molecules. Accordingly, following training, machine learning model 414 may be presented with a new, unknown target structure that may or may not be known to form complexes, and/or for which complexes have not been measured. Machine learning model 414 then predicts, for target structure, which sites will be binding sites. In this manner, machine learning model 414 can be used to generate a binding site prediction 416.

B.iii Binding Site Predictions

Binding site prediction 416 may be represented and/or stored in a variety of formats and manners. In certain embodiments, binding site prediction 416 is and/or comprises an identification of one or more amino acid sites of target structure 412 that are or have been determined, using machine learning model 414, to be likely binding sites. An identification of, e.g., a set of, amino acid sites determined to be (e.g., classified as) likely binding sites may be represented in a variety of manners. For example a representation of target structure 412 may be labeled such that each amino acid site of target structure 412 identified as a binding site is labeled with a first value, while other amino acid sites are labeled with another, e.g., second, value and/or are unlabeled. For example, a binary labeling scheme, where amino acid sites identified as binding sites may be labeled with a "1," and other amino acid sites labeled with a "0," may be used. Additionally or alternatively, amino acid sites identified as binding sites may be labeled with a Boolean "True" and other sites labeled with a Boolean "False." Other labeling approaches that differentiate between binding sites and other amino acid sites (that are not identified as binding sites) may be used. In certain embodiments, binding sites of target structure 412 may be identified using index values that identify particular amino acid sites, for example with a unique identifier for each amino acid site of target structure 412. A, for example, vector of values may then be used to list the index values of those amino acid sites that are determined to be binding sites.

In certain embodiments, a binding site prediction 416 comprises, for each of at least a portion of amino acid sites of target structure 412, a score, such as a likelihood value. In certain embodiments, a likelihood value determined for a particular amino acid site measures a likelihood that the particular amino acid site is a binding site. Such likelihood values may, for example, be floating point number between zero and 1, thereby indicating a probability that each particular amino acid site is a binding site. Likelihood values may be determined, presented, and/or stored in a variety of manners, not limited to a 0 to 1 probability. For example, values ranging from 0 to 100, or on other scales may be used. Scales may be linear or non-linear.

In certain embodiments, a binding site prediction that identifies, for example via a labeling approach as described above, one or more amino acid sites of target structure 412 as binding sites is generated based on an initial, e.g., preliminary, output from machine learning model 414. For example, in certain embodiments, machine learning model 414 initially determines likelihood values for each of at least a portion of amino acid sites of target structure 412. One or more subsequence processing steps may then be used to classify each particular amino acid site of the portion as a binding site or not, for example, by comparing its particular likelihood score with a threshold value. Threshold values may be varied and/or selected, for example based on certain criteria, such as a true positive rate, a false positive rate, sensitivity, specificity, etc. Amino acid sites classified as binding sites may be assigned a label, or indexed, based on comparison of their corresponding likelihood values to a threshold value, to generate a final binding site prediction 416.

In certain embodiments, binding site predictions may include a label and/or score for each amino acid site of target structure 412. In certain embodiments, binding site predictions may include labels and/or score for a subset of amino acid sites of target structure 412. For example, in certain embodiments, binding site predictions may be restricted to those amino acid sites of a target structure 412 that are determined to be surface sites of target structure 412.

In certain embodiments, a binding site prediction 416, such as a set of likelihood values, may initially be determined for all amino acid sites of a target structure. In certain embodiments, only values for surface sites are retained, and values for buried sites discarded. In certain embodiments, labels may be assigned only to surface sites. In certain embodiments, machine learning model 414 generates a binding site prediction only for surface sites.

C. Graph Neural Network (GNN) Models for Binding Site Prediction

Figure 5:
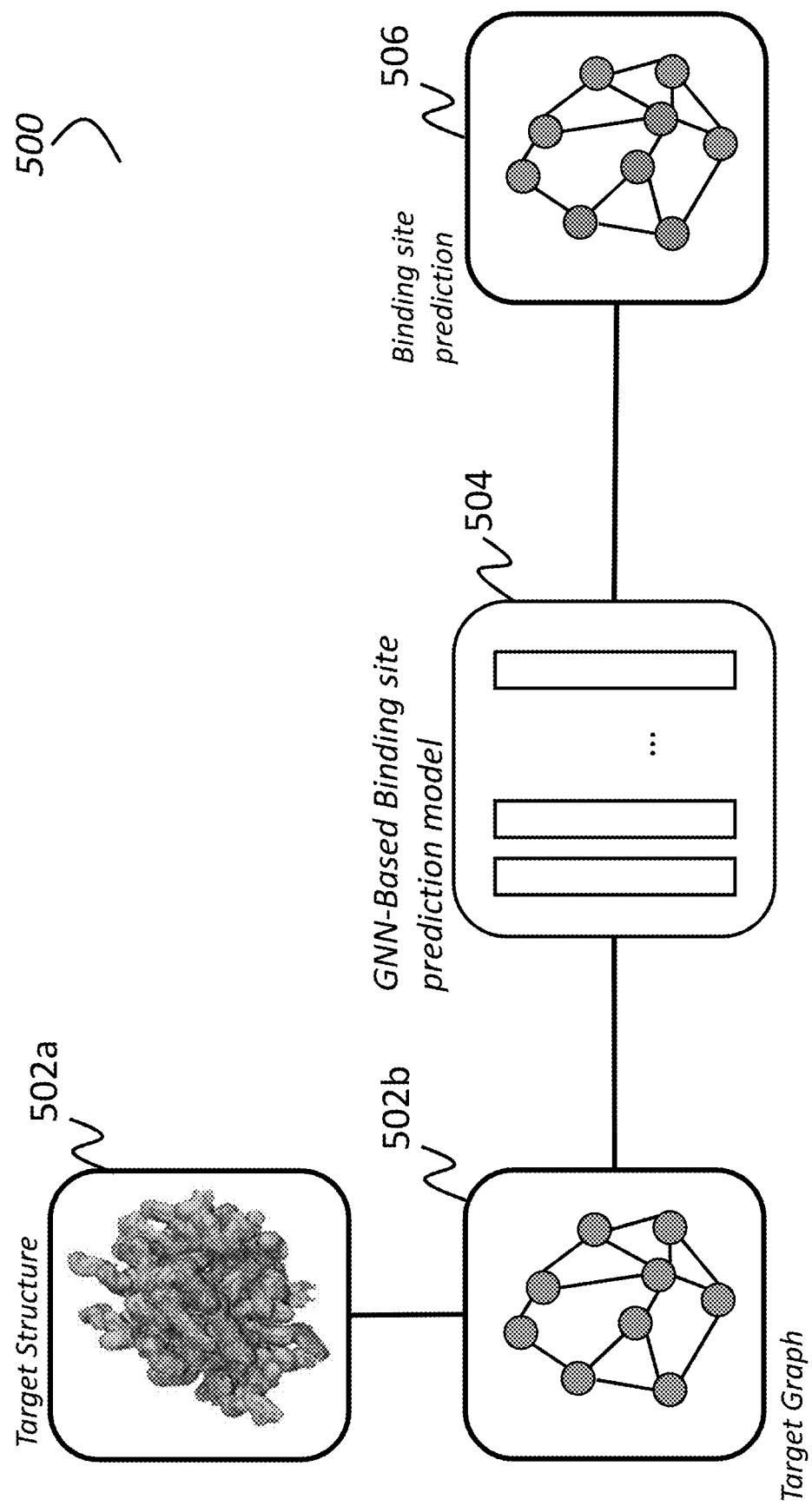
FIG. 5 is a block flow diagram of an example process for generating a binding site prediction using a graph neural network (GNN), according to an illustrative embodiment.

Turning to FIG. 5, in certain embodiments, in a binding site prediction process 500, machine learning model 114 is and/or comprises a graph neural network (GNN) that receives a graph representation of a target structure 502a—a target graph 502b—as input and performs node classification to generate a binding site prediction 506.

C.i Graph Representations

Target graph 502b may include and/or be based on a variety of graph representation approaches, including, but not limited to, those described in U.S. patent application Ser. No. 17/871,425, entitled, "Systems and Methods for Artificial Intelligence-Based Prediction of Amino Acid Sequences at a Binding Interface," filed Jul. 22, 2022, the content of which is incorporated by reference in its entirety.

For example, in certain embodiments, structures of proteins and/or peptides, or portions thereof, may be represented using graph representations. Biological complexes, for example comprising multiple proteins and/or peptides, as well as, in certain embodiments small molecules, may also be represented using graph representations. An entire protein, peptide, or complex thereof may be represented via a graph representation, or, in certain embodiments, a graph representation may be used to represent structure of a particular portion, such as in a vicinity of an interface between two or more molecules (e.g., constituent proteins and/or peptides of the complex).

For example, turning to FIGS. 6A and 6B, a graph representation approach, used in certain embodiments to represent a biologic, such as a protein and/or peptide, is illustrated. FIG. 6A shows a 3D, volumetric, representation 602a of a protein. FIG. 6B shows a schematic of a corresponding graph representation 602b of the protein shown in FIG. 6A. As shown in FIG. 6B, graph representation 602b comprises a plurality of nodes, and, in certain embodiments, edges. In FIG. 6B, each node is illustrated as a circle and each edge is shown as a line connecting two nodes. For example, nodes 624a and 624b are connected by edge 626a.

In certain embodiments, each node in a graph representation represents a particular amino acid site and has a node feature vector 640 that is used to represent certain information about the particular amino acid site. For example, a node feature vector may represent information such as an amino acid amino acid type, a local backbone geometry, a side chain rotamer structure, as well as other features such as a number of neighbors, an extent to which the particular amino acid site is buried or accessible, a local geometry, etc.

Edges in a graph representation may be used to represent interactions and/or relative positions between amino acid sites. As with nodes, each edge may have an edge feature vector 660. An edge feature vector may be used to represent certain information about an interaction and/or relative positioning between two amino acid sites, such as a distance, their relative orientation, etc.

Node Features

Figure 7:
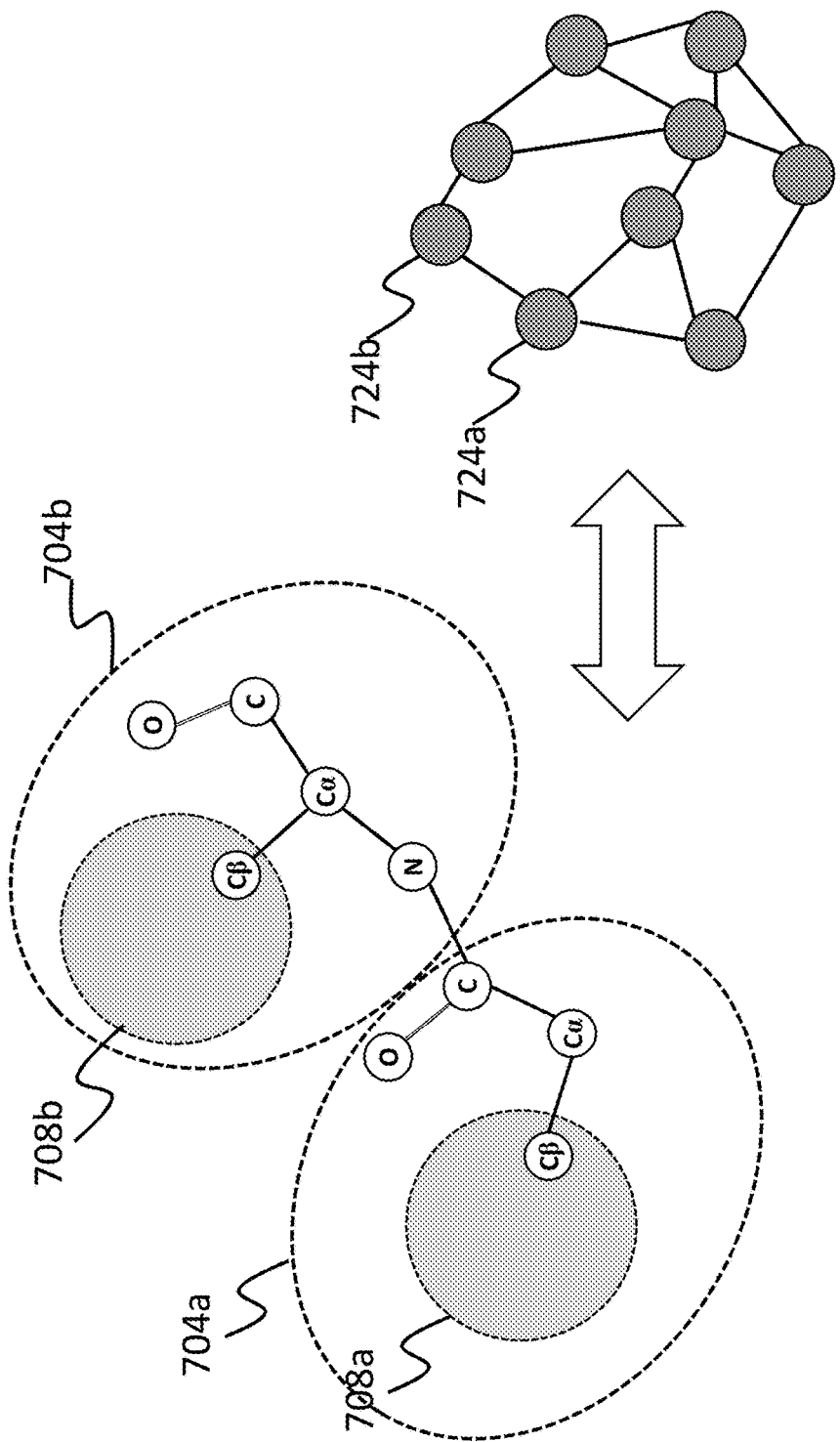
FIG. 7 is a diagram illustrating representation of amino acid sites of a target structure via nodes in a graph representation, according to an illustrative embodiment.

Turning to FIG. 7, as described herein, nodes represent amino acid sites on a ligand and/or target, such as a protein or peptide. In certain embodiments, each amino acid site includes peptide backbone atoms (e.g., N, $C_\alpha$, C, O, as shown in FIG. 7) together with a side chain, which may be known, or as yet unknown, to-be-determined. For example, as shown in FIG. 7, nodes 724a and 724b represent amino acid sites 704a and 704b of a particular protein, each of which includes peptide backbone atoms along with a side chain, 708a and 708b, respectively. Side chains 708a and 708b may be particular, e.g., known side chains, partially known (for example, an amino acid type may be known, but other information, such as rotamer structure may be unknown and/or subject to change (e.g., upon binding)), and/or, in certain embodiments, side chains such as 708a and 708b may be unknown and/or to-be-determined, but can, for example, be approximately located by virtue of the beta-Carbon (CR) atoms as shown in FIG. 7. For example, target graph 502b may identify particular amino acid types for each amino acid site since a full amino acid structure/sequence of a target may be known. In certain embodiments, a scaffold model may be represented using a graph, which, as described in further detail herein, includes peptide backbone atoms, but for which particular amino acid side chains for each site are unknown and to-be determined quantities.

A node feature vector may be used to represent information about a particular amino acid site, such as amino acid type (if known), local backbone geometry (e.g., torsional angles describing orientations of backbone atoms), rotamer information, as well as other features such as a number of neighbors, an extent to which the particular amino acid is buried or accessible, a local geometry, and the like. Various approaches for encoding such information may be used in accordance with technologies described herein.

Figure 8:
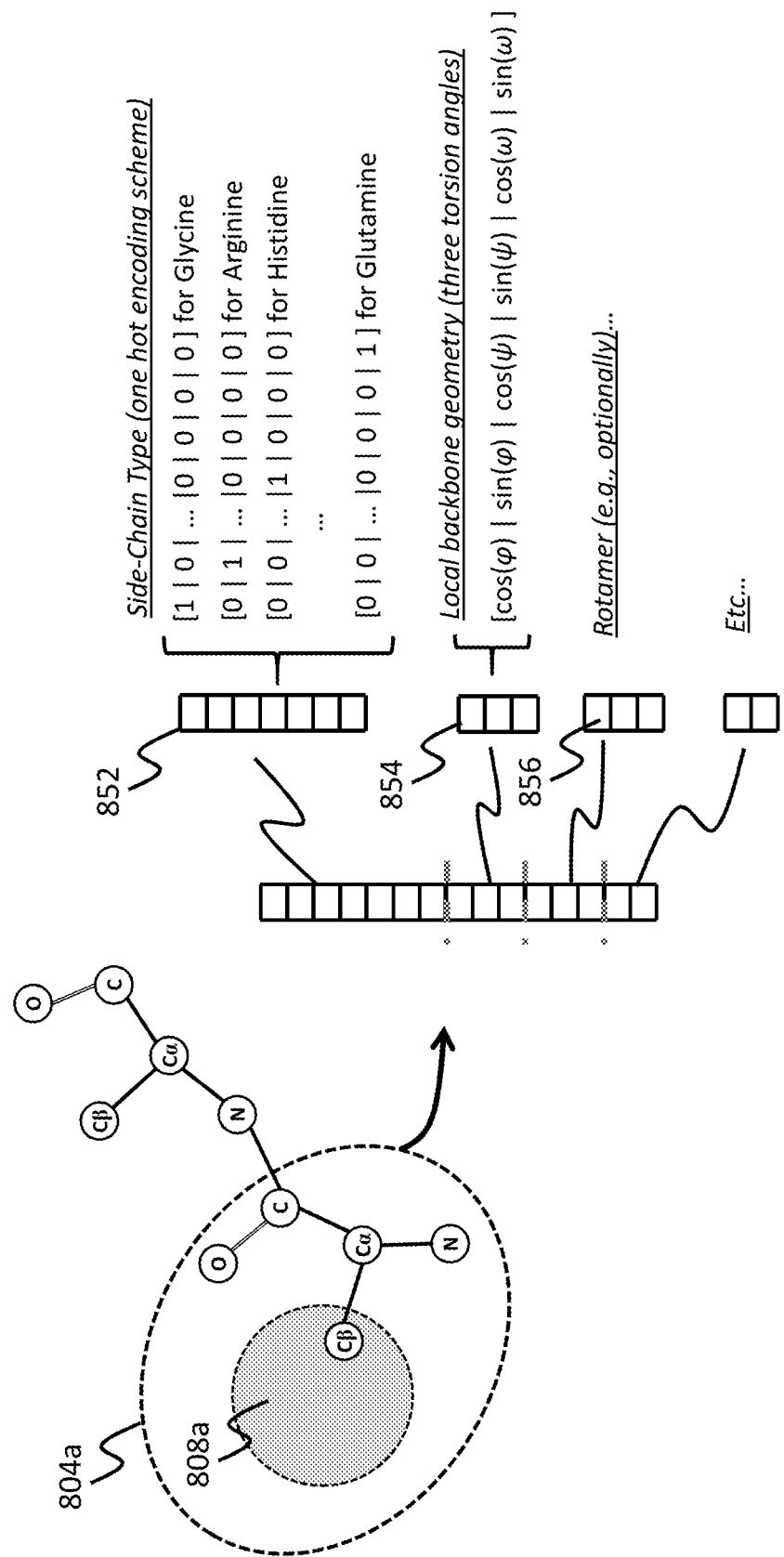
FIG. 8 is a diagram illustrating an example approach for encoding structural information of amino acid sites of a biologic via a node feature vector of a graph representation, according to an illustrative embodiment.

For example, in certain embodiments, a node feature vector comprises one or more component vectors, each component vector representing a particular structural feature at a particular amino acid location, as illustrated in FIG. 8. That is, a node feature vector may be thought of as several component vectors 'stitched', or concatenated, together. Each component vector may include one or more elements, whose values encode a particular type of structural information. For example, as shown in FIG. 8, one component vector 852 may be used to represent an amino acid type for side chain 808a, another component vector 854 used to encode local backbone geometry, another component vector 856 to encode rotamer structure of side chain 808a, and so on. In certain embodiments, only an amino acid type and, optionally, local backbone geometry, encoded by component vectors 852 and 854 may be used or known. For example, a node feature vector used in binding site prediction approaches as described herein may exclude rotamer structure. Without wishing to be bound to any particular theory, excluding rotamer structure is believed, in certain embodiments, to improve quality of predictions because, in real, physical molecules, side chains may flex and change their rotamer structure during and/or upon binding.

In certain embodiments, amino acid type may be represented via a one-hot encoding technique, whereby each node feature vector comprises a twenty element side chain component vector 852 comprising 19 "0"s and a single "1," with the position of the "1" representing the particular amino acid type (e.g., glycine, arginine, histidine, lysine, serine, glutamine, etc.) at a particular node/amino acid site. In certain embodiments, local backbone geometry may be represented using three torsion angles (e.g., the phi ($\varphi$), psi ($\psi$), and omega ($\omega$) representation). In certain embodiments, a node feature vector may include a component vector representing a rotamer, for example a vector of chi angles. In certain embodiments, each angle may be represented by two numbers—e.g., a sine of the angle and a cosine of the angle.

In certain embodiments, a node feature vector comprises one or more components that encode electrostatic and/or chemical properties of an amino acid side chain. For example, in certain embodiments, an electrostatic classification component may encode information relevant to electrostatic properties and/or interacts of the amino acid. For example, in certain embodiments an electrostatic classification component can comprise one or more values that classify and/or measure a polarity and/or charge of an amino acid site. For example, an electrostatic classification component may be a single numerical value, having one of four possible discrete values (e.g., 0, 1, 2, or 3) to indicate whether a particular amino acid site is apolar (e.g., not polar), polar, negatively charged, or positively charged.

Edges and Edge Features

In certain embodiments, as described herein, edges may be used to represent interactions between and/or a relative positioning between two amino acid sites. A graph representation accounting for interactions between every amino acid could include, for each particular node representing a particular amino acid site, an edge between that node and every other node (e.g., creating a fully connected graph). In certain embodiments, a number of edges for each node may be limited (e.g., selected) using certain criteria such that each node need not be connected to every other node and/or only certain, significant, interactions are represented. For example, in certain embodiments, a k-nearest neighbor approach may be used, wherein interactions between a particular amino acid and its k nearest neighbors (k being an integer, e.g., 1, 2, 4, 8, 16, 32, etc.) are accounted for in a graph representation, such that each node is connected to k other nodes via k edges. In certain embodiments, a graph representation may only include edges for interactions between amino acids that are separated by a distance that is below a particular (e.g., predefined) threshold distance (e.g., 2 angstroms, 5 angstroms, 10 angstroms, etc.).

Figure 9:
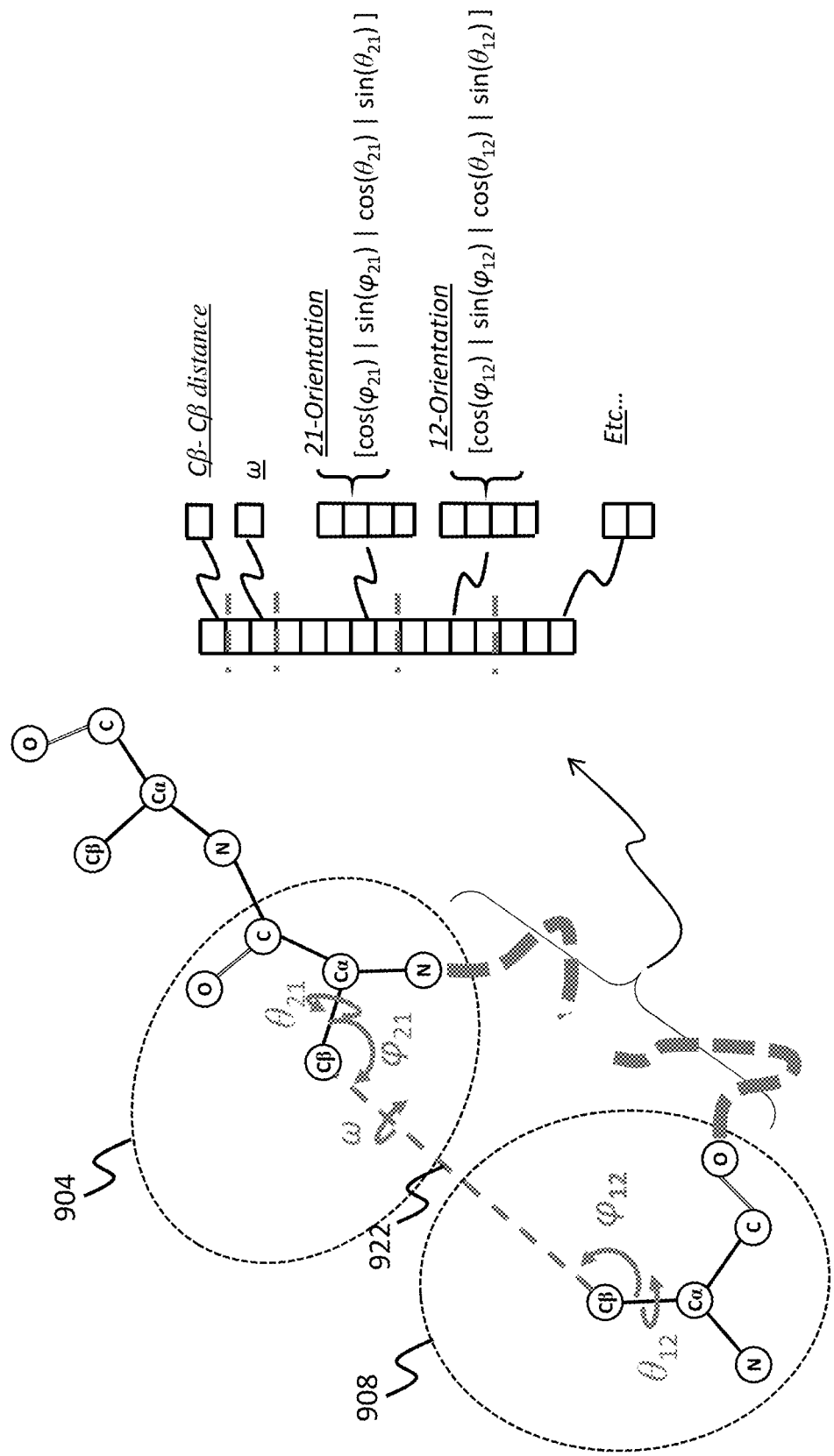
FIG. 9 is a diagram illustrating an example approach for encoding relational information (e.g., interactions and/or relative positioning) between two amino acid sites of a biologic via an edge feature vector of a graph representation, according to an illustrative embodiment.

Turning to FIG. 9, in certain embodiments, an edge feature vector includes a representation of a relative distance and orientation between two amino acid sites. For example, an edge feature vector may include a value representing a distance 922 between beta-Carbon atoms of the two amino acid sites 904 and 908, along with values representing the three dihedral angles and two planar angles that represent their relative orientations. In certain embodiments, an edge feature vector may also include a value indicating whether the two nodes it connects represent amino acid sites on a same or different molecule. In the scheme shown in FIG. 9 a $C_\beta$-$C_\beta$ distance and $\omega$ (e.g., measuring rotation about an axis connecting the two Cβ atoms) are symmetric—i.e., invariant with respect to whether site 908 is considered site 1 and site 904 is considered site 2 or vice-a-versa. Angles $\varphi_{21}$, $\theta_{21}$, $\varphi_{12}$, and $\theta 1_2$ (and, accordingly, the four element feature vectors shown in FIG. 9 that are derived therefrom), however, are asymmetric with respect to which site is labeled 1 and which is labeled 2. Accordingly, in certain embodiments, multiple, e.g., directed, edges may be used to connect each pair of nodes. For example, in certain embodiments, two edges may be used, with one edge having a feature vector created by considering two nodes in one order, and another edge having a feature vector created by considering the two nodes in the reverse order. For example, using two directed edges to implement the scheme shown in FIG. 9, the $C_\beta$-$C_\beta$ distance and ω values for each edge feature vector would be the same, but the 2-1 and 1-2 orientation feature vectors would be reversed, due to their asymmetry.

In certain embodiments, an edge feature vector may encode a type of interaction between side chains of amino acid sites represented by the two nodes it connects. For example, in certain embodiments, an edge feature vector may comprise an electrostatic classification component, which may, for example, be a two-element vector, comprised of (two) values that classify and/or measure a polarity and/or charge of amino acid side chains represented by the two nodes that a particular edge connects.

Relative and Absolute Spatial Encoding Features

In certain embodiments, a graph representation may include only features that are invariant with respect to rotation and translation in three dimensional space. For example, as described above and illustrated in FIGS. 3A-C, local backbone torsion angles do not change when an entire biological complex is rotated and/or translated in 3D space. Likewise, edge feature vectors that represent relative distances between two amino acids and their relative orientations with respect to each other also do not change when an entire biological complex is rotated and/or translated in 3D space. In certain embodiments, use of relative features, which are invariant under 3D translation/rotation is advantageous in that it obviates a need to train a machine learning model to avoid interpreting versions of a single structure that are rotated and/or translated as different structures.

Additionally or alternatively, in certain embodiments, absolute coordinate values, such as Cartesian x,y,z coordinates may be used in node feature vectors. In certain embodiments, this approach simplifies structural representations, for example allowing a graph to represent a 3D protein and/or peptide structure with only nodes and simplified edges (e.g., edges without information pertaining to relative position and/or orientation and/or distance between nodes, e.g., edges with a reduced number of features e.g., featureless edges). In certain embodiments, when absolute (as opposed to relative) coordinates are used, node features may no longer be invariant with respect to 3D rotation and/or translation and, accordingly, a training approach that ensures a machine learning model is equivariant to rotations and translations in 3D space is used.

C.ii GNN Input Graphs and Likelihood Graph Output

Turning again to FIG. 5, GNN model 504 may be trained as described herein, for example via use of example structures derived from known complexes. Training may be carried out as described herein, e.g., in Section B above, with each training example represented by a graph and input to GNN model 504.

Once trained, GNN model may receive target graph 502b as input and generate, as output, a binding site prediction 506. In certain embodiments, binding site prediction 506 is or comprises a likelihood graph. A likelihood graph may comprise, for each of one or more nodes of target graph 502b, a likelihood value, determined by GNN model 504, which represents and/or measures, for each particular node, a likelihood that a particular amino acid site to which the particular node corresponds is a binding site. In certain embodiments, GNN model 504 may determine a likelihood value for each node of target graph 502b, such that likelihood graph comprises a likelihood value for each node of target graph 502b. In certain embodiments, GNN model 504 determines likelihood values for only a subset of nodes of target graph 502b. The subset may, for example, be those nodes of target graph that are determined to correspond to surface amino acid sites.

Figure 10:
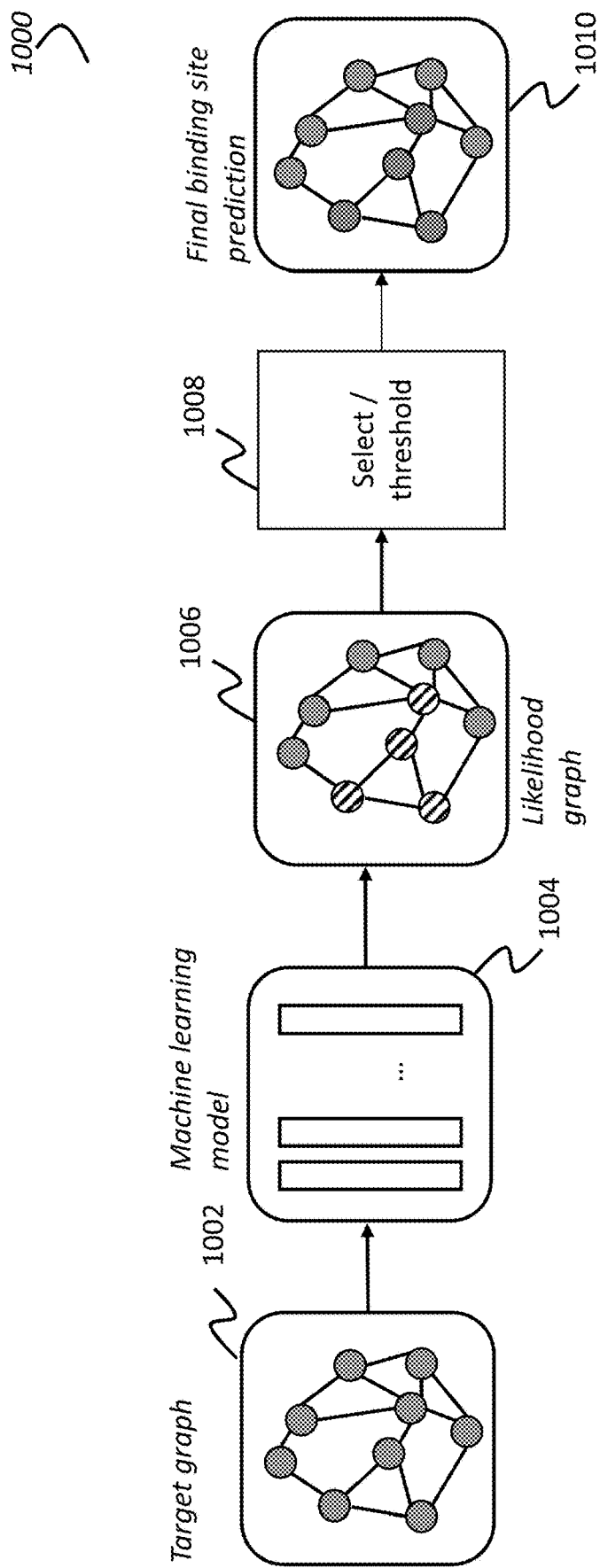
FIG. 10 is a block flow diagram of an example process for generating a binding site prediction, according to an illustrative embodiment.

For example, turning to FIG. 10, in certain embodiments, in certain example processes 1000 a GNN-based binding site predictor model 1004 may receive a target graph 1002 as input and generate, initially, a likelihood graph 1006, as output. A selection/thresholding step 1008 may then be used to generate a final binding site prediction, whereby likelihood values determined for each node are compared to a threshold value, and classified as binding sites or not, based on whether their likelihood values are above or below the threshold value.

C.iii Neural Network Architectures

In certain embodiments, a particular neural network model may comprise one or more (e.g., a plurality of) layers, including, for example, various transformer layers, graph convolutional layers, linear layers, etc. Each layer need not be of a same type, and various types of layers (e.g., transformer, graph convolutional, linear) may be combined in a particular neural network model.

Figure 11:
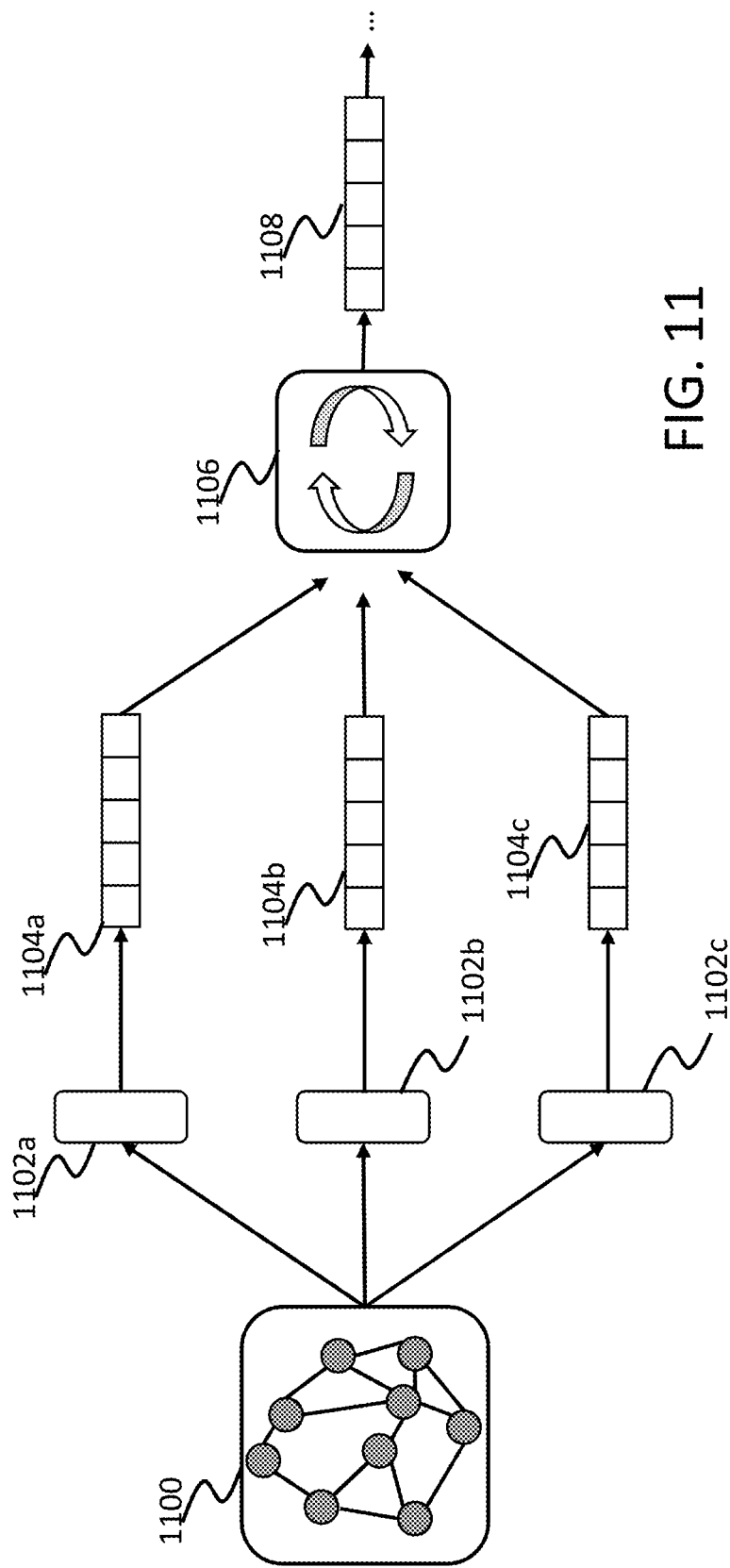
FIG. 11 is a schematic of an example multi-headed network architecture, used in certain embodiments.

Turning to FIG. 11, in certain embodiments, a neural network model may be a multi-headed model that utilizes multiple 'input heads'—parallel sets of neurons within each of one or more particular layers—to separately process different classes of interactions between amino acids. As opposed to 'attention heads' which are sets of neurons (learnable parameters) that receive the same input and generate a corresponding output, these 'input heads' operate on different inputs with each head specialized for its own particular kind of input. For example, in certain embodiments, a three-headed network model may be used in which each of one or more layers of a neural network model comprises three parallel sets of neurons, each associated with a different type of interaction. In certain embodiments, other approaches comprising more or less than three 'input heads' may be used. For example, each input head may be specialized for a certain edge type (e.g., where each input head has neurons/weights that are specialized on a specific edge type), and they can be concatenated or otherwise combined.

In this way, multiple input heads are allocated to receive different 'versions' of the same graph. For example, each version could include a certain subset of the edges in the graph, for example, and omit other edges. For example, in certain embodiments, a first set of neurons may, for example, evaluate, for each node, $k_1$ edges and corresponding neighbor nodes that represent the $k_1$ nearest neighbor amino acids. A second set of neurons may then be associated with, and process, for each node, $k_2$ edges and corresponding neighbor nodes that represent the interactions between $k_2$ nearest neighboring amino acids. Finally, a third set of neurons may then be associated with, and process, for each node, $k_3$ edges and corresponding neighbor nodes that represent the interactions between $k_3$ nearest neighboring amino acids. $k_1$, $k_2$, and $k_3$ may be integers, with $k_1 < k_2 < k_3$, (e.g., $k_1=8$, $k_2=16$, and $k_3=32$) such that the first set of neurons tends to be associated with short range interactions, the second set of neurons tends to be associated with intermediate range interactions, and the third set of neurons tends to be associated with long range interactions.

Additionally or alternatively, in certain embodiments various sets of neurons in a multi-headed network may be associated with different types of interactions between amino acids based on other criteria. For example, different sets of neurons may be associated with (i) peptide bond interactions, (ii) other intra-chain interactions (e.g., interactions between amino acids within a same molecule, but not directly connected by peptide bonds) within a particular molecule. Thus, for example, where two input heads are used, one input head might only consider edges that represent peptide bonds, and another input head only considers edges that represent intra-chain interactions. Where multiple chains are represented by an input graph, for example in the case of a biological complex model and/or where a target itself is or comprises a protein with multiple sub-units (e.g., where the protein exits in dimer, trimer, or other multimeric form), one head may consider inter-chain interactions, e.g., between amino acid sites on different molecules. Various combinations of multi-headed approaches may be used.

In certain examples, other ways of organizing/defining input heads are implemented according to what a particular input head is dedicated to. For example, there could be one or more input heads, each of which only considers edges that represent interactions between amino acid sites that are within a particular threshold distance of each other (e.g., a first input head for 5 angstroms or less, a second input head for 10 angstroms or less, and a third input head for 15 angstroms or less). In another example, there could be one or more input heads, each of which considers a first k (where k is an integer) edges that are the k nearest neighbors (e.g., a first input head that considers the 5 nearest neighbors, a second input head that considers the 15 nearest neighbors, and a third input head that considers the 30 nearest neighbors).

Furthermore, in an alternative embodiment, both inter and intra-chain interactions can be combined in one input head (receives both inter and intra chain edges), for example, with an additional value on the end of each edge feature vector that serves as a "chain label"—e.g., "1" if the edge is an inter-chain edge and "0" if the edge is an intra chain edge. Moreover, in certain embodiments, redundant information could be eliminated, thereby simplifying the task for the neural network. For example, backbone torsion angles have some redundancy according to the edge definitions—certain edges may be simplified by removing degrees of freedom, and certain angles may be computed using information about the orientation of neighboring amino acids. In certain embodiments, an edge feature vector may include a value that labels whether two nodes represent amino acids linked together via e.g., a covalent, peptide bond (e.g., immediately precede and/or follow each other in sequence).

The sets of edges considered by different input heads may be overlapping or non-overlapping sets. For example, a set of intra-chain edges and a set of inter-chain edges are generally non-overlapping, while a set of edges representing sites within 5 angstroms or less and a set of edges representing sites within 10 angstroms or less are overlapping (the second set includes the first). In certain embodiments, various input heads may be used in different combinations in a single machine learning model.

For example, in the schematic of FIG. 11, three 'input heads' are depicted 1102a. 1102b, and 1102c, where each input head receives and processes a portion of the edges of the target graph 1100 and generates output vectors 1104a, 1104b, and 1104c, allowing the processing of different ranges or scales of information. For example, input head 1102a may process edges associated with nodes representing amino acid sites within a first threshold distance, input head 1102b may process edges associated with nodes representing amino acid sites within a second threshold distance, and input head 1102c may process edges associated with nodes representing amino acid sites within a third threshold distance. At step 1106, the output may be concatenated, averaged, added, weighted, and/or otherwise processed to produce combined output vector 1108). In another example, for example where a target is or comprises a multiple sub-units and/or has a multimeric quaternary structure (e.g., a dimer, trimer) input head 1102a may process inter-chain edges, input head 1102b may process intra-chain edges, and input head 1102c may process edges that represent peptide bonds, i.e., connecting neighboring amino acid sites. At step 1106, the output may be concatenated, averaged, added, weighted, and/or otherwise processed to produce combined output vector 1108).

In certain embodiments, an ensemble machine learning model is created as a collection of multiple subsidiary machine learning models, where each subsidiary machine learning model receives input and creates output, then the outputs are combined (e.g., a voting model). For example, in certain embodiments, a voting ensemble machine learning model may be used wherein a likelihood value is an integer, such as a sum of votes of multiple machine learning models. For example, as applied in the method illustrated in FIG. 10, the values 1006 of predicted likelihood of being a binding site for each particular amino acid type, as determined by machine learning model 1004, may be integers representing sums of votes of multiple machine learning models in a voting ensemble machine learning model. Certain embodiments use different ways of combining subsidiary machine learning model output in a voting model. For example, a simple average may be taken, a weighted average may be taken (e.g., where some models are weighted more heavily than others), votes may be counted (e.g., integers), and the like.

D. Search Space Filtering and Refinement of Scaffold Docking Predictions

In certain embodiments, binding site predictions may be used to improve accuracy and/or computational efficiency of other biologic structure design and analysis modules and/or processes. For example, in certain embodiments, binding site predictions may be used to filter a landscape of prospective peptide backbones and poses thereof—a "scaffold-pose landscape" that is evaluated and searched through in order to identify favorable peptide backbones and poses, with respect to a target molecule, for use in designing a custom biologic, e.g., in-silico. Filtering a scaffold-pose landscape in this manner can, among other things, not only improve computational efficiency by reducing a size of a search space to be explored, but also improve quality of peptide backbones and poses identified, by e.g., conditioning the search space to be limited to and/or weighted towards those backbones and poses that place portions of a potential ligand in a position to interact with not just any portion of the target, but, in particular, predicted binding sites of the target.

D.i Scaffold Docking

For example, in certain embodiments, binding site predictions may be used together with a machine-learning-based scaffold docking technology to, among other things, design a custom biologic structure. Without wishing to be bound to any particular theory, scaffold docking technologies as described herein, and in further detail in U.S. Pat. No. 11,450,407, entitled "Systems and Methods for Artificial Intelligence-Guided Biomolecule Design and Assessment," issued Sep. 20, 2022, leverage a hierarchical approach to de novo biologic structure design, whereby representations of one or more candidate peptide backbone are placed in a variety of 3D orientations—i.e., poses—with respect to a target of interest and evaluated to identify a set of one or more particular backbones, and poses thereof, that are favorable to binding. A favorable peptide backbone and pose combination can then be used as a scaffold upon which to design a custom interface for binding to a target molecule.

Figure 12A:
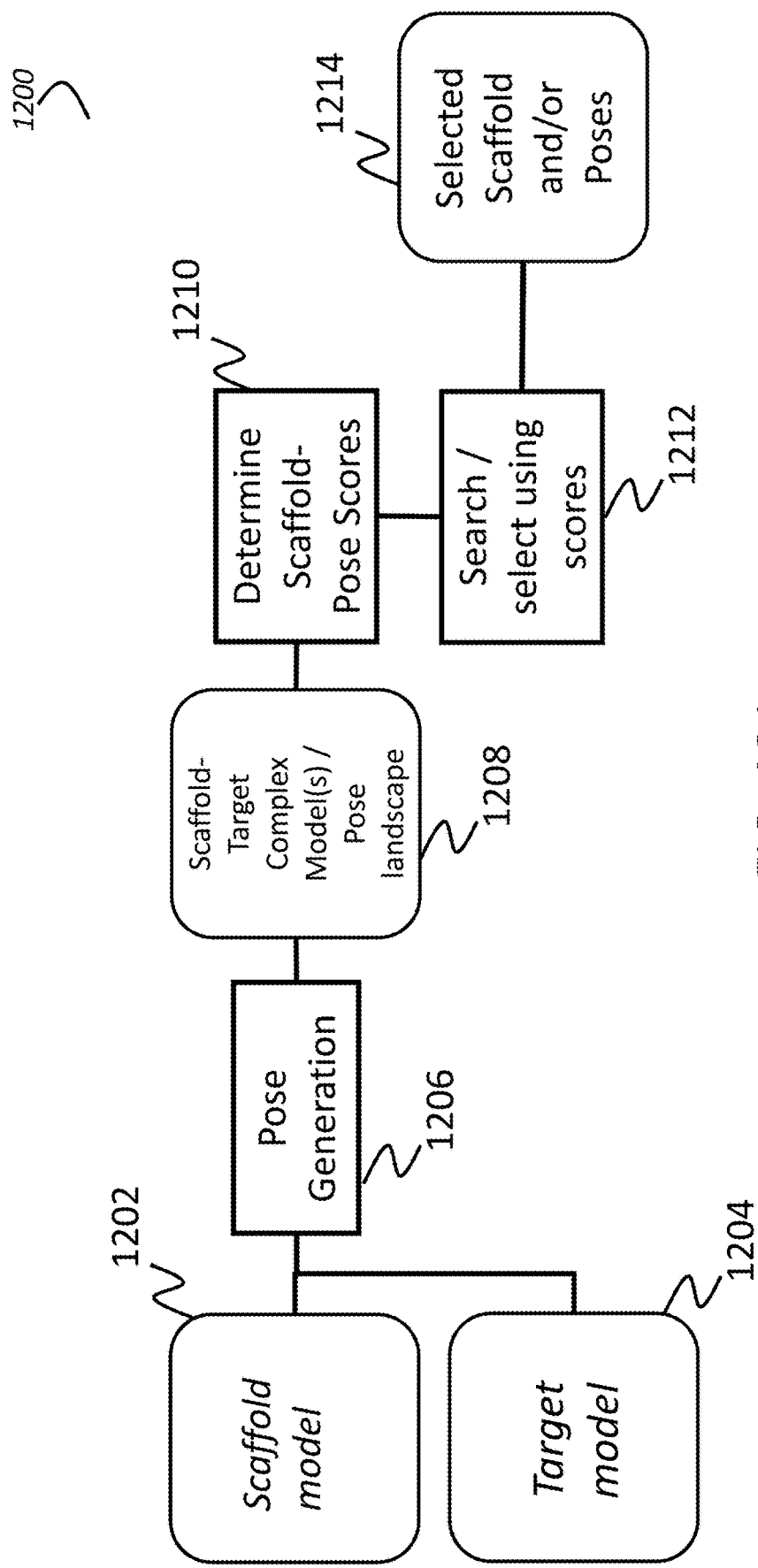
FIG. 12A is a block flow diagram of an example posegeneration and scaffold-scoring process, according to an illustrative embodiment.
Figure 12B:
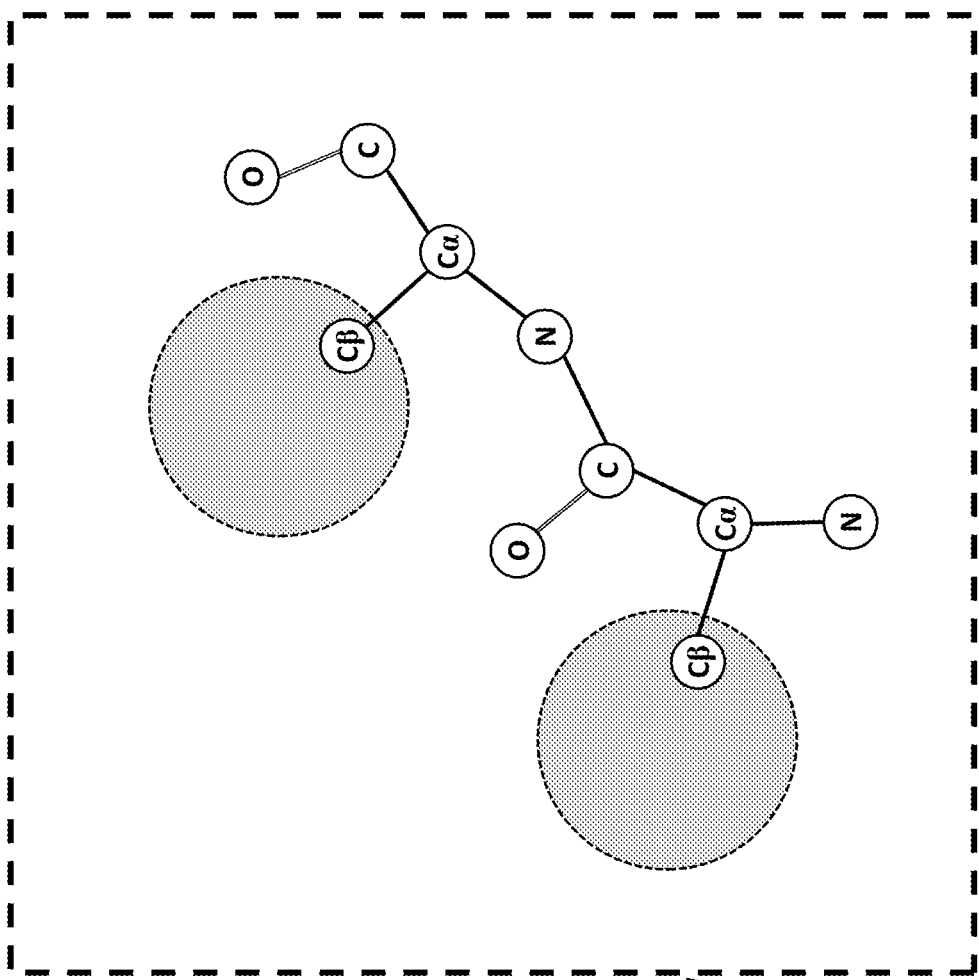
FIG. 12B is a schematic illustrating a scaffold model of a portion of a protein, according to an illustrative embodiment.
Figure 12B:
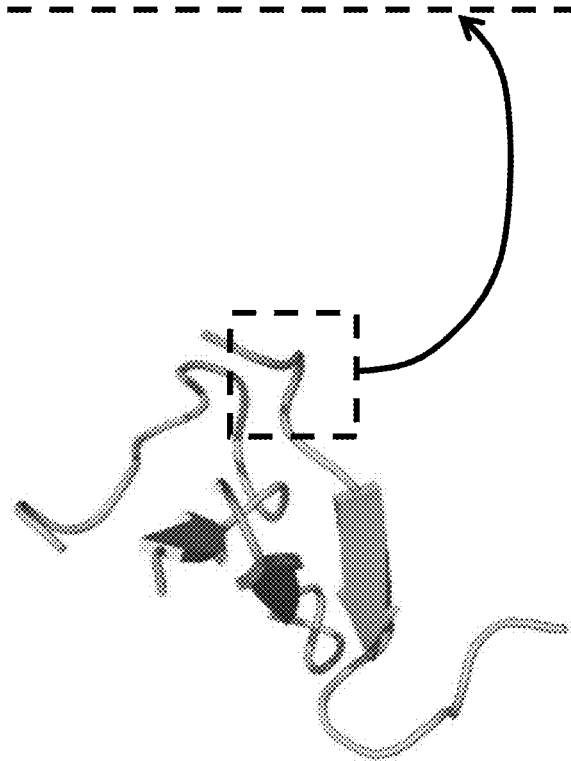

Turning to FIG. 12A, in certain embodiments, a scaffold-docking process 1200 represents a candidate peptide backbone using a scaffold model 1202, which represents three-dimensional locations (relative and/or absolute) and/or orientations of a peptide backbone, omitting amino acid side chains. For example, in certain embodiments, a scaffold model may include a 3D representation that specifies 3D locations of peptide backbone atoms, but omits—e.g., does not include a complete representation of—one or more atoms of each side chain. For example, as illustrated in FIG. 12B, in certain embodiments, a scaffold model may include, for each amino acid side chain, a placeholder, that can be used to represent an unknown and/or to-be-determined side chain (grey, dashed circles in the figure). In certain embodiments, each amino acid side chain in a scaffold model is represented by a first side chain atom, such as a CB. Use of a $C_\beta$, among other things, allows an unknown and/or to-be-determined side chain to be located.

Turning again to FIG. 12A, scaffold model 1202 may be combined with a target model 1204 that represents at least a portion of a target molecule. In certain embodiments, target model 1204 is or comprises a scaffold model. In certain embodiments, target model 1204 is not necessarily a scaffold model, and may include (e.g., complete representations of) amino acid side chains. Scaffold model 1202 may be placed and/or oriented in a variety of 3D poses with respect to target model 1204 to create multiple scaffold-target complex models 1208, each of which represents at least a portion of a biological complex comprises the particular candidate peptide backbone represented by scaffold model 1202, oriented at a particular pose with respect to the target molecule represented by target model 1204. In certain embodiments, poses are generated 1206 by applying a plurality of 3D translation and/or rotation operations to scaffold model 1204, to create a plurality of poses and, accordingly, scaffold-target complex model(s) 1208.

In certain embodiments, pose generation step 1206 includes one or more preliminary filtering steps to remove poses that are unlikely to produce physical results and/or do not place surface portions of the target and scaffold in sufficient proximity for interaction to occur. For example, pose generation step may exclude 3D rotations and translations that cause excessive, non-physical overlap between target and scaffold, for example, by determining, for each of one or more poses, whether they cause core atoms, beneath the surface of target and scaffold, to lie on top of each other. Additionally or alternatively, pose generation step may exclude poses that do not place surface atoms of scaffold and target into contact with each other, either at all, and/or sufficiently, as measured by various criteria. For example, in certain embodiments, during pose generation step 1206, shape maps are used to represent version of target model 1204 and scaffold model 1202 on a 3D grid, with each grid point within a particular volume (e.g., a van der Waals radius) about an atom of (i) the target or (ii) candidate peptide backbone represented by scaffold model 1202 encoded with a value based on a solvent accessible surface area for the atom. As described in further detail herein (e.g., below), and in U.S. Pat. No. 11,450,407, entitled "Systems and Methods for Artificial Intelligence-Guided Biomolecule Design and Assessment," issued Sep. 20, 2022, the content of which is incorporated herein in by reference in its entirety, among other things, this approach allows a cross-correlation operation to efficiently compute values that can be used to approximate whether a particular combination of rotation and translation operations cause clashes, lack of any contact, or insufficient contact and thereby filter out those poses that are unlikely to be found successful, before, e.g., more computational machine-learning based scoring is performed.

In certain embodiments, a machine learning model may be used to evaluate and score candidate peptide backbones and pose thereof by determining 1210 a scaffold-pose score for one or more scaffold-target complex model(s). In certain embodiments, for example, a scaffold-docker model may implement a machine learning algorithm that receives, as input, a scaffold-target complex model and/or another representation derived therefrom, and generates, as output, a scaffold-pose score that is indicative of a likelihood and/or favorability of the particular candidate peptide backbone and pose for binding with the target.

For example, a scaffold-docker model may be trained to differentiate between (i) representations of native complexes, that have been verified to exist, physically, and for which structures have been determined experimentally, and (ii) artificially generated variant complexes, that are altered, in-silico creations, that do not and/or are less likely to (e.g., in comparison with native complexes) actually exist and/or be viable, physically. In this manner, when a scaffold-docker model receives, as input, a new particular scaffold-target complex model representing a prospective candidate peptide backbone in complex with a target, a scaffold-pose score determined for the particular scaffold-target complex model may indicate and/or quantify a level of similarity (or dissimilarity) between the particular scaffold-target complex model and representations of native complexes presented during training. Accordingly, a determined scaffold-pose score can provide a measure of likelihood that the prospective candidate peptide backbone and pose it is oriented at with respect to the target will be viable.

Figure 13B:
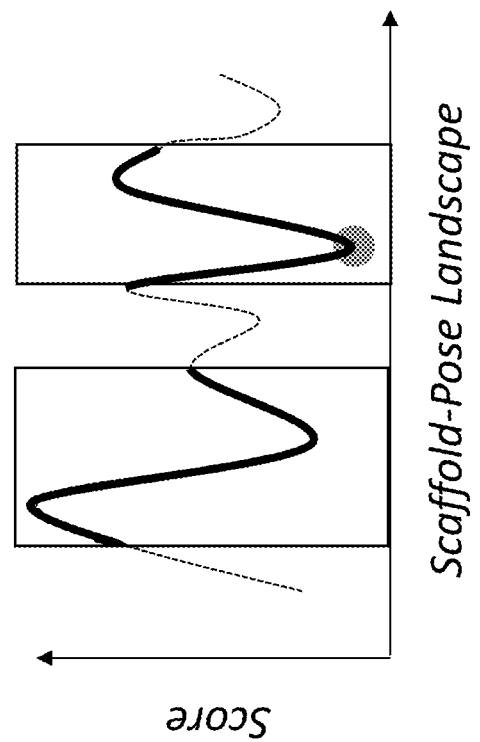
FIG. 13B is a graph illustrating a filtered version of the example scaffold-pose landscape shown in FIG. 13A, according to an illustrative embodiment.
Figure 13A:
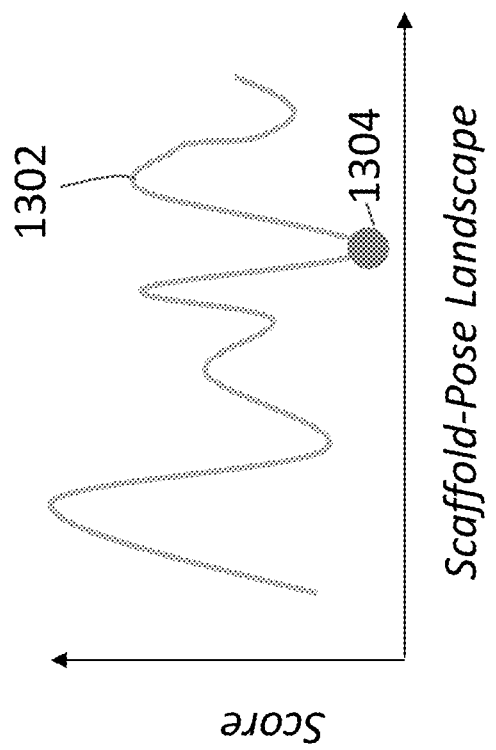
FIG. 13A is a graph illustrating an example scaffold-pose landscape, according to an illustrative embodiment.

Scaffold-pose scores may be determined 1210 for each, or at least a portion of, scaffold target complex model(s) 1208 in order to score scaffold-poses across a landscape 1302, for example as illustrated in FIG. 13A. Landscape 1302 may be searched, to identify and select 1212 one or more scaffold-target complex models 1214, based on their computed scaffold-pose scores. Various techniques may be used to search a scaffold-pose landscape 1302 and select, from a set of candidate scaffold-target complex models, a subset of one or more scaffold-target complex model(s) based on their respective scaffold-pose scores. In certain embodiments, an exhaustive, brute force, search approach may be used, wherein a score is determined for each scaffold-target complex model 1208 is determine 1210 and, for example, one or more optimal (e.g., highest or lowest scoring 1304) scaffold-target complex model(s) selected. In certain embodiments, an optimization routine, such as simulated annealing, may be used, with the (e.g., machine learning based) scoring function 1210 used as an objective function to be minimized and/or maximized.

FIG. 12A shows pose generation step 1206, scaffold-pose scoring step 1210 and search/selection step 1212 as different blocks, but it should be understood that these steps may operate in tandem, with certain operations performed in parallel and/or partially overlapping, and/or may be iterated over multiple times. For example, as described in further detail herein, in certain embodiments, pose generation step 1206 may generate one or more (e.g., a plurality) of vectors (or tuples), each vector, $p_i$, having a form $p_i = \{r_i, t_i\}$ where $r_i$ represents a 3D rotation and $t_i$ a 3D translation, such that each pose vector, $p_i$, represents a particular pose. Together with a scaffold model and a target model, each pose vector may, accordingly, be used represent a scaffold-target complex model and/or create a 3D volumetric representation, such as an electron density map (EDM), a scaffold-target graph, or other representation for use as input to a machine learning model used as a scoring function for evaluating scaffold-target complex models.

In certain embodiments, pose generation step 1206 may create a landscape of poses for a particular scaffold-target combination, represented, e.g., as a plurality of pose vectors. A particular representation, such as a 3D volumetric representation, that is used as input for a machine learning model used as a scoring function at step 1201, may be generated (e.g. using a particular pose vector, scaffold model 1202, and target model 1204) for each pose up as an initial step (e.g., up front, prior to searching), or may be generated on the fly, as needed. For example, in certain embodiments, search/ selection step 1212 may utilize an iterative optimization algorithm, such as simulated annealing, whereby one or more scaffold-target complex models are scored and, based on the results, used to move to a new position in the pose/scaffold-target complex model landscape and select new scaffold-target complex models to evaluate at a subsequent iteration. In certain embodiments, having scaffold model 1202, target model 1204, and a landscape (i.e., a plurality) of pose vectors stored in memory or otherwise accessible, an optimization technique used to implement search/selection step 1212 may generate input representations (e.g., 3D volumetric representations, such as EDMs, scaffold-target graph representations, etc.) for a scoring machine learning model on the fly, as needed at a particular iteration. Accordingly, in certain embodiments, only a portion of the landscape of scaffold target complex models 1208 may be used as or to create input for a machine learning model and scored.

In certain embodiments, once particular candidate peptide backbones and poses have been identified, they may be used, among other things, in downstream processes to generate custom biologics for binding to the target. For example, in certain embodiments, a subsequent, interface designer module may receive and/or access scaffold-target models, and/or particular scaffold models and poses represented thereby, identified and selected by scaffold-docking process 1200. Interface portions of a scaffold that are in proximity to the target may then be populated with amino acids (i.e., particular side chains) to design full amino acid interfaces for binding to the target. In certain embodiments, machine learning-based techniques, several of which are described in detail in U.S. Pat. No. 11,450,407, entitled "Systems and Methods for Artificial Intelligence-Guided Biomolecule Design and Assessment," issued Sep. 20, 2022, U.S. application Ser. No. 17/871,425, entitled, "Systems and Methods for Artificial Intelligence-Based Prediction of Amino Acid Sequences at a Binding Interface," filed Jul. 22, 2022, and U.S. Provisional Application No. 63/359,732, entitled "Systems and Methods for Generative Neural Network-Based Design of Custom Biologics," filed Jul. 8, 2022, the content of each of which is incorporated by reference herein in its entirety. In this manner, a scaffold-docking approach may be used to identify candidate peptide backbones and particular poses thereof to serve as scaffolds, to be populated with amino acid side chains, for designing a custom binder.

D.ii Preliminary Scoring and Filtering of Candidate Poses Based on Binding Site Predictions In certain embodiments, predictions of binding sites can be used to filter certain scaffold-pose combinations of a landscape, to exclude and/or emphasize (e.g., weight) particular scaffold-pose combinations. Binding site predictions may, for example, be used to exclude certain portions of a scaffold-pose landscape based on whether they place portions of a candidate peptide backbone in sufficient proximity to binding sites of a target, as illustrated in FIG. 13B.

Figure 14A:
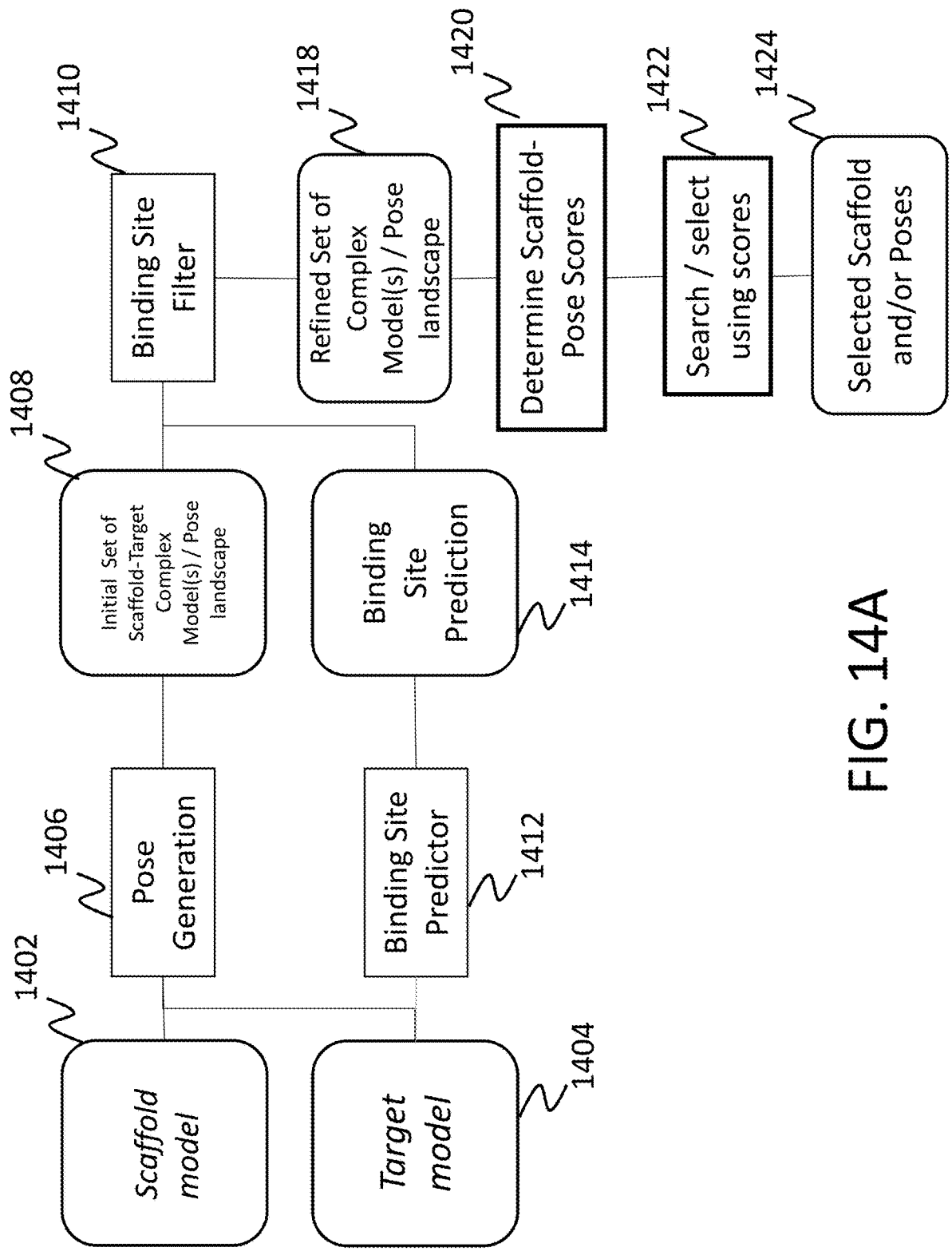
FIG. 14A is a block flow diagram of an example process for refining a landscape of poses using a binding site prediction, according to an illustrative embodiment.

Turning to FIG. 14A, in certain embodiments, a scaffold docking process such as process 1400 may include a filtering step whereby a binding site prediction is generated, received, accessed, or otherwise obtained, and used to create a refined set of scaffold-target complex models. Similar to process 1200, a scaffold model 1402 may be used to represent a prospective candidate peptide backbone, and combined with target model 1404 at a pose generation step 1406 to create an initial set of prospective poses 1408.

In certain embodiments, before proceeding to score and search a scaffold-pose landscape, initial set of prospective poses 1408 may be filtered 1410 using a binding site prediction 1414 that identifies and/or scores one or more binding sites of target molecule. In certain embodiments, binding site prediction may be generated, for example, from target model using a binding site predictor model 1412 as described herein. In certain embodiments, a binding site prediction 1414 may be accessed, received, or otherwise obtained. Binding site prediction 1414 may be used to filter 1410 initial set of prospective poses 1408, for example, to identify poses that position and/or orient portions of scaffold-model 1402 in positions to interact with one or more binding sites of the particular target molecule, as identified by binding site prediction 1414.

For example, in certain embodiments, binding site prediction 1414 may be used to determine whether a particular pose places one or more side chains of scaffold model 1402 in sufficient proximity to a binding site. For example, filtering step 1410 may determine whether a particular pose places one or more atoms of scaffold model within a (e.g., pre-defined) threshold distance from one or more binding sites. In certain embodiments, one or more binding site filter metrics may be computed to quantify an extent to which binding sites are involved.

As described above with respect to FIG. 12A, various steps may be performed together, e.g., in parallel and/or in an iterative fashion. In certain embodiments, initial set of scaffold-target complex models may be or comprise an initial pose landscape, represented, for example, as one or more (e.g., a plurality of) pose vectors, $p_i$, as described above. Binding site filter 1410 may, accordingly, be used to filter the initial pose landscape, retaining a subset of those poses (e.g., pose vectors) that satisfy various binding site involvement criteria as described above. As described above with respect to FIG. 12A, a filtered scaffold-pose landscape (e.g., as illustrated in FIG. 13B) may be searched in a variety of fashions, e.g., via exhaustive brute force approaches (e.g., scoring each scaffold-target complex model) or in an iterative fashion, such as via a simulated annealing or other approach, whereby each point in a filtered landscape is not necessarily scored, and representations of scaffold-target complex models (e.g., volumetric representations; e.g., graph representations) are generated on the fly, on an as-needed basis.

Figure 14B:
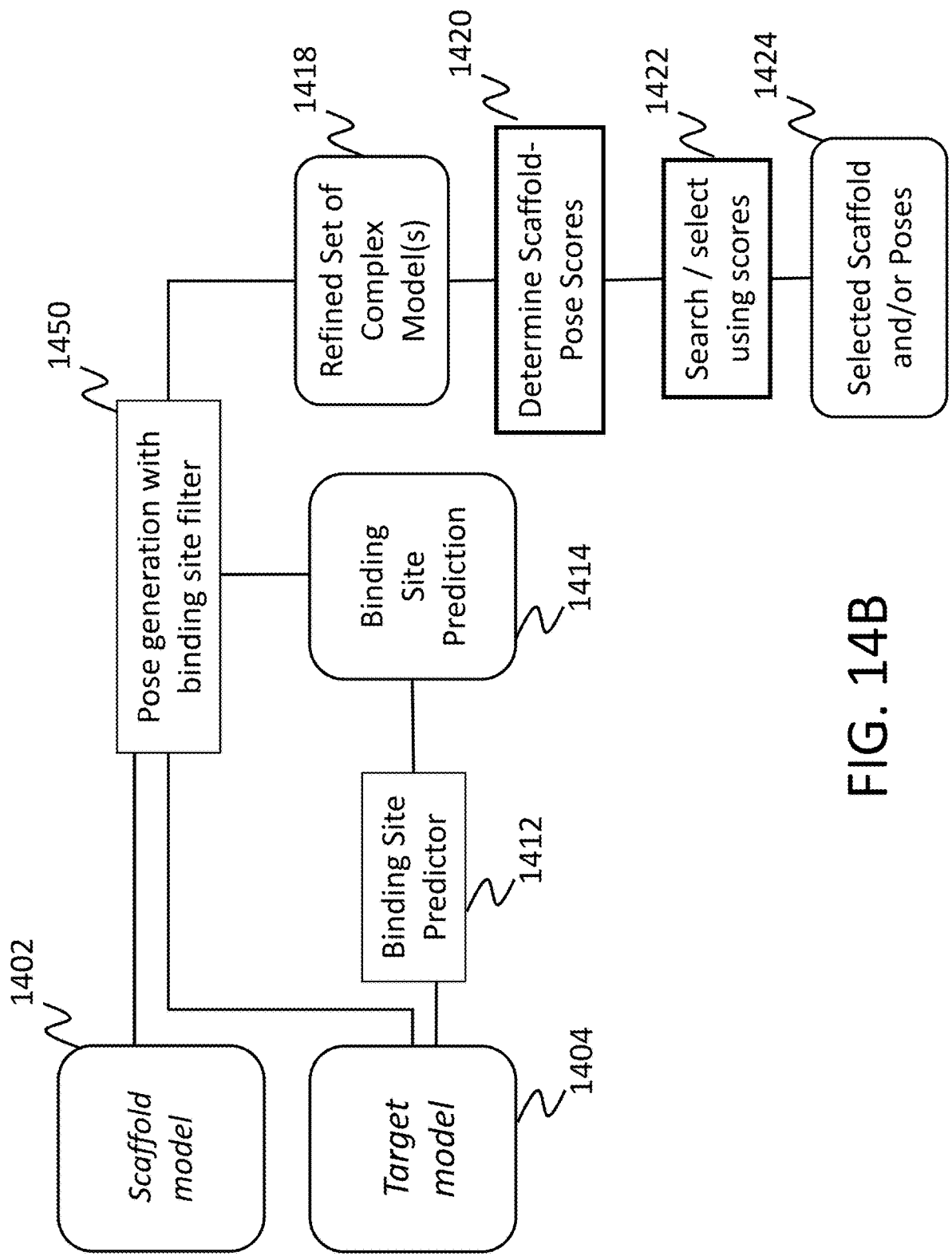
FIG. 14B is a block flow diagram of another example process for refining a landscape of poses using a binding site prediction, according to an illustrative embodiment.

In certain embodiments, binding site filter step 1410 may be implemented as a special pose generation step, whereby a landscape of poses is generated using a modified target representation based on binding site prediction 1414. For example, as described in further detail here, pose generation step 1406 may utilize various representations, such as shape map representations, of scaffold-target complex models to rapidly identify poses that satisfy various criteria, such as placing a sufficient number of atoms of a scaffold and target in proximity (e.g., a level of contact), avoiding non-physical levels of overlap (e.g., placing scaffold and target excessively on top of each other, in a non-physical fashion, referred to herein as "clashes"), etc. In certain embodiments, binding site filtering step may be implemented using similar approaches, but, for example, using a representations of target that, for example emphasize binding sites and/or de-emphasize or exclude other portions of the target. In certain embodiments, binding site filter step 1410 and pose generation step 1406 may be combined into a single pose generation step 1450 that includes a binding site filtering approach, for example as illustrated in FIG. 14B, whereby generated poses are generated and filtered according to criteria such as presence of contact and/or avoidance of clashes, as well as involvement of binding sites, simultaneously and/or in parallel.

Shape Map Representation and Filtering

Figure 15A:
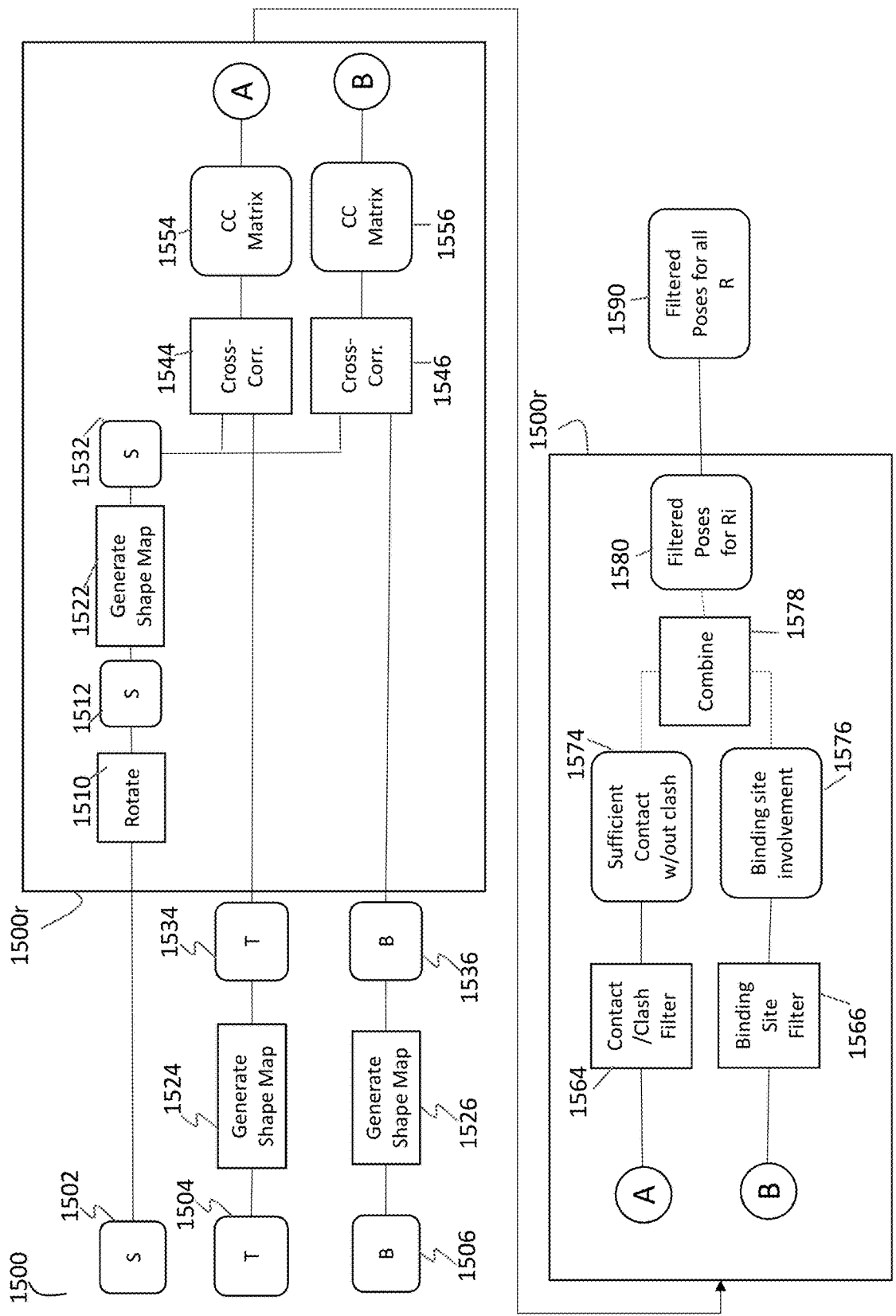
FIG. 15A is a block flow diagram of an example process for using a shape map representation and cross-correlation method for generating candidate poses, according to an illustrative embodiment.
Figure 15C:
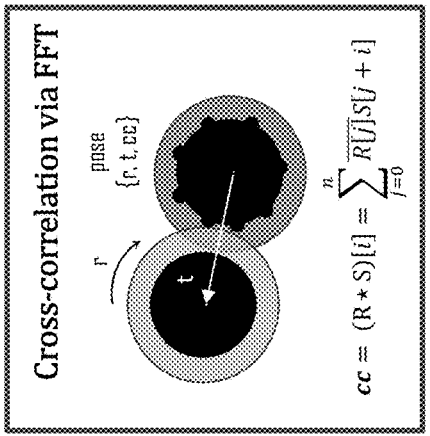
FIG. 15C is a schematic illustrating cross-correlation of two shape maps, according to an illustrative embodiment.
Figure 15B:
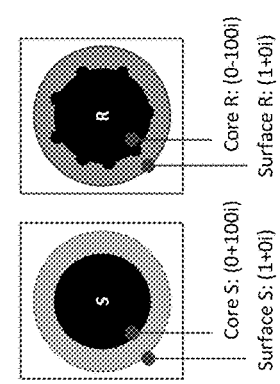
FIG. 15B is a schematic showing example shape map representations of a scaffold model and a target, comprising side chains, according to an illustrative embodiment.

Turning to FIGS. 15A-C, in certain embodiments, binding site filtering step 1410 may use and/or be implemented to be compatible with a shape map approach, as described herein and in U.S. Pat. No. 11,450,407, entitled "Systems and Methods for Artificial Intelligence-Guided Biomolecule Design and Assessment." issued Sep. 20, 2022, the content of which is incorporated by reference in its entirety. For example, FIGS. 15A-C illustrate an example process 1500 whereby target and scaffold models are represented via shape maps—matrices (e.g., 3D matrices or tensors) of complex numbers—and an efficient cross-correlation approach is used to identify poses that are predicted to place molecule surfaces in sufficient proximity for binding, and filter out those poses that are likely to create non-physical contact and/or place a scaffold and target too far apart for binding to occur. Example process 1500 illustrates how a binding site prediction can be incorporated, to generate a binding site shape map, which is modified version of target shape map that includes atoms of binding sites and buried/core sites, but excludes non-binding surface sites. Binding site shape map may then be used in connection with a second cross-correlation step, to filter out those poses that do not place atoms of scaffold model in proximity with, in particular, binding sites of target model.

In particular, in certain embodiments, shape-map-based pose generation process 1500 generates 1524 a shape map representation—a target shape map 1534—from target model 1504. In certain embodiments, as shown in FIG. 15B, a shape map representation may be created from a particular structural model of a biological molecule, such as, e.g., a protein, by labeling each atom in the particular structural model as a surface or core according to, for example, a solvent-accessible surface area (SASA) value. In certain embodiments, SASA may, e.g., for purposes of generating a shape map representation, be calculated in a same fashion (e.g., using a same computational method) as described above with respect to determining surface sites, but on an atom-by-atom (e.g., as opposed to site level) basis. A shape map representation may then be created by representing the particular structure as centered on a three-dimensional grid (e.g., matrix), and for each labelled atom, assigning a complex number to grid points within a pre-defined radius (e.g., surrounding the atom). In certain embodiments, a predefined radius for a particular atom is, or is based on, a Van Der Waals radius for the particular atom. In certain embodiments, a particular complex number assigned to grid points associated with a particular atom is determined based on a label of the particular atom—for example, one number (e.g., a purely complex number, such as 0±100i) assigned for grid points associated with core atoms and another number (e.g., a purely real number, such as 1+0i) assigned for grid points associated with surface atoms.

In this manner, target shape map 1534 may be created from target model 1504. Scaffold model 1502 may then be rotated via a rotation, $\{r\}$. 1510 to create a rotated scaffold model 1512, from which a shape map representation—rotated scaffold shape map 1532—is then created 1522.

In certain embodiments, rotated scaffold shape map 1532 and target shape map 1534 are then cross-correlated 1544. In certain embodiments, cross-correlation 1544 is performed via a Fast Fourier Transform (FFT). In certain embodiments, cross correlation scans rotated scaffold shape map 1532 and target shape map 1534 across each other, calculating a cross-correlation value at each of a plurality of particular translations $\{t\}$ of rotated scaffold shape map 1532 relative to target shape map 1534, generating a scaffold-target cross correlation matrix 1554. In this manner, for a particular rotation $\{r\}$, cross-correlation 1544 samples a range of possible translations, computing, for each relative translation, $t_i$, of rotated scaffold shape map 1532 relative to target shape map 1534, a corresponding cross-correlation value, according to equation (1), below and illustrated in FIG. 15C, $$cc = (T^*S)[i] = \Sigma_{j=0}^n \overline{T[j]} S[j+i], \qquad (1)$$

where T is a target shape map and S is a rotated scaffold shape map. Accordingly, in certain embodiments, cross correlation step 1544 creates, as cross-correlation matrix, a 3D grid (e.g., a matrix) of cross-correlation (cc) values, each cc value corresponding to a value computed for a different translation of a same rotated scaffold.

Figure 15D:
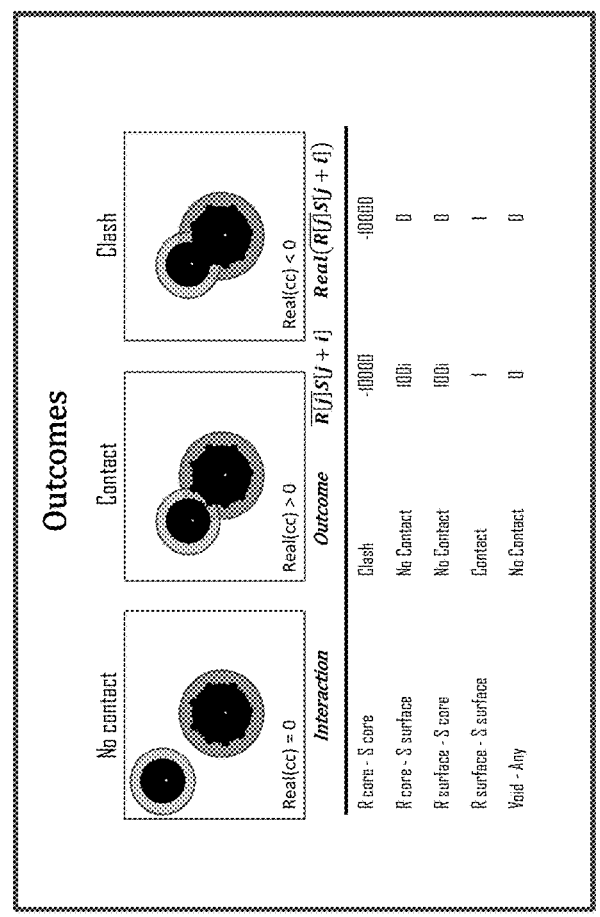
FIG. 15D is a schematic illustrating how relative positioning and/or orientation of two shape maps may influence an argument of a cross-correlation operation, according to an illustrative embodiment.

As illustrated in FIG. 15D, a computed cc value can be used as a metric to determine which poses (e.g., rotation-translation combinations) result in sufficient levels of interaction (e.g., contact) between the scaffold and target and to filter out undesirable poses that would cause non-physical overlap, referred to as "clashes" and/or a lack of contact between the scaffold and target. For example, as shown in FIG. 15B and described herein, grid points of scaffold and target shape maps can be assigned numerical values that distinguish whether they are associated with (e.g., falling within a van der Waals radius of) core or surface atoms. For example, grid points of scaffold shape map that are associated with surface atoms may be assigned a small real-valued number, such as 1+0i, and grid points that are associated with core atoms may be assigned a large, purely imaginary value, such as 0+100i. Grid points of target shape map may be labeled similarly, but using a complex conjugate version of the labeling scheme used for scaffold shape map, such that core atoms are assigned a large negative, purely imaginary value. As a result, when a complex conjugate value is computed, e.g., via equation (1) above, overlap between grid points of various types of atoms may contribute different types—e.g., large negative real values, purely imaginary values, or small positive values—to the argument in the summation of equation (1). Table 1, below, summarizes different interaction types and resultant values of the argument of the summation in equation (1), as well as its real part, and FIG. 15D illustrates, accordingly, how the real part of a computed cc value can be used to infer whether a particular pose represented by a particular rotation-translation pair would result in one of three outcomes—no contact, contact, or a clash.

TABLE 1

Shape Model Interactions, Outcomes, and Overlap Values

| Interaction | Outcome | T[j]S[j + i] | Real (T[j]S[j + i]) |
|---|---|---|---|
| $T_{core}$-$S_{core}$ | Clash | −10,000 | −10,000 |
| $T_{core}$-$S_{surface}$ | No Contact | 100i | 0 |
| $T_{surface}$-$S_{core}$ | No Contact | 100i | 0 |
| $T_{surface}$-$S_{surface}$ | Contact | 1 | 1 |
| Void-Any | No Contact | 0 | 0 |

As illustrated in FIG. 15D, a no contact outcome indicates that a complex model formed by orienting scaffold model according to the particular rotation translation pair with respect to receptor model would place it and a target too far apart for binding to be feasible (e.g., sufficiently likely). In certain embodiments, a no contact outcome can be identified via a cross-correlation value having a real part equal to zero. In certain embodiments, clash outcomes have a large real negative contribution to their corresponding cross-correlation value, while contact outcomes have small real positive contribution. As illustrated in FIG. 15D, clash outcomes indicate placements of a scaffold model and a receptor model that cause excessive overlap, which would also not likely result in a viable complex. Contact outcomes are indicative of poses that place a scaffold model in sufficient proximity (e.g., not necessarily perfect physical contact) to a receptor model to correspond to a complex with potential for binding to occur. Accordingly, contact outcomes are desirable, while clashes and no contact outcomes are not. Accordingly, in certain embodiments, {r,t} pairs that result in clash and/or no contact outcomes are filtered out 1564, and only contact outcomes are retained 1574. In certain embodiments, contact/clash filtering step 1564 may compare a real part of cc value from matrix 1554 with a threshold value, to filter out poses that do not generate a sufficient number of contact points. In certain embodiments a threshold value may be determined empirically, for example by evaluating cross-correlation values obtained from shape map representations of successful native complex models. For example, in one embodiment described in U.S. Pat. No. 11,450,407, entitled "Systems and Methods for Artificial Intelligence-Guided Biomolecule Design and Assessment," issued Sep. 20, 2022, it was found that an empirically determined threshold of 1100 captured 90% of native poses and could be used to retain high quality test poses.

In certain embodiments, additionally or alternatively, a binding site prediction 1506 can be used to generate 1526 a binding site shape map 1536. In certain embodiments, binding site shape map 1536 is a version of target shape map that emphasizes grid points that are associated with surface atoms that are part of binding sites. Binding site shape map 1536 may, for example, include only surface sites that are identified as binding sites, for example setting values of grid points associated with other, non-binding, surface sites to zero. Binding site shape map may then be cross-correlated 1546 with rotated scaffold shape map to create a binding site cross-correlation matrix, via same or similar operations described herein with respect to scaffold-target cross-correlation matrix 1556. Since binding site shape map only includes binding sites, a positive real value of the binding site cc value computed for a particular pose indicates contact between a surface atom of scaffold shape map and a binding site of target molecule. Accordingly, binding site involvement filter 1566 may, for example, retain only those poses that yield a positive real cross-correlation value 1576.

In certain embodiments, a final set of filtered poses 1580 is determined using one or both of (i) a set of poses determined to generate sufficient contact 1574 and (ii) a set of poses determined to involve one or more predicted binding sites of the target molecule. For example, filtered poses 1580 may be determined based on a combination 1578, e.g., as an intersection, union, or other function, of sets 1574 and 1576.

Accordingly, in this manner, for a particular rotation, a set of filtered poses can be generated. In certain embodiments, as illustrated in FIG. 15A, steps shown in block 1500r can be iteratively applied to multiple rotations to generate, for each rotation, a set of filtered poses. Sets of filtered poses generated in this manner can then be combined to create a final set of filtered poses for multiple rotations and translations 1590.

Turning again to FIG. 14A and FIG. 14B, a filtered set of poses, determined to involve one or more binding sites, may then be used to create a refined set of scaffold-target complex model(s) 1418, which may then be scored 1420 and searched 1422 to identify and select a subset 1424 to use for designing a custom interface, as described herein, for example above, with respect to FIG. 12A.

This approach provides benefits both in terms of generating scaffolds that are more likely to be successful as well as computational efficiency. First, it improves the quality of scaffolds selected by the scaffold-docker module in the sense that they are believed to be more favorable for designing a tight binding interface. In particular, use of binding site predictions allows scaffold docking to weight/favor poses that place potions of the scaffold in proximity to and/or at favorable orientations with respect to particular portions of the target that are known and/or predicted to be amenable to binding. For example, among other things, surfaces of a protein tend to be electrostatic and polar (e.g., hydrophilic), as they are in contact with water. Portions of a protein that participate in binding, and interact with other proteins, however, are hydrophobic, with rims of interfaces tending to be implicated in hydrogen bonding, and having charged residues. Among other things, Applicant discovered that poses generated by a scaffold docker may include poses created interfaces that included regions of targets that were electrostatic and polar. Recognizing that certain portions of proteins are better suited for binding than others, Applicant found that by using binding site predictions to effectively weight or filter a search space, causing a scaffold docker to focus on those poses that produced interfaces that included binding sites of the target, improved results were obtained—conditions the scaffold docker/space it explores to generate better poses.

Moreover, second, filtering the search space explored provides computational benefits as well. Searching a landscape requires scoring a large number of backbones and poses thereof using a machine learning model, and therefore is computationally expensive. A binding site prediction can be generated once, for a target, and stored. By reducing the number of runs of the machine learning model, computational efficiency can then be dramatically improved.

E. Computer System and Network Environment

Figure 16:
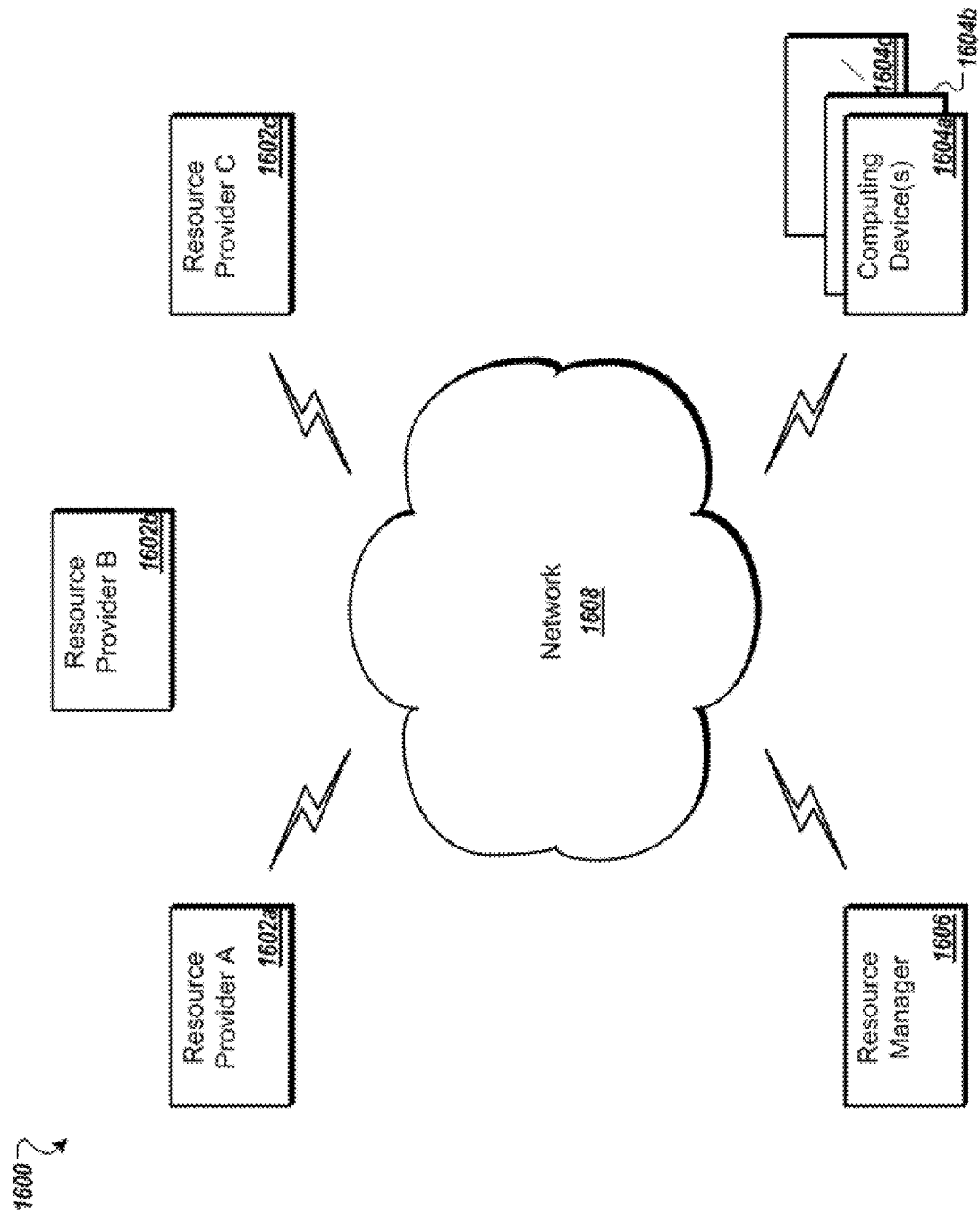
FIG. 16 is a block diagram of an exemplary cloud computing environment, used in certain embodiments.

Turning to FIG. 16, an implementation of a network environment 1600 for use in providing systems, methods, and architectures as described herein is shown and described. In brief overview, referring now to FIG. 16, a block diagram of an exemplary cloud computing environment 1600 is shown and described. The cloud computing environment 1600 may include one or more resource providers 1602a, 1602b, 1602c (collectively, 1602). Each resource provider 1602 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 1602 may be connected to any other resource provider 1602 in the cloud computing environment 1600. In some implementations, the resource providers 1602 may be connected over a computer network 1608. Each resource provider 1602 may be connected to one or more computing device 1604a, 1604b, 1604c (collectively, 1604), over the computer network 1608.

The cloud computing environment 1600 may include a resource manager 1606. The resource manager 1606 may be connected to the resource providers 1602 and the computing devices 1604 over the computer network 1608. In some implementations, the resource manager 1606 may facilitate the provision of computing resources by one or more resource providers 1602 to one or more computing devices 1604. The resource manager 1606 may receive a request for a computing resource from a particular computing device 1604. The resource manager 1606 may identify one or more resource providers 1602 capable of providing the computing resource requested by the computing device 1604. The resource manager 1606 may select a resource provider 1602 to provide the computing resource. The resource manager 1606 may facilitate a connection between the resource provider 1602 and a particular computing device 1604. In some implementations, the resource manager 1606 may establish a connection between a particular resource provider 1602 and a particular computing device 1604. In some implementations, the resource manager 1606 may redirect a particular computing device 1604 to a particular resource provider 1602 with the requested computing resource.

Figure 17:
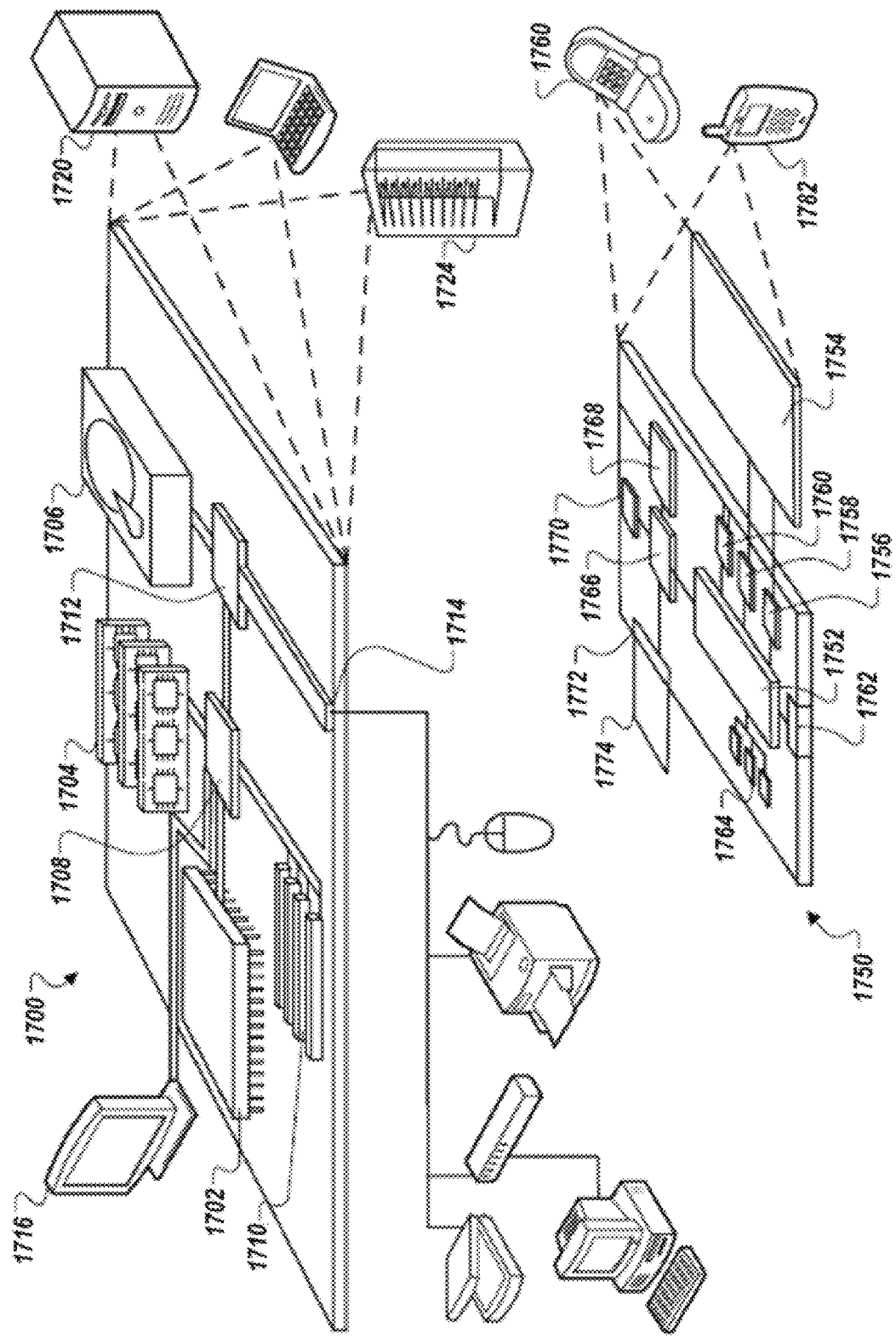
FIG. 17 is a block diagram of an example computing device and an example mobile computing device, used in certain embodiments.

FIG. 17 shows an example of a computing device 1700 and a mobile computing device 1750 that can be used to implement the techniques described in this disclosure. The computing device 1700 is intended to represent various forms of digital computers, such as laptops, desktops, workstations, personal digital assistants, servers, blade servers, mainframes, and other appropriate computers. The mobile computing device 1750 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 1700 includes a processor 1702, a memory 1704, a storage device 1706, a high-speed interface 1708 connecting to the memory 1704 and multiple high-speed expansion ports 1710, and a low-speed interface 1712 connecting to a low-speed expansion port 1714 and the storage device 1706. Each of the processor 1702, the memory 1704, the storage device 1706, the high-speed interface 1708, the high-speed expansion ports 1710, and the low-speed interface 1712, are interconnected using various busses, and may be mounted on a common motherboard or in other manners as appropriate. The processor 1702 can process instructions for execution within the computing device 1700, including instructions stored in the memory 1704 or on the storage device 1706 to display graphical information for a GUI on an external input/output device, such as a display 1716 coupled to the high-speed interface 1708. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system). Thus, as the term is used herein, where a plurality of functions are described as being performed by "a processor", this encompasses embodiments wherein the plurality of functions are performed by any number of processors (one or more) of any number of computing devices (one or more). Furthermore, where a function is described as being performed by "a processor", this encompasses embodiments wherein the function is performed by any number of processors (one or more) of any number of computing devices (one or more) (e.g., in a distributed computing system).

The memory 1704 stores information within the computing device 1700. In some implementations, the memory 1704 is a volatile memory unit or units. In some implementations, the memory 1704 is a non-volatile memory unit or units. The memory 1704 may also be another form of computer-readable medium, such as a magnetic or optical disk.

The storage device 1706 is capable of providing mass storage for the computing device 1700. In some implementations, the storage device 1706 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 1702), perform one or more methods, such as those described above. The instructions can also be stored by one or more storage devices such as computer- or machine-readable mediums (for example, the memory 1704, the storage device 1706, or memory on the processor 1702).

The high-speed interface 1708 manages bandwidth-intensive operations for the computing device 1700, while the low-speed interface 1712 manages lower bandwidth-intensive operations. Such allocation of functions is an example only. In some implementations, the high-speed interface 1708 is coupled to the memory 1704, the display 1716 (e.g., through a graphics processor or accelerator), and to the high-speed expansion ports 1710, which may accept various expansion cards (not shown). In the implementation, the low-speed interface 1712 is coupled to the storage device 1706 and the low-speed expansion port 1714. The low-speed expansion port 1714, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 1700 may be implemented in a number of different forms, as shown in the figure. For example, it may be implemented as a standard server 1720, or multiple times in a group of such servers. In addition, it may be implemented in a personal computer such as a laptop computer 1722. It may also be implemented as part of a rack server system 1724. Alternatively, components from the computing device 1700 may be combined with other components in a mobile device (not shown), such as a mobile computing device 1750. Each of such devices may contain one or more of the computing device 1700 and the mobile computing device 1750, and an entire system may be made up of multiple computing devices communicating with each other.

The mobile computing device 1750 includes a processor 1752, a memory 1764, an input/output device such as a display 1754, a communication interface 1766, and a transceiver 1768, among other components. The mobile computing device 1750 may also be provided with a storage device, such as a micro-drive or other device, to provide additional storage. Each of the processor 1752, the memory 1764, the display 1754, the communication interface 1766, and the transceiver 1768, are interconnected using various buses, and several of the components may be mounted on a common motherboard or in other manners as appropriate.

The processor 1752 can execute instructions within the mobile computing device 1750, including instructions stored in the memory 1764. The processor 1752 may be implemented as a chipset of chips that include separate and multiple analog and digital processors. The processor 1752 may provide, for example, for coordination of the other components of the mobile computing device 1750, such as control of user interfaces, applications run by the mobile computing device 1750, and wireless communication by the mobile computing device 1750.

The processor 1752 may communicate with a user through a control interface 1758 and a display interface 1756 coupled to the display 1754. The display 1754 may be, for example, a TFT (Thin-Film-Transistor Liquid Crystal Display) display or an OLED (Organic Light Emitting Diode) display, or other appropriate display technology. The display interface 1756 may comprise appropriate circuitry for driving the display 1754 to present graphical and other information to a user. The control interface 1758 may receive commands from a user and convert them for submission to the processor 1752. In addition, an external interface 1762 may provide communication with the processor 1752, so as to enable near area communication of the mobile computing device 1750 with other devices. The external interface 1762 may provide, for example, for wired communication in some implementations, or for wireless communication in other implementations, and multiple interfaces may also be used.

The memory 1764 stores information within the mobile computing device 1750. The memory 1764 can be implemented as one or more of a computer-readable medium or media, a volatile memory unit or units, or a non-volatile memory unit or units. An expansion memory 1774 may also be provided and connected to the mobile computing device 1750 through an expansion interface 1772, which may include, for example, a SIMM (Single In Line Memory Module) card interface. The expansion memory 1774 may provide extra storage space for the mobile computing device 1750, or may also store applications or other information for the mobile computing device 1750. Specifically, the expansion memory 1774 may include instructions to carry out or supplement the processes described above, and may include secure information also. Thus, for example, the expansion memory 1774 may be provide as a security module for the mobile computing device 1750, and may be programmed with instructions that permit secure use of the mobile computing device 1750. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. The instructions, when executed by one or more processing devices (for example, processor 1752), perform one or more methods, such as those described above. The instructions can also be stored by one or more storage devices, such as one or more computer- or machine-readable mediums (for example, the memory 1764, the expansion memory 1774, or memory on the processor 1752). In some implementations, the instructions can be received in a propagated signal, for example, over the transceiver 1768 or the external interface 1762.

The mobile computing device 1750 may communicate wirelessly through the communication interface 1766, which may include digital signal processing circuitry where necessary. The communication interface 1766 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 1768 using a radio-frequency. In addition, short-range communication may occur, such as using a Bluetooth®, Wi-Fi™, or other such transceiver (not shown). In addition, a GPS (Global Positioning System) receiver module 1770 may provide additional navigation- and location-related wireless data to the mobile computing device 1750, which may be used as appropriate by applications running on the mobile computing device 1750.

The mobile computing device 1750 may also communicate audibly using an audio codec 1760, which may receive spoken information from a user and convert it to usable digital information. The audio codec 1760 may likewise generate audible sound for a user, such as through a speaker, e.g., in a handset of the mobile computing device 1750. Such sound may include sound from voice telephone calls, may include recorded sound (e.g., voice messages, music files, etc.) and may also include sound generated by applications operating on the mobile computing device 1750.

The mobile computing device 1750 may be implemented in a number of different forms, as shown in the figure. For example, it may be implemented as a cellular telephone 1780. It may also be implemented as part of a smart-phone 1782, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

Actions associated with implementing the systems may be performed by one or more programmable processors executing one or more computer programs. All or part of the systems may be implemented as special purpose logic circuitry, for example, a field programmable gate array (FPGA) or an application-specific integrated circuit (ASIC), or both. All or part of the systems may also be implemented as special purpose logic circuitry, for example, a specially designed (or configured) central processing unit (CPU), conventional central processing units (CPU) a graphics processing unit (GPU), and/or a tensor processing unit (TPU).

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some implementations, modules described herein can be separated, combined or incorporated into single or combined modules. The modules depicted in the figures are not intended to limit the systems described herein to the software architectures shown therein.

F. Examples

F.i Example 1: Example Binding Site Prediction Model and Training Procedure

This example describes and demonstrates a training procedure, graph-based machine learning model implementation, and performance results for an example approach for predicting prospective binding sites of a target protein, in accordance with certain embodiments described herein.

Network Architecture

Figure 18:
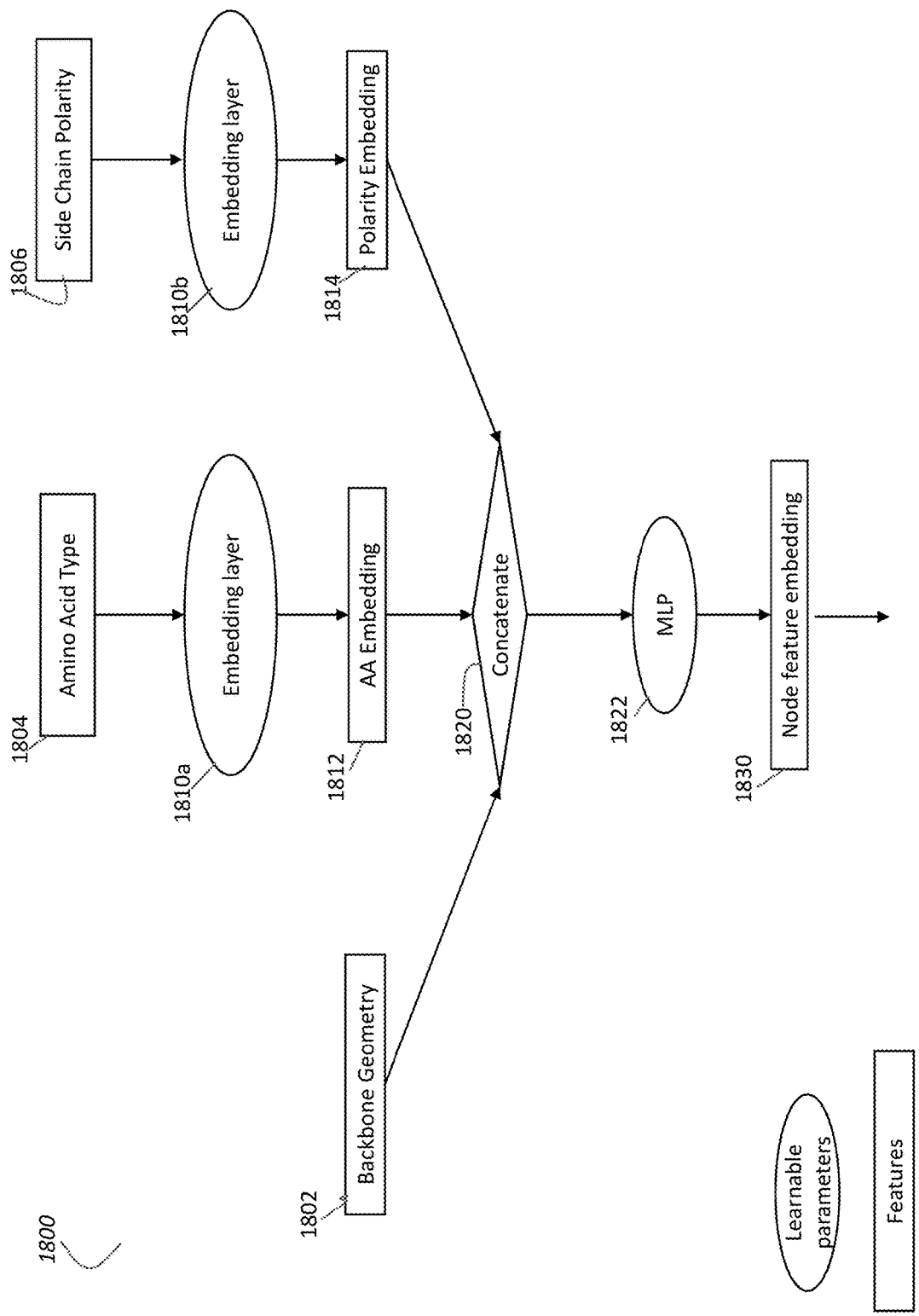
FIG. 18 is a block flow diagram of a portion of an example neural network architecture, according to an illustrative embodiment.
Figure 19:
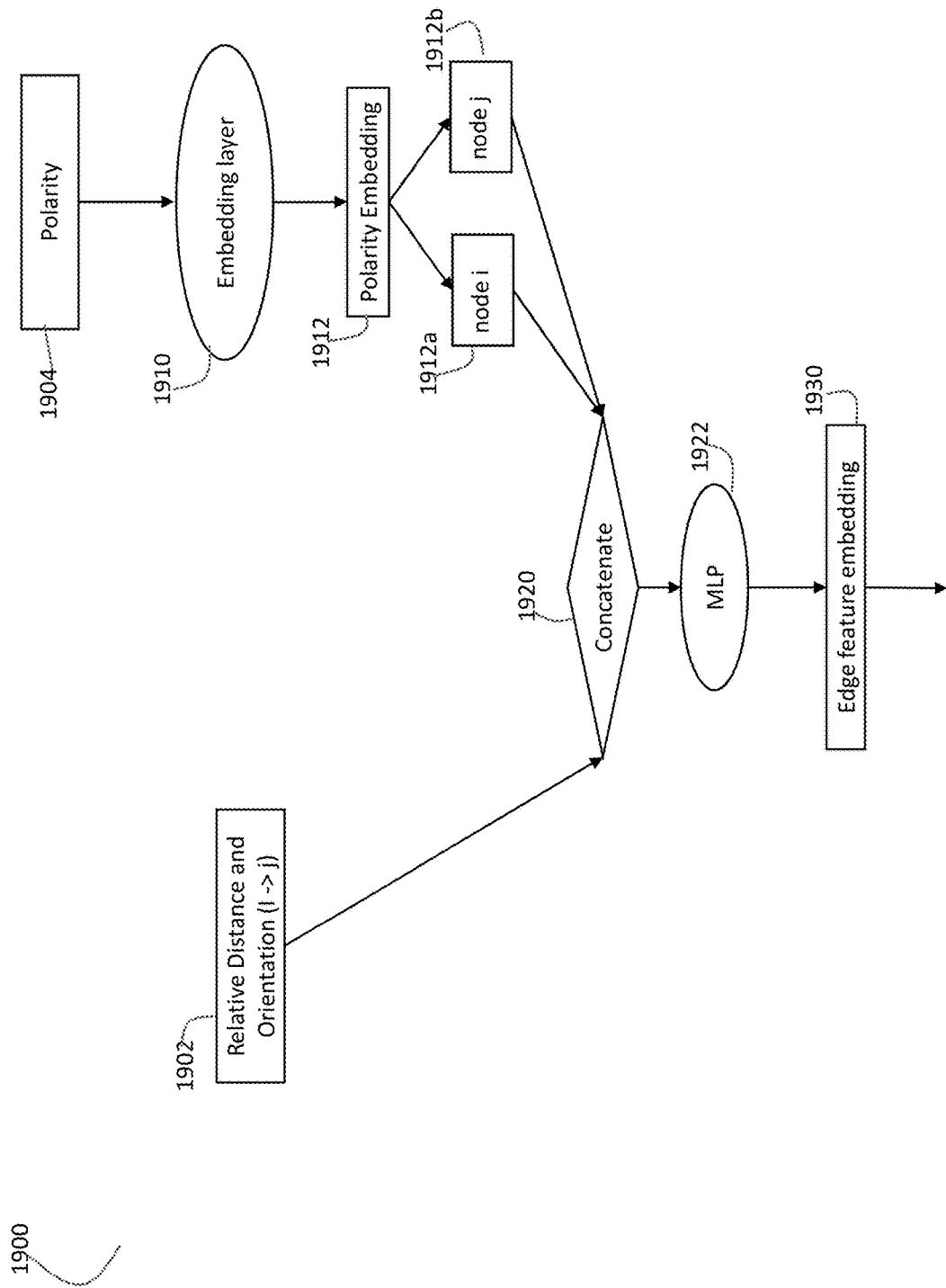
FIG. 19 is a block flow diagram of a portion of an example neural network architecture, according to an illustrative embodiment.

FIGS. 18-20 illustrate the network architecture for the binding site predictor model implemented in this example. The binding site predictor model utilizes a graph-based neural network (GNN) and receives, as input, a graph representation of a particular protein (an input graph) and generates, as output, a binding site prediction. Binding site prediction comprises one or more likelihood values determined for each of at least a portion of the input graph nodes and representing a likelihood that an amino acid site represented by a corresponding input graph node is a binding site.

The input graph representation used in this example is an embodiment of the graph representation approaches described herein, for example at Section C, above. In this example, input graphs comprising both (i) nodes, representing amino acid sites, and (ii) edges, representing relative positioning and interactions between amino acid sites. Each node of an input graph was associated with a node feature vector that encoded properties of the particular amino acid site that it represented. Each edge, connecting two nodes—an $i^{th}$ node to a $j^{th}$ node—comprised an edge feature vector that encoded positional and interactions between amino acid sites represented by the $i^{th}$ and $j^{th}$ nodes. Edge counts in input graph representations used in this example were limited through use of a distance threshold, whereby edges were limited to connections between nodes representing amino acid sites less than or equal to twelve (12) Angstroms apart. This approach was found provide a useful balance between computation time and accuracy, though, as described herein, other approaches, such as using a fully connected graph (where all nodes are connected), k-nearest neighbor approach, etc., also may be used.

In particular, each node feature vector included a local backbone geometry component, an amino acid type component, and a side chain polarity component. Local backbone geometry component was a six element vector, comprising cosine and sine values of each of the three backbone torsion angles, formatted as shown in Equation (2), below (see also FIG. 10B), $$V_{Backbone}=[\cos(\varphi), \sin(\varphi), \cos(\psi), \sin(\psi), \cos(\omega), \sin(\omega)], \quad (2)$$

where the angles $\varphi$, $\psi$, and $\omega$ are the three main peptide backbone torsion angles.

For a node, representing a particular amino acid site, amino acid type component was used to represent a specific amino acid type (e.g., Glycine, Arginine, Histidine, etc.) of the particular amino acid site. A one-hot encoding scheme, as described herein (e.g., at Section C, above and with reference to FIG. 9) was used, such that for each node, amino acid type component was a twenty (20) element vector populated with nineteen (19) zeros and a single "1" value, with the location of the single "1" indexing a specific amino acid type. A side chain polarity component was a single integer, $P_i$, that was assigned one of four discrete values to encode whether a particular side chain was apolar (non-polar), polar, positively charged, or negatively charged, as shown in Table 2, below:

TABLE 2

Polarity values and corresponding representations

| Polarity Value ($P_i$) | Description |
|---|---|
| 0 | Side chain at site i (represented by node i) is non-polar. |
| 1 | Side chain at site i (represented by node i) is polar. |
| 2 | Side chain at site i (represented by node i) is positively charged. |
| 3 | Side chain at site i (represented by node i) is negatively charged. |

Each edge feature vector included components that encoded a relative distance and orientation as well as interaction types between the two nodes that their corresponding edge connected. In particular, for an edge connecting a node i to another node j, the edge feature vector included a relative distance component—a single (floating point) numerical value measuring a distance between the ith and jth CB atoms (see, e.g., FIG. 10), and a relative orientation component, represented as a four element vector comprising cosine and sine values of the side-chain angles $\varphi_{12}$ and $\theta_{12}$, illustrated in FIG. 10. Each edge feature vector also included a two-element interaction component, comprising polarity values for the $i^{th}$ and $j^{th}$ nodes, i.e., [$P_i$, $P_j$], as defined in Table 2, above.

Turning to FIGS. 18-20, the binding site predictor model of the present example comprised three sub-portions, as shown in FIGS. 18-20. As shown in FIGS. 18 and 19, two preliminary, pre-processing portions, 1800 and 1900, were used to process node features and edge features of an input graph representation, to create internal representations—a node feature embedding 1830 and an edge feature embedding 1930—that would be passed along to a graph-neural network (GNN) prediction sub block 2002.

Turning to FIG. 18, pre-processing portion 1800 operates on node feature vectors (from each node) as specified in an input graph representation received by the binding predictor model, to create an internal node feature vector representation 1830. As shown in FIG. 18, sub-components local backbone geometry 1802, amino acid type 1804, and side chain polarity 1806 are processed separately, with both amino acid type component 1804 and side chain polarity 1806 passed to a respective embedding layer, 1810a and 1810b, respectively. Embedding layer 1810a outputs an internal amino acid type representation 1812, based on an input amino acid type component 1804 and polarity embedding representation 1814, both vectors. The initial backbone geometry component 1802 was concatenated with amino acid type embedding representation and polarity embedding representation, and the concatenation of these three vectors passed as input to a multilayer perceptron (MLP) 1822 to create node feature embedding 1830, which is an internal representation of the node feature vector used in the input graph.

Turning to FIG. 19, pre-processing portion 1900 operated edge feature vector components of an input graph. As shown in FIG. 19, polarity interaction component 1904 was provided as input to an embedding layer 1910 to create a polarity embedding representation 1912. In particular, each polarity value (for each node) was passed separately, element-wise, through embedding layer 1910, to create polarity embedding representations for each node 1912a and 1912b separately, rather than, for example, creating an internal representation of the two-element polarity interaction component overall. The relative distance and orientation edge feature vector components 1902 were then concatenated 1920 with the two node polarity embedding values 1912a and 1912b, and the resultant vector passed as input to MLP 1922, to create an edge feature embedding 1930, which is an internal representation of the initial edge feature vector used in the input graph.

Figure 20A:
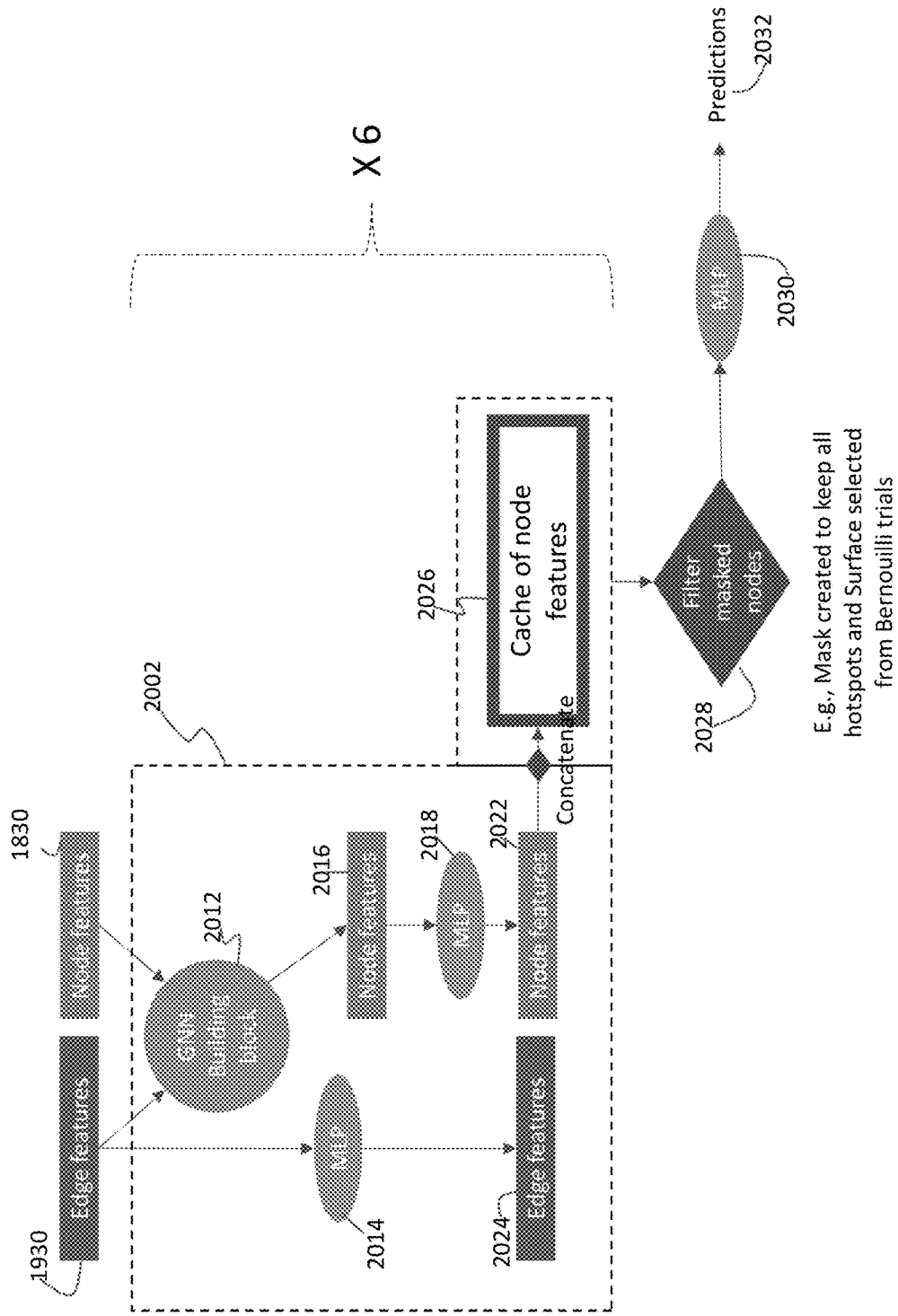
FIG. 20A is a block flow diagram of a portion of an example neural network architecture, according to an illustrative embodiment.
Figure 20B:
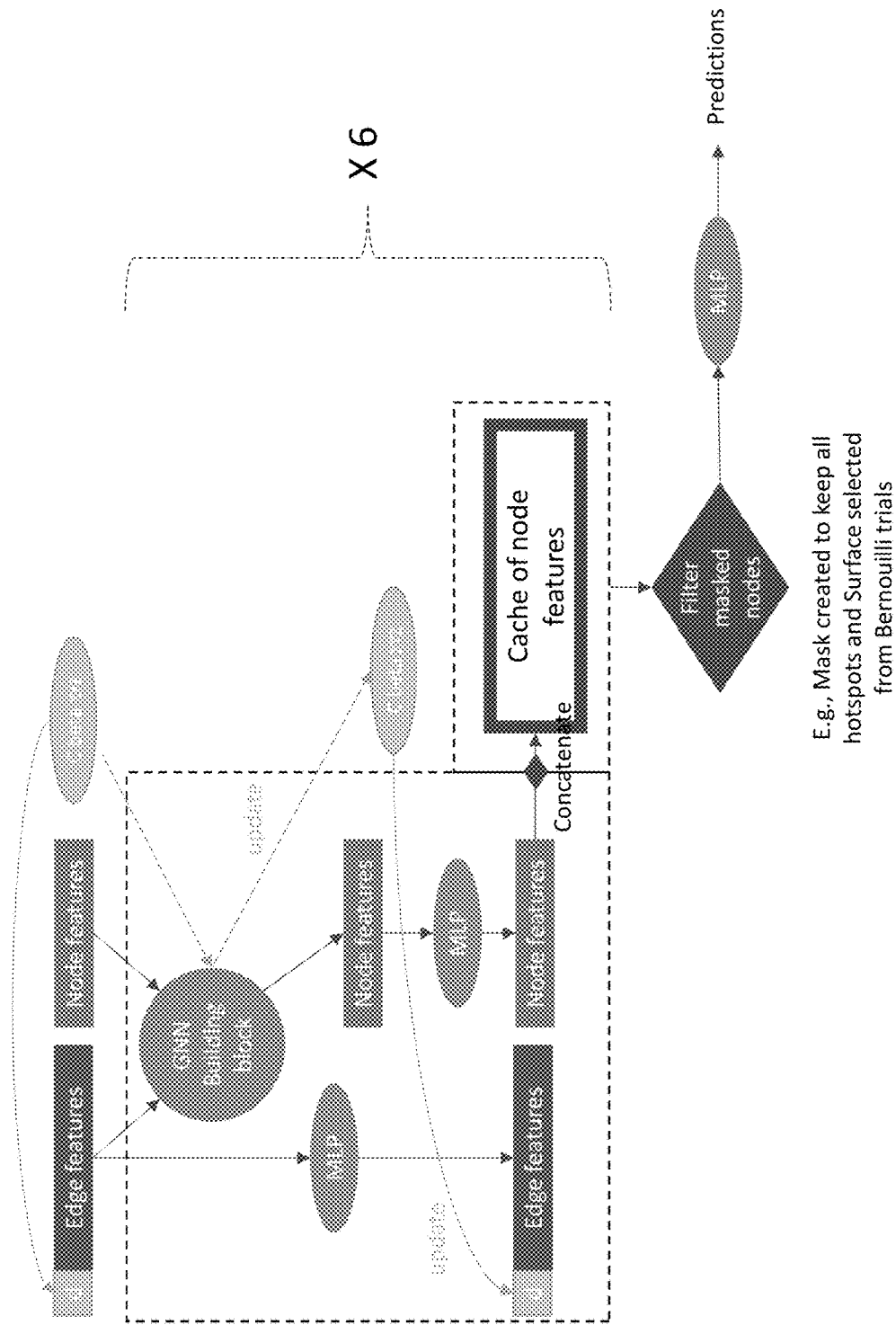
FIG. 20B is a block flow diagram of a portion of an example neural network architecture, according to an illustrative embodiment.

Turning to FIG. 20A, edge feature embedding 1930 and node feature embedding 1830 were then passed as input to a GNN prediction sub-block 2002, which included a GNN block 2012 and two MLPs 2014 and 2018. In particular, node feature embedding 1830 and edge feature embedding 1930 are received as input by GNN block 2012 to generate a first updated (e.g., classified) node feature embedding 2016, which are processed by a MLP 2018 to generate a second updated (e.g., classified) node feature embedding 2022. Edge feature embedding 1930 is also processed by a MLP 2014, to create an updated (e.g., classified) edge feature embedding 2024. As indicated in FIGS. 20A and 20B, six repeated layers (e.g., instances) of GNN prediction sub-block 2022 are used, each having a same architecture, as shown in FIG. 20A, but with independently learnable parameter weights. Updated node feature embedding 2022 and updated edge feature embedding 2024 generate from one layer fed back in as inputs to a subsequent sub-block layer.

At each sub-block layer, updated node feature embedding 2022 generated during that sub-block layer is saved in a eache of node features 2026, with updated node feature embeddings from each sub-block layer appended to a vector of eached features from prior sub-block layers. After six sub-block layers, eached feature vector 2026 comprised six versions of updated node feature embedding 2022, concatenated together. Without wishing to be bound to any particular theory, this approach—eaching updated feature representations after each pass through GNN sub-block 2002 (and, in particular, GNN block 2012)—is believed to address, among other things, over-smoothing issues that can plague deep GNNs.

In the present example, sub-blocks 2022 are stacked as distinct layers—that is, they are allowed to have distinct weights. In other embodiments, a single sub-block 2022 (e.g., having a single set of weights) may be iterated over, e.g., multiple times. In certain embodiments, these approaches (iterating over a sub-block and/or stacking distinct sub-blocks as separate layers) may be used in combination, for example, two or more sub-blocks may be distinct (e.g., in the sense that they have a same architecture, but weights may be different), while one or more sub-blocks may be iterated over, multiple times.

After the final layer of prediction sub-block 2002, eached feature vector 2026 was passed through a node filter 2028 to retain, and therefore generate predictions for, a subset of nodes of an input graph. In particular, node filter 2028 was implemented to retain eached feature vectors for certain nodes corresponding to surface accessible amino acids and discard cashed feature vectors for buried amino acids. For example, various amino acids of a protein may vary in the extent to which they are at are accessible to solvent and/or other molecules or buried, within the protein and away from its surface. In order to discriminate between surface amino acids and buried amino acids, a relative surface accessibility (RSA) metric was used, in which a computed solvent accessible surface area (SASA) for a particular amino acid site was divided by an normalization value for the particular side chain of the site, as follows:

$$RSA = SASA/ASA, \tag{3}$$

where ASA is the normalization value, and was found in Tien et al., "Maximum Allowed Solvent Accessibilities of Residues in Proteins," *PLOS One,* 8(11), e80635 (2013) and the SASA was computed using an implementation of the Shrake and Rupley algorithm, described in Shrake and Rupley, "Environment and exposure to solvent of protein atoms. Lysozome and insulin," *J. Mol. Biol.,* 79(2), 351-71 (1973). Amino acid sites having RSA values at or above 0.16 were classified as surface sites, while those having RSA values below 0.16 were classified as buried sites.

Two different versions of filter step 2028 were used—a first version when binding site predictor model was being trained and another, second version, after training (e.g., during the inference stage) when model was used to generate a new prediction for an unknown target molecule. The second, inference stage, version of filter step 2028 was used to select a subset of nodes whose corresponding amino acid sites were classified as surface sites. The first, training version of filter step 2028 used a slightly different version that selected a subset of nodes that did not necessarily include all surface sites, but, rather, a sampling of possible surface sites, chosen to balance a number of positive and negative ground truth examples (e.g., sites that were a-priori known binding sites and sites that were a-priori known not to be binding sites, e.g., non-binding surface sites) as described in further detail herein.

Figure 24:
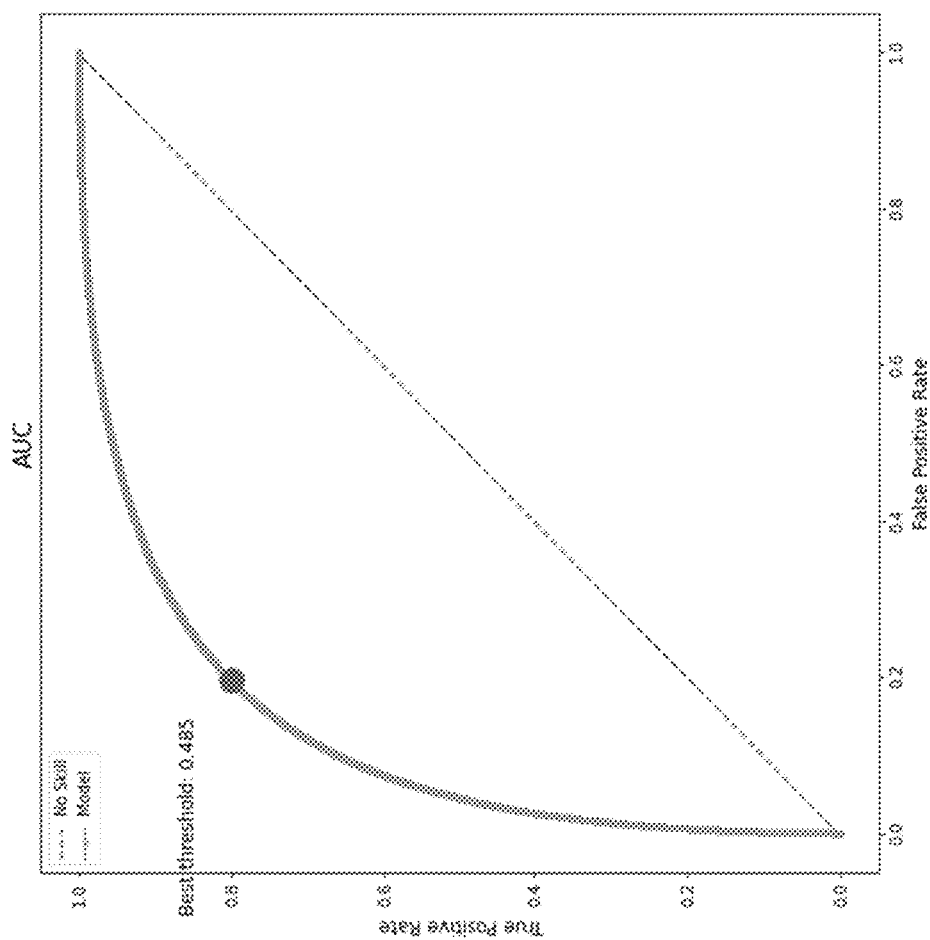
FIG. 24 is a receiver operator characteristic (ROC) curve generated using a machine learning model.

In both cases (training and inference), output of the filtering step 2028 was passed to an MLP 2030 to generate, for each retained node, a likelihood value measuring a predicted likelihood that a particular retained node was a binding site—i.e., would, in the event the protein represented by the input graph formed a complex with another molecule, be a hotspot. To create a final binding site prediction, and classify particular nodes as corresponding to binding sites or not, likelihood values 2032 for each node were compared with a binding site threshold value. Nodes having likelihood values above the binding site threshold value were classified as binding sites, and node having likelihood values below it were classified as non-binding sites. The particular threshold value used could be tuned, for example as shown in FIG. 24 to vary rates of true positives and false positives.

FIG. 20B shows another version of the portion of the machine learning model shown in FIG. 20A. The version shown in FIG. 20B utilizes absolute coordinates of each amino acid site—in particular, the (x, y, z) coordinates of each amino acid site's $C_\beta$. Beta-carbon coordinates were used to compute a $C_\beta$ distance value ("d" in FIG. 20B) for two nodes connected by each edge, which was appended/inserted in to the edge's feature vector. As shown in FIG. 20B, $C_\beta$ coordinate values were also fed into each layer's GNN block, and updated as described in Satorras et al., "E(n) Equivariant Graph Neural Networks," *Proc.* 38$^{th}$ *Int. Conf. Machine Learning,* PMLR 139, 2021, to ensure equivariance with respect to 3D rotation and translation operations.

Training Dataset Creation

The training approach of this example utilized models of protein complexes obtained from the protein data bank (PDB). PDB files (e.g., text files that specify protein 3D structure) for complexes comprising multiple (two or more) protein chains were obtained and organized into clusters in order to create a balanced dataset for training. In particular, since the PDB includes experimentally determined structures for proteins and peptides, it is biased towards the most heavily studied proteins and complexes thereof. That is, certain heavily studied proteins and protein systems will have a large number of redundant experimental structures stored in the PDB, whereas less common and/or less widely studied proteins may have few or no structures in the PDB. A balancing approach that used clustering analysis was employed to accurately represent the diversity in protein structures during training.

To obtain a balanced data set, chains obtained from PDB files were analyzed based on their sequences and arranged into clusters based on 30% sequence identity—that is, chains that had 30% or greater sequence identity were clustered together. Beginning with 51,724 chains, 8,922 clusters were obtained. Cluster indices were then used as nodes to find connected components, which were then merged to create a total of 6,618 merged clusters. The five largest connected components were identified and placed in the training dataset. Of the remaining clusters, 20% were selected at random to create a test dataset. Accordingly, of the 8,923 clusters in the initial dataset, 1,305 (14.63%) were selected to create the test dataset, and the remaining 7,618 (85.38%).

For each complex in the training and test dataset, the PDB file was used to create a corresponding graph representation. Each complex graph comprised a plurality of nodes and edges, having corresponding feature vectors as described herein. For each complex, amino acid sites were classified as hotspots or not, based on a threshold distance of 8 Angstroms. Graphs created for each complex were split into their constituent chains, and an example graph extracted for each chain. Chains comprising less than twenty (20) amino acids and less than five hotspots were removed—excluded from the training and test datasets. Example chain graphs were then binned according to the cluster index for the complex from which they were extracted.

Figure 21:
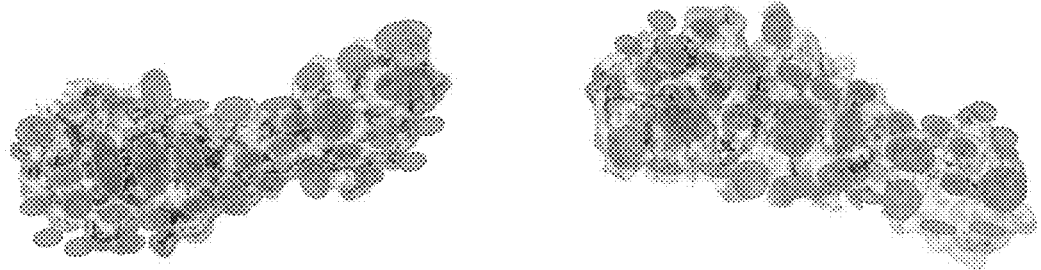
FIG. 21 is a schematic showing a portion of two polypeptide chains, according to an illustrative embodiment.
Figure 21:
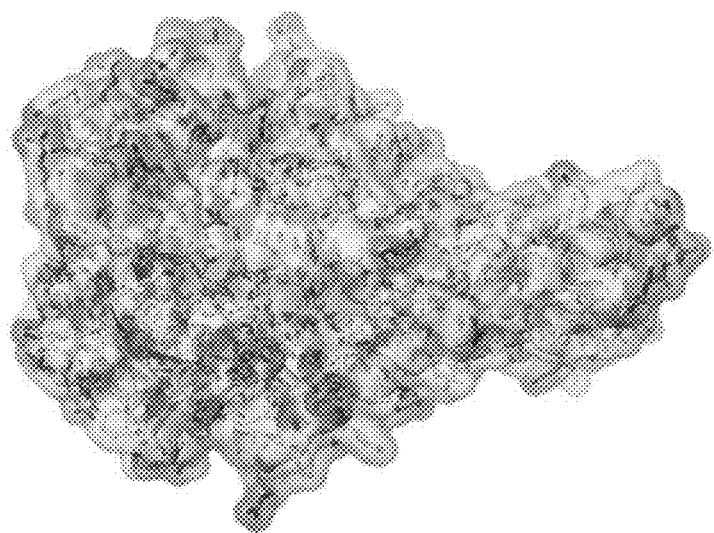

Amino acid sites of each chain were also classified as surface sites or not (e.g., buried sites) by comparing their RSA values to a threshold. Amino acid sites having RSA values at or above the threshold were classified as surface sites. Amino acid sites that were identified as hotspots when the particular chain was in complex and had an RSA value above the threshold were classified as binding sites. In this example, a threshold of 0.16 was used. In this manner, for each example chain, a set of surface sites and a set of binding sites were identified, as illustrated in FIG. 21.

This procedure produced a training dataset comprising 125,316 example chain graphs, arranged in 7,379 clusters (85% of the initial clusters) and a test dataset comprising 18,682 example chain graphs, arranged in 1,292 clusters (15% of the initial clusters).

Example Training Strategy

Figure 22:
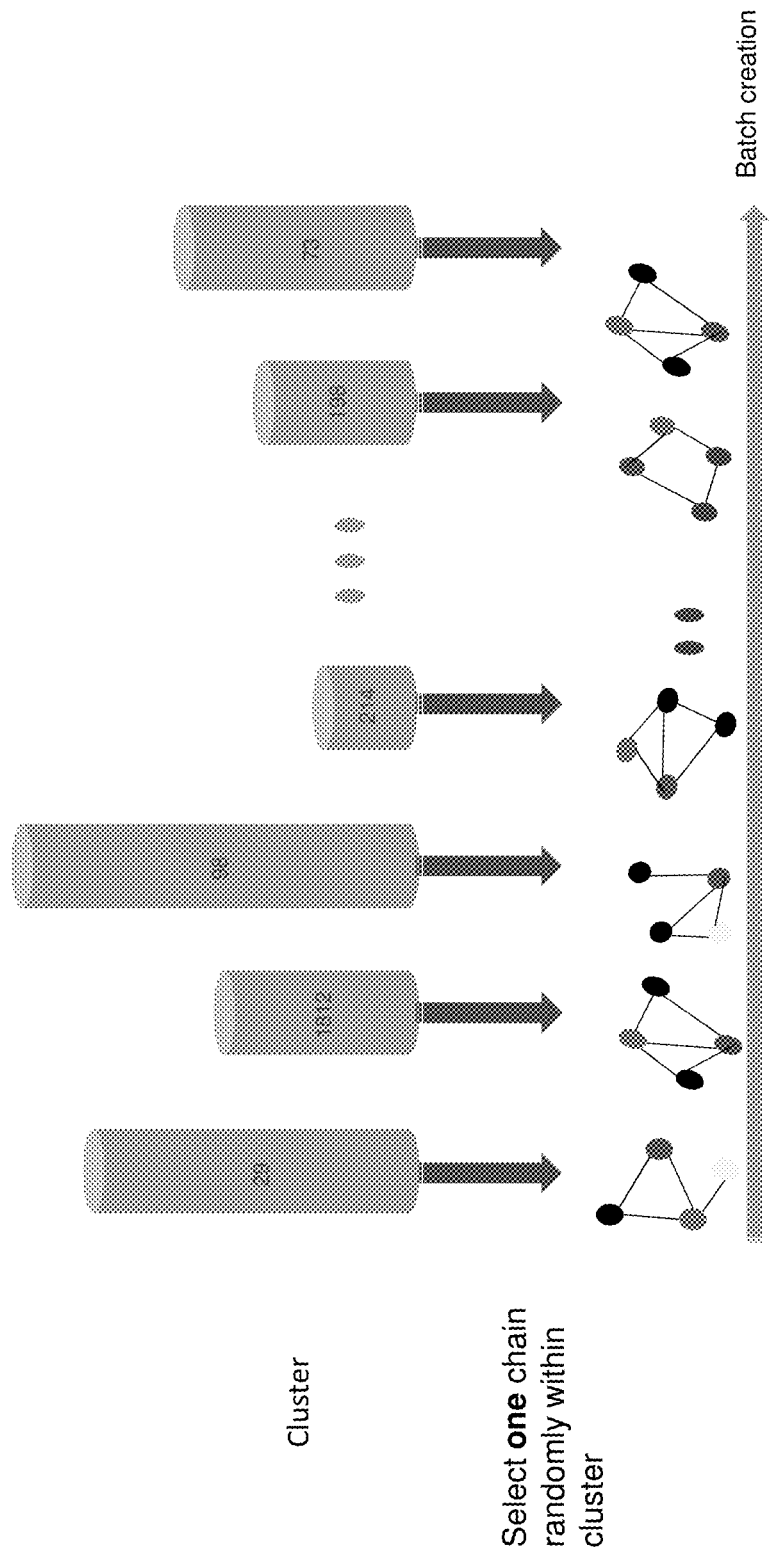
FIG. 22 is a diagram illustrating an example approach for creating a batch of examples to use for training a binding site prediction model, according to an illustrative embodiment.

During training, one example chain was selected at random from each cluster to create a batch of example chains to uses as training input to the neural network model, as illustrated in FIG. 22.

For each example chain, the binding site predictor model received a graph representation of the example chain as input, and classified a subset of the nodes as binding sites or not. In order to evaluate the accuracy of the binding site predictor model to classify binding sites, and update weights accordingly, a loss function was computed using a balanced subset of amino acid sites, comprising an approximately equal number of binding sites and non-binding surface sites. In particular, binding site predictor model was tasked with generating predictions for those amino acid sites that had been identified as binding sites, as well as a random sampling of surface sites. In order to balance the number of binding sites and surface sites nodes corresponding to surface sites were selected based on a Bernoulli probability.

Finally, the loss function was weighted to account for outliers where a number of binding sites exceeded a number of (non-binding) surface sites and a classic weighted Cross Entropy Loss with mean aggregation used to measure loss at each batch. Weighting functions used in this example are shown in Equations (4a-d), below:

$$Wh = \min(\#hotspots, \#surface\ nnodes)/\#hotspots, \quad (4a)$$

$$Ws = \min(hotspots, \#surface\ nodes)/\#surface\ nodes, \quad (4b)$$

$$W_{yh} = W_h/W_s + W_h, \text{ and} \quad (4c)$$

$$W_{yh} = W_s/W_s + W_h \quad (4d)$$

Results

Figure 23:
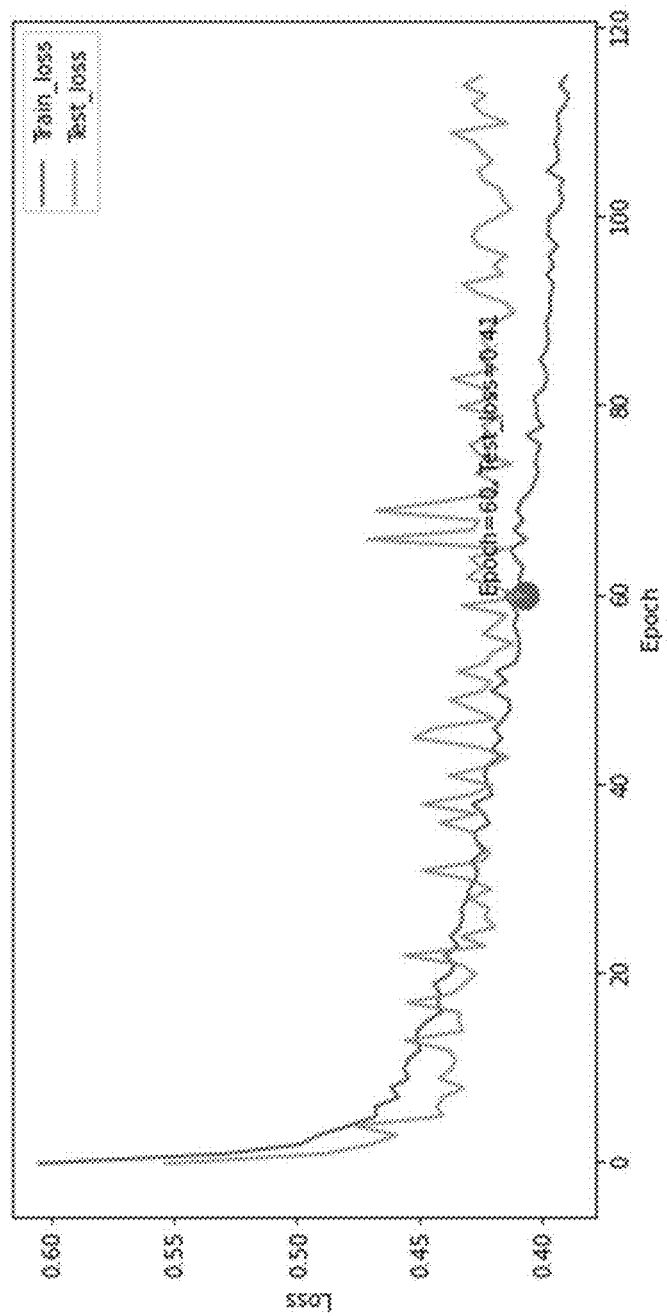
FIG. 23 is a graph shown improvement in a loss function during training of an example machine learning model.

FIG. 23 shows performance results of the example training procedure of the present example applied to the training and test datasets that were created as described herein. During training, as illustrated, e.g., in FIG. 22, during each epoch, one chain was sampled from each cluster of the training dataset and the loss function evaluated over each example chain. The average loss over all examples during each epoch is shown in FIG. 23 for the training set. A similar procedure was used to evaluate performance of the model at each epoch using the test dataset described herein, whereby at each epoch, one chain was sampled from each cluster of the test dataset, and the loss function evaluated for each example chain and averaged to produce the test loss data shown in FIG. 23. For the first 60 epochs, performance measured on the training and test datasets improves together. After 60 epochs, test dataset performance plateaus, while training dataset performance continues to improve, indicating optimal performance at around 60 epochs, and overtraining thereafter.

FIG. 24 shows a receiver operating characteristic (ROC) curve created by varying binding site cutoff threshold while applying a trained model to a benchmark set created from the test dataset by removing example chains less than twenty amino acids in length (leaving 1,292 clusters) and selecting twenty example chains from each cluster, at random, to obtain 25,840 example chains in total, which were represented as graphs. Certain clusters were oversampled (e.g., particular chains sampled multiple times) via this approach, however, since the surface nodes changed at each iteration, distinct sets of surface nodes were still selected for prediction. For each selected chain, filtering step 2028 was used to select all a-priori identified hotspot sites and a randomly equivalent number of surface sites. The binding site prediction model described in this example was then used to generate likelihood predictions for each of the selected a-priori identified hotspot sites and selected surface sites, generating predictions for a total of 2,026,902 sites overall, comprising 1,066,966 hotspot nodes (labeled 1) and 959,936 non-binding surface sites (labeled "0"), reflecting the intended 50/50 split between hotspots and non-binding surface sites. The ROC curve shown in FIG. 24 was generated by varying the threshold value to which the likelihood prediction generated for each particular site was compared, in order to classify that site as a hotspot or non-binding surface site. An optimal threshold, determined as the threshold value that maximized the sum of sensitivity and specificity (e.g., computed as TruePositiveRate (TPR)+(1−FalsePositiveRate (FPR))) was found to be 0.4853. This threshold resulted in a true-positive rate (TPR) of 0.8004, a false positive rate of 0.1954, an F1-Score of 0.8021, and an Accuracy of 0.802. The overall Area Under the Curve (AUC) was 0.8852.

Accordingly, this example demonstrates accurate performance of a binding site predictor model in accordance with certain embodiments described herein.

EQUIVALENTS

Elements of different implementations described herein may be combined to form other implementations not specifically set forth above. Elements may be left out of the processes, computer programs, databases, etc. described herein without adversely affecting their operation. In addition, the logic flows depicted in the figures do not require the particular order shown, or sequential order, to achieve desirable results. Various separate elements may be combined into one or more individual elements to perform the functions described herein.

Throughout the description, where apparatus and systems are described as having, including, or comprising specific components, or where processes and methods are described as having, including, or comprising specific steps, it is contemplated that, additionally, there are apparatus, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method for identifying one or more prospective binding sites on a target comprising one or more proteins, the method comprising:
   (a) obtaining, by a processor of a computing device, a target graph representing at least a portion of the target, the target graph comprising a plurality of target nodes, each corresponding to and representing a particular amino acid site of the portion of the target and having an associated node feature vector comprising one or more constituent feature vectors representing features of the particular amino acid site;
   (b) generating, by the processor, using a machine learning model, a likelihood graph based on the target graph, wherein the machine learning model:
     is or comprises a neural network having been trained using a plurality of training examples, each training example representing one or more member chains of a particular existing biological complex, with one more binding partners removed, wherein amino acid sites of the one or more member chains that interact with the one or more binding partners are labeled;
     receives at least the target graph as input; and
     generates, as output, the likelihood graph, wherein the likelihood graph comprises, for each of at least a portion of the target nodes of the target graph, a corresponding likelihood that an amino acid site represented by the target node is or could be involved in a binding interaction with another protein and/or peptide; and (c) determining, by the processor, based on the likelihood graph, an identification of one or more binding sites, each representing an amino acid site of the target likely to influence binding with another protein.

2. The method of claim 1, comprising providing, by the processor, the identification of the one or more binding sites for use in designing a custom biologic.

3. The method of claim 1, wherein the target graph is or comprises a representation of the portion of the target in isolation, not bound to other binding partners in complex.

4. The method of claim 1, wherein the target graph is or comprises a representation of at least a portion of one or more members selected from the group consisting of: a monomer; a dimer; a trimer; and a multimer.

5. The method of claim 1, wherein the target graph comprises a plurality of edges, each associated with two particular nodes and having a corresponding edge feature vector comprising one or more constituent vectors representing a relative orientation of, and/or distance between, two amino acid sites represented by the two particular nodes.

6. A system for identifying one or more prospective binding sites on a target comprising one or more proteins, the system comprising:
   a processor of a computing device; and
   a memory having instructions stored thereon, wherein the instructions, when executed by the processor, cause the processor to:
   (a) obtain a target graph representing at least a portion of the target, the target graph comprising a plurality of target nodes, each corresponding to and representing a particular amino acid site of the portion of the target and having an associated node feature vector comprising one or more constituent feature vectors representing features of the particular amino acid site;
   (b) generate, using a machine learning model, a likelihood graph based on the target graph, wherein the machine learning model:
       is or comprises a neural network having been trained using a plurality of training examples, each training example representing one or more member chains of a particular existing biological complex, with one or more binding partners removed, wherein amino acid sites of the one or more member chains that interact with the one or more binding partners are labeled;
       receives at least the target graph as input; and
       generates, as output, the likelihood graph, wherein the likelihood graph comprises, for each of at least a portion of the target nodes of the target graph, a corresponding likelihood that an amino acid site represented by the target node is or could be involved in a binding interaction with another protein and/or peptide; and
   (c) determine, based on the likelihood graph, an identification of one or more binding sites, each representing an amino acid site of the target likely to influence binding with another protein.

7. The method of claim 1, wherein each of the target nodes has a node feature vector comprising an amino acid type constituent vector that represents a particular type of amino acid.

8. The method of claim 1, wherein each of the target nodes has a node feature vector comprising one or more constituent vectors encoding a local backbone geometry at the corresponding amino acid site.

9. The method of claim 1, wherein each of the target nodes has a node feature vector comprising one or more constituent vectors encoding a measure of solvent exposed surface area of the corresponding amino acid site.

10. The method of claim 1, wherein each of the target nodes has a node feature vector comprising one or more constituent vectors representing a curvature and/or convexity at the corresponding amino acid site.

11. The method of claim 1, wherein each of the target nodes has a node feature vector comprising one or more constituent vectors representing a constituent vector that represents a positional encoding that identifies a position in sequence of the corresponding amino acid site.

12. The system of claim 6, comprising providing, by the processor, the identification of the one or more binding sites for use in designing a custom biologic.

13. The system of claim 6, wherein the target graph is or comprises a representation of the portion of the target in isolation, not bound to other binding partners in complex.

14. The system of claim 6, wherein the target graph comprises a plurality of edges, each associated with two particular nodes and having a corresponding edge feature vector comprising one or more constituent vectors representing a relative orientation of, and/or distance between, two amino acid sites represented by the two particular nodes.

15. The system of claim 6, wherein each of the target nodes has a node feature vector comprising an amino acid type constituent vector that represents a particular type of amino acid.

16. The system of claim 6, wherein each of the target nodes has a node feature vector comprising one or more constituent vectors encoding a local backbone geometry at the corresponding amino acid site.

17. The system of claim 6, wherein each of the target nodes has a node feature vector comprising one or more constituent vectors encoding a measure of solvent exposed surface area of the corresponding amino acid site.

18. The system of claim 6, wherein each of the target nodes has a node feature vector comprising one or more constituent vectors representing a curvature and/or convexity at the corresponding amino acid site.

19. The system of claim 6, wherein each of the target nodes has a node feature vector comprising one or more constituent vectors representing a constituent vector that represents a positional encoding that identifies a position in sequence of the corresponding amino acid site.

\* \* \* \* \*